(12) United States Patent
Bessette et al.

(10) Patent No.: US 6,920,883 B2
(45) Date of Patent: Jul. 26, 2005

(54) METHODS AND APPARATUS FOR SKIN TREATMENT

(75) Inventors: Andre P. Bessette, San Francisco, CA (US); James L. Pacek, Coto De Caza, CA (US)

(73) Assignee: Arthrocare Corporation, Austin, TX (US)

(*) Notice: Subject to any disclaimer, the term of this patent is extended or adjusted under 35 U.S.C. 154(b) by 97 days.

(21) Appl. No.: 10/291,213

(22) Filed: Nov. 8, 2002

(65) Prior Publication Data

US 2003/0120269 A1 Jun. 26, 2003

Related U.S. Application Data

(60) Provisional application No. 60/337,496, filed on Nov. 8, 2001.

(51) Int. Cl.⁷ .............................. A61B 19/00
(52) U.S. Cl. ........................ 128/898; 606/41
(58) Field of Search ............... 606/32–34, 41, 606/48–50; 607/101, 102; 128/898

(56) References Cited

U.S. PATENT DOCUMENTS

| | | |
|---|---|---|
| 2,056,377 A | 10/1936 | Wappler |
| 3,815,604 A | 6/1974 | OMalley et al. |
| 3,828,780 A | 8/1974 | Morrison, Jr. et al. |
| 3,901,242 A | 8/1975 | Storz |
| 3,920,021 A | 11/1975 | Hiltebrandt |
| 3,939,839 A | 2/1976 | Curtiss |
| 3,970,088 A | 7/1976 | Morrison |
| 4,040,426 A | 8/1977 | Morrison, Jr. |
| 4,043,342 A | 8/1977 | Morrison, Jr. |
| 4,074,718 A | 2/1978 | Morrison, Jr. |
| 4,092,986 A | 6/1978 | Schneiderman |
| 4,116,198 A | 9/1978 | Roos |
| 4,181,131 A | 1/1980 | Ogiu |

(Continued)

FOREIGN PATENT DOCUMENTS

| | | | |
|---|---|---|---|
| DE | 3930451 | 3/1991 | ........... A61B/17/39 |
| EP | 0 703 461 | 3/1996 | ........... G01R/27/02 |

(Continued)

OTHER PUBLICATIONS

US 5,326,343, 7/1994, Rudie (withdrawn)
Pearce, John A. (1986) *Electrosurgery*, pp. 17, 69–75, 87, John Wiley & Sons, New York.
J.W. Ramsey et al. *Urological Research* vol. 13, pp. 99–102 (1985).
V.E. Elasasser et al. *Acta Medicotechnica* vol. 24, No. 4, pp. 129–134 (1976).
P.C. Nardella (1989) *SPIE* 1068: 42–49 Radio Frequency Energy and Impedance Feedback.

(Continued)

*Primary Examiner*—Michael Peffley
(74) *Attorney, Agent, or Firm*—John T. Raffle; Richard R. Batt

(57) ABSTRACT

Methods and apparatus for electrosurgically treating human skin. The skin may be treated by applying thermal energy to the dermis to shrink the skin following liposuction, or to induce collagen deposition at the site of a wrinkle for wrinkle reduction or removal. In another embodiment, a method involves electrosurgically removing or modifying tissue in the head or neck to provide a face-lift or a neck-lift. In one embodiment, the working end of an electrosurgical instrument is positioned in at least close proximity to the dermis by approaching the dermis from the underside (reverse side) of the skin.

29 Claims, 43 Drawing Sheets

U.S. PATENT DOCUMENTS

| | | |
|---|---|---|
| 4,184,492 A | 1/1980 | Meinke et al. |
| 4,202,337 A | 5/1980 | Hren et al. |
| 4,228,800 A | 10/1980 | Degler, Jr. et al. |
| 4,232,676 A | 11/1980 | Herczog |
| 4,248,231 A | 2/1981 | Herczog et al. |
| 4,326,529 A | 4/1982 | Doss et al. |
| 4,381,007 A | 4/1983 | Doss |
| 4,476,862 A | 10/1984 | Pao |
| 4,532,924 A | 8/1985 | Auth et al. |
| 4,548,207 A | 10/1985 | Reimels |
| 4,567,890 A | 2/1986 | Ohta et al. |
| 4,590,934 A | 5/1986 | Malis et al. |
| 4,593,691 A | 6/1986 | Lindstrom et al. |
| 4,658,817 A | 4/1987 | Hardy |
| 4,660,571 A | 4/1987 | Hess et al. |
| 4,674,499 A | 6/1987 | Pao |
| 4,682,596 A | 7/1987 | Bales et al. |
| 4,706,667 A | 11/1987 | Roos |
| 4,727,874 A | 3/1988 | Bowers et al. |
| 4,736,743 A | 4/1988 | Daikuzono |
| 4,737,678 A | 4/1988 | Hasegawa |
| 4,762,128 A | 8/1988 | Rosenbluth |
| 4,765,331 A | 8/1988 | Petruzzi et al. |
| 4,785,806 A | 11/1988 | Deckelbaum |
| 4,785,823 A | 11/1988 | Eggers et al. |
| 4,799,480 A | 1/1989 | Abraham et al. |
| 4,805,616 A | 2/1989 | Pao |
| 4,823,791 A | 4/1989 | DAmelio et al. |
| 4,832,048 A | 5/1989 | Cohen |
| 4,920,978 A | 5/1990 | Colvin |
| 4,931,047 A | 6/1990 | Broadwin et al. |
| 4,936,281 A | 6/1990 | Stasz |
| 4,936,301 A | 6/1990 | Rexroth et al. |
| 4,943,290 A | 7/1990 | Rexroth et al. |
| 4,966,597 A | 10/1990 | Cosman |
| 4,967,765 A | 11/1990 | Turner et al. |
| 4,968,314 A | 11/1990 | Michaels |
| 4,976,711 A | 12/1990 | Parins et al. |
| 4,979,948 A | 12/1990 | Geddes et al. |
| 4,998,933 A | 3/1991 | Eggers et al. |
| 5,007,437 A | 4/1991 | Sterzer |
| 5,007,908 A | 4/1991 | Rydell |
| 5,009,656 A | 4/1991 | Reimels |
| 5,035,696 A | 7/1991 | Rydell |
| 5,037,421 A | 8/1991 | Boutacoff et al. |
| 5,047,026 A | 9/1991 | Rydell |
| 5,047,027 A | 9/1991 | Rydell |
| 5,059,192 A | 10/1991 | Zaias |
| 5,061,266 A | 10/1991 | Hakky |
| 5,065,515 A | 11/1991 | Iderosa |
| 5,078,717 A | 1/1992 | Parins et al. |
| 5,080,660 A | 1/1992 | Buelna |
| 5,084,044 A | 1/1992 | Quint |
| 5,085,659 A | 2/1992 | Rydell |
| 5,088,997 A | 2/1992 | Delahuerga et al. |
| 5,098,431 A | 3/1992 | Rydell |
| 5,099,840 A | 3/1992 | Goble |
| 5,102,410 A | 4/1992 | Dressel |
| 5,108,391 A | 4/1992 | Flachenecker et al. |
| 5,112,330 A | 5/1992 | Nishigaki et al. |
| 5,122,138 A | 6/1992 | Manwaring |
| 5,125,928 A | 6/1992 | Parins et al. |
| 5,143,063 A | 9/1992 | Fellner |
| 5,147,354 A | 9/1992 | Boutacoff |
| 5,167,659 A | 12/1992 | Ohtomo et al. |
| 5,171,311 A | 12/1992 | Rydell et al. |
| 5,178,620 A | 1/1993 | Eggers et al. |
| 5,182,857 A | 2/1993 | Simon |
| 5,190,517 A | 3/1993 | Zieve et al. |
| 5,192,280 A | 3/1993 | Parins |
| 5,195,959 A | 3/1993 | Smith |
| 5,197,466 A | 3/1993 | Marchosky et al. |
| 5,197,963 A | 3/1993 | Parins |
| 5,207,675 A | 5/1993 | Canady |
| 5,217,455 A | 6/1993 | Tan |
| 5,217,457 A | 6/1993 | Delahuerga et al. |
| 5,217,459 A | 6/1993 | Kamerling |
| 5,226,907 A | 7/1993 | Tankovich |
| 5,231,984 A | 8/1993 | Santana-Blank |
| 5,241,972 A | 9/1993 | Bonati |
| 5,261,410 A | 11/1993 | Alfano et al. |
| 5,267,994 A | 12/1993 | Gentelia et al. |
| 5,267,997 A | 12/1993 | Farin et al. |
| 5,273,524 A | 12/1993 | Fox et al. |
| 5,277,201 A | 1/1994 | Stern |
| 5,287,380 A | 2/1994 | Hsia |
| 5,290,273 A | 3/1994 | Tan |
| 5,290,282 A | 3/1994 | Casscells |
| 5,300,069 A | 4/1994 | Hunsberger et al. |
| 5,300,099 A | 4/1994 | Rudie |
| 5,301,687 A | 4/1994 | Wong et al. |
| 5,304,169 A | 4/1994 | Sand |
| 5,304,170 A | 4/1994 | Green |
| 5,306,238 A | 4/1994 | Fleenor |
| 5,312,395 A | 5/1994 | Tan et al. |
| 5,312,400 A | 5/1994 | Bales et al. |
| 5,314,406 A | 5/1994 | Arias et al. |
| 5,320,618 A | 6/1994 | Gustafsson |
| 5,322,507 A | 6/1994 | Costello et al. |
| 5,324,254 A | 6/1994 | Phillips |
| 5,329,943 A | 7/1994 | Johnson |
| 5,330,470 A | 7/1994 | Hagen |
| 5,330,518 A | 7/1994 | Neilson et al. |
| 5,334,140 A | 8/1994 | Phillips |
| 5,336,217 A | 8/1994 | Buys et al. |
| 5,342,357 A | 8/1994 | Nardella |
| 5,360,447 A | 11/1994 | Koop |
| 5,366,443 A | 11/1994 | Eggers et al. |
| 5,370,642 A | 12/1994 | Keller |
| 5,370,675 A | 12/1994 | Edwards et al. |
| 5,375,588 A | 12/1994 | Yoon |
| 5,380,277 A | 1/1995 | Phillips |
| 5,380,316 A | 1/1995 | Aita et al. |
| 5,383,876 A | 1/1995 | Nardella |
| 5,383,917 A | 1/1995 | Desai et al. |
| 5,389,096 A | 2/1995 | Aita et al. |
| 5,395,312 A | 3/1995 | Desai |
| 5,417,687 A | 5/1995 | Nardella et al. |
| 5,419,767 A | 5/1995 | Eggers et al. |
| 5,423,803 A | 6/1995 | Tankovich et al. |
| 5,423,810 A | 6/1995 | Goble et al. |
| 5,423,882 A | 6/1995 | Jackman et al. |
| 5,425,728 A | 6/1995 | Tankovich |
| 5,433,708 A | 7/1995 | Nichols et al. |
| 5,436,566 A | 7/1995 | Thompson et al. |
| 5,438,302 A | 8/1995 | Goble |
| 5,441,499 A | 8/1995 | Fritzsch |
| 5,445,634 A | 8/1995 | Keller |
| 5,449,378 A | 9/1995 | Schouenborg |
| 5,451,224 A | 9/1995 | Goble et al. |
| 5,454,809 A | 10/1995 | Janssen |
| 5,484,435 A | 1/1996 | Fleenor et al. |
| 5,490,850 A | 2/1996 | Ellman et al. |
| 5,496,312 A | 3/1996 | Klicek |
| 5,496,314 A | 3/1996 | Eggers |
| 5,496,317 A | 3/1996 | Goble et al. |
| 5,507,790 A | 4/1996 | Weiss |
| 5,514,130 A | 5/1996 | Baker |
| 5,522,813 A | 6/1996 | Trelles |
| 5,556,397 A | 9/1996 | Long et al. |
| 5,569,242 A | 10/1996 | Lax et al. |

| | | |
|---|---|---|
| 5,571,100 A | 11/1996 | Goble et al. |
| 5,578,029 A | 11/1996 | Trelles et al. |
| 5,584,872 A | 12/1996 | LaFontaine et al. |
| 5,609,151 A | 3/1997 | Mulier et al. |
| 5,633,578 A | 5/1997 | Eggers et al. |
| 5,647,869 A | 7/1997 | Goble et al. |
| 5,660,836 A | 8/1997 | Knowlton |
| 5,662,680 A | 9/1997 | Desai |
| 5,676,693 A | 10/1997 | LaFontaine |
| 5,681,282 A | 10/1997 | Eggers et al. |
| 5,683,366 A | 11/1997 | Eggers et al. |
| 5,683,386 A | 11/1997 | Ellman et al. |
| 5,683,387 A | 11/1997 | Garito et al. |
| 5,695,495 A | 12/1997 | Ellman et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,700,262 A | 12/1997 | Acosta et al. |
| 5,725,524 A | 3/1998 | Mulier et al. |
| 5,746,746 A | 5/1998 | Garito et al. |
| 5,755,753 A * | 5/1998 | Knowlton .................... 607/98 |
| 5,766,153 A | 6/1998 | Eggers et al. |
| 5,807,395 A | 9/1998 | Mulier et al. |
| 5,810,764 A | 9/1998 | Eggers et al. |
| 5,810,809 A | 9/1998 | Rydell |
| 5,843,019 A | 12/1998 | Eggers et al. |
| 5,843,078 A | 12/1998 | Sharkey |
| 5,860,951 A | 1/1999 | Eggers et al. |
| 5,860,975 A | 1/1999 | Goble et al. |
| 5,871,469 A | 2/1999 | Eggers et al. |
| 5,873,855 A | 2/1999 | Eggers et al. |
| 5,885,277 A | 3/1999 | Korth |
| 5,888,198 A | 3/1999 | Eggers et al. |
| 5,891,095 A | 4/1999 | Eggers et al. |
| 5,897,553 A | 4/1999 | Mulier |
| 5,902,272 A | 5/1999 | Eggers et al. |
| 5,931,807 A | 8/1999 | McClure et al. |
| 5,944,715 A | 8/1999 | Goble et al. |
| 5,948,011 A | 9/1999 | Knowlton |
| 6,004,319 A | 12/1999 | Goble et al. |
| 6,013,076 A | 1/2000 | Goble et al. |
| 6,015,406 A | 1/2000 | Goble et al. |
| 6,024,733 A | 2/2000 | Eggers et al. |
| 6,027,501 A | 2/2000 | Goble et al. |
| 6,039,734 A | 3/2000 | Goble et al. |
| 6,047,215 A | 4/2000 | McClure et al. |
| 6,056,746 A | 5/2000 | Goble et al. |
| 6,063,079 A | 5/2000 | Hovda et al. |
| 6,066,134 A | 5/2000 | Eggers et al. |
| 6,068,628 A | 5/2000 | Fanton et al. |
| 6,074,386 A | 6/2000 | Goble et al. |
| 6,090,106 A | 7/2000 | Goble et al. |
| 6,093,186 A | 7/2000 | Goble et al. |
| 6,102,046 A | 8/2000 | Weinstein et al. |
| 6,109,268 A | 8/2000 | Thapliyal et al. |
| 6,117,109 A * | 9/2000 | Eggers et al. ................ 604/114 |
| 6,126,682 A | 10/2000 | Sharkey et al. |
| 6,142,992 A | 11/2000 | Cheng et al. |
| 6,149,620 A | 11/2000 | Baker et al. |
| 6,159,194 A | 12/2000 | Eggers et al. |
| 6,159,208 A | 12/2000 | Hovda et al. |
| 6,168,593 B1 | 1/2001 | Sharkey et al. |
| 6,179,824 B1 | 1/2001 | Eggers et al. |
| 6,179,836 B1 | 1/2001 | Eggers et al. |
| 6,183,469 B1 | 2/2001 | Thapliyal et al. |
| 6,190,381 B1 | 2/2001 | Olsen et al. |
| 6,203,542 B1 | 3/2001 | Ellsberry et al. |
| 6,210,402 B1 | 4/2001 | Olsen et al. |
| 6,224,592 B1 | 5/2001 | Eggers et al. |
| 6,228,081 B1 | 5/2001 | Goble |
| 6,235,020 B1 | 5/2001 | Cheng et al. |
| 6,238,391 B1 | 5/2001 | Olsen et al. |
| 6,254,600 B1 | 7/2001 | Willink et al. |
| 6,261,286 B1 | 7/2001 | Goble et al. |
| 6,264,652 B1 | 7/2001 | Eggers et al. |
| 6,277,112 B1 | 8/2001 | Underwood et al. |
| 6,277,116 B1 | 8/2001 | Utely et al. |
| 6,293,942 B1 | 9/2001 | Goble et al. |
| 6,296,636 B1 | 10/2001 | Cheng et al. |
| 6,296,638 B1 | 10/2001 | Davison et al. |
| 6,306,134 B1 | 10/2001 | Goble et al. |
| 6,309,387 B1 * | 10/2001 | Eggers et al. ................. 606/41 |
| 6,312,408 B1 | 11/2001 | Eggers et al. |
| 6,322,549 B1 | 11/2001 | Eggers et al. |
| 6,355,032 B1 | 3/2002 | Hovda et al. |
| 6,363,937 B1 | 4/2002 | Hovda et al. |
| 6,379,351 B1 | 4/2002 | Thapliyal et al. |
| 6,383,184 B1 * | 5/2002 | Sharkey ....................... 606/41 |
| 6,391,023 B1 * | 5/2002 | Weber et al. ................. 606/15 |
| 6,391,025 B1 | 5/2002 | Weinstein et al. |
| 6,416,507 B1 | 7/2002 | Eggers et al. |
| 6,416,508 B1 | 7/2002 | Eggers et al. |
| 6,432,103 B1 | 8/2002 | Ellsberry et al. |
| 6,461,350 B1 * | 10/2002 | Underwood et al. .......... 606/32 |
| 6,468,274 B1 | 10/2002 | Alleyne et al. |
| 6,530,922 B2 | 3/2003 | Cosman |
| 6,602,248 B1 | 8/2003 | Sharps et al. |
| 6,632,193 B1 | 10/2003 | Davison et al. |
| 6,632,220 B1 | 10/2003 | Eggers et al. |
| 2002/0029036 A1 | 3/2002 | Goble et al. |
| 2002/0120260 A1 | 8/2002 | Morris et al. |

FOREIGN PATENT DOCUMENTS

| | | | |
|---|---|---|---|
| EP | 0 740 926 A2 | 11/1996 | ........... A61B/17/39 |
| EP | 0 754 437 | 1/1997 | ........... A61B/17/39 |
| EP | 0 515 867 | 7/1999 | |
| EP | 0 694 290 | 11/2000 | ........... A61B/18/04 |
| FR | 2313949 | 1/1977 | ............ A61N/3/02 |
| GB | 2 308 979 | 7/1997 | ........... A61B/17/36 |
| GB | 2 308 980 | 7/1997 | ........... A61B/17/36 |
| GB | 2 308 981 | 7/1997 | ........... A61B/17/36 |
| GB | 2 327 350 | 1/1999 | ........... A61B/17/39 |
| GB | 2 327 351 | 1/1999 | ........... A61B/17/39 |
| GB | 2 327 352 | 1/1999 | ........... A61B/17/39 |
| JP | 57-57802 | 4/1982 | ............. A61B/1/00 |
| JP | 57-117843 | 7/1982 | ........... A61B/17/39 |
| WO | 90/03152 | 4/1990 | ........... A61B/17/39 |
| WO | 90/07303 | 7/1990 | ........... A61B/17/39 |
| WO | 91/13650 | 9/1991 | |
| WO | 92/21278 | 12/1992 | ............. A61B/5/04 |
| WO | 93/13816 | 7/1993 | ........... A61B/17/36 |
| WO | 93/20747 | 10/1993 | ............. A61B/5/00 |
| WO | 94/04220 | 3/1994 | |
| WO | 94/08654 | 4/1994 | .......... A61M/37/00 |
| WO | 94/14383 | 7/1994 | |
| WO | 95/34259 | 12/1995 | ............. A61F/5/48 |
| WO | 96/00042 | 1/1996 | ........... A61B/17/39 |
| WO | 96/34568 | 11/1996 | |
| WO | 97/00646 | 1/1997 | ........... A61B/17/39 |
| WO | 97/00647 | 1/1997 | ........... A61B/17/39 |
| WO | 97/15238 | 5/1997 | |
| WO | 97/24073 | 7/1997 | ........... A61B/17/39 |
| WO | 97/24074 | 7/1997 | ........... A61B/17/39 |
| WO | 97/24992 | 7/1997 | |
| WO | 97/24993 | 7/1997 | |
| WO | 97/24994 | 7/1997 | ........... A61B/17/39 |
| WO | 97/48345 | 12/1997 | ........... A61B/17/39 |
| WO | 97/48346 | 12/1997 | ........... A61B/17/39 |
| WO | 98/07468 | 2/1998 | ............. A61N/1/40 |
| WO | 98/11944 | 3/1998 | |
| WO | 98/27879 | 7/1998 | ........... A61B/17/36 |

| | | | |
|---|---|---|---|
| WO | 98/27880 | 7/1998 | ........... A61B/17/39 |
| WO | 98/44968 | 10/1998 | |
| WO | 99/51155 | 10/1999 | ........... A61B/17/36 |
| WO | 99/51158 | 10/1999 | ........... A61B/17/39 |

OTHER PUBLICATIONS

R. Tucker et al., Abstract P14–11, p. 248, "A Bipolar Electrosurgical Turp Loop".
R. Tucker et al. *J. of Urology* vol. 141, pp. 662–665, (1989).
R. Tucker et al. *Urological Research* vol. 18, pp. 291–294 (1990).
Kramolowsky et al. *J. of Urology* vol. 143, pp. 275–277 (1990).
Kramolowsky et al. *J. of Urology* vol. 146, pp. 669–674 (1991).
Slager et al. *Z. Kardiol.* 76:Suppl. 6, 67–71 (1987).
Slager et al. *JACC* 5(6):1382–6 (1985).
Olsen MD, Bipolar Laparoscopic Cholecstectomy Lecture (marked confidential), Oct. 7, 1991.
Codman & Shurtleff, Inc. "The Malis Bipolar Electrosurgical System CMC–III Instruction Manual" Jul. 1991.
Valley Forge's New Products, CLINICA, 475, 5, Nov. 6, 1991.
Valley Forge Scientific Corp., "Summary of Safety and Effective Information from 510K," 1991.
Codman & Shurtleff, Inc. "The Malis Bipolar Coagulating and Bipolar Cutting System CMC–II" brochure, early 1991.
L. Malis, "The Value of Irrigation During Bipolar Coagulation" See ARTC 21602, early Apr. 9, 1993.
L. Malis, "Excerpted from a seminar by Leonard I. Malis, M.D. at the 1995 American Association of Neurological Surgeons Meeting," 1995.
L. Malis, "Electrosurgery, Technical Note," *J. Neursurg.*, vol. 85, 970–975, Nov. 1996.
Ian E. Shuman, "Bipolar Versus Monopolar Electrosurgery: Clinical Applications," *Dentistry Today*, vol. 20, No. 12, Dec. 2001.
Cook and Webster, "Therapeutic Medical Devices: Application and Design," 1982 .

Valleylab SSE2L Instruction Manual, Jan. 6, 1983.
Robert D. Tucker et al., "Demodulated Low Frequency Currents from Electrosurgical Procedures," *Surgery, Gynecology and Obstetrics*, 159:39–43, 1984.
Selikowitz & LaCourse, "Electric Current and Voltage Recordings on the Myocardium During Electrosurgical Procedures in Canines," *Surgery, Gynecology & Obstetrics*, vol. 164, 219–224, Mar. 1987.
Arnaud Wattiez et al., "Electrosurgery in Operative Endoscopy," Electrosurgical Effects, Blackwell Science, pp. 85–93, 1995.
Leslie A. Geddes, "Medical Device Accidents: With Illustrative Cases" CRC Press, 1998.
C.P. Swain, et al., *Gut* vol. 25, pp. 1424–1431 (1984).
Piercey et al., *Gastroenterology* vol. 74(3), pp. 527–534 (1978).
A.K. Dobbie *Bio–Medical Engineering* vol. 4, pp. 206–216 (1969).
B. Lee et al. JACC vol. 13(5), pp. 1167–1175 (1989).
K. Barry et al. *American Heart Journal* vol. 117, pp. 332–341 (1982).
W. Honig *IEEE* pp. 58–65 (1975).
Jacob Kline, *Handbook of Biomedical Engineering*, Academic Press Inc., N.Y., pp. 98–113, 1988.
Letter from Department of Health to Jerry Malis dated Apr. 15, 1985.
Letter from Jerry Malis to FDA dated Jul. 25, 1985.
Letter from Department of Health to Jerry Malis dated Apr. 22, 1991.
Leonard Malis, "Instrumenation for Microvascular Neurosurgery" *Cerebrovascular Surgery*, vol. 1, 245–260, 1985.
Valleylab, Inc. "Valleylab Part No. 945 100 102 A" Surgistat Service Manual, Jul. 1988.
Leonard I. Malis, "New Trends in Microsurgery and Applied Technology," *Advanced Technology in Neurosurgery*, 1–16, 1988.

* cited by examiner

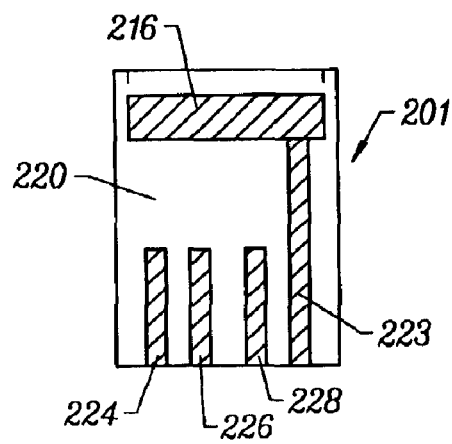
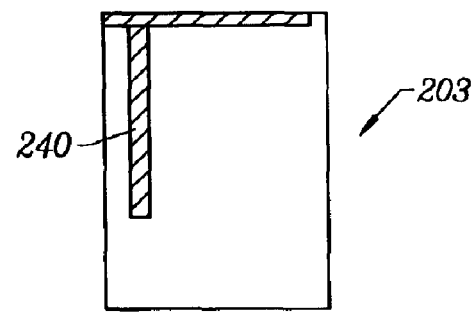
FIG. 9A　　　　　　　　FIG. 10A
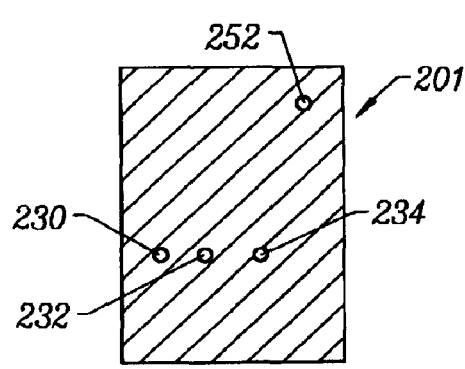
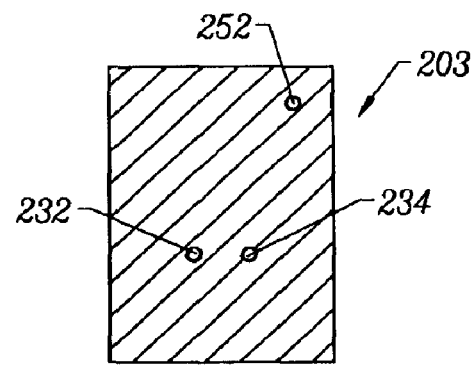
FIG. 9B　　　　　　　　FIG. 10B

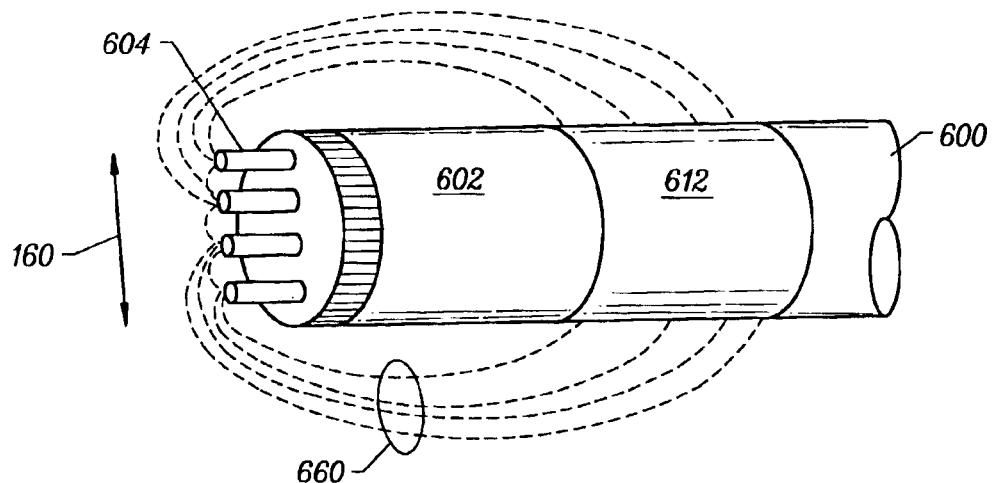
FIG. 27
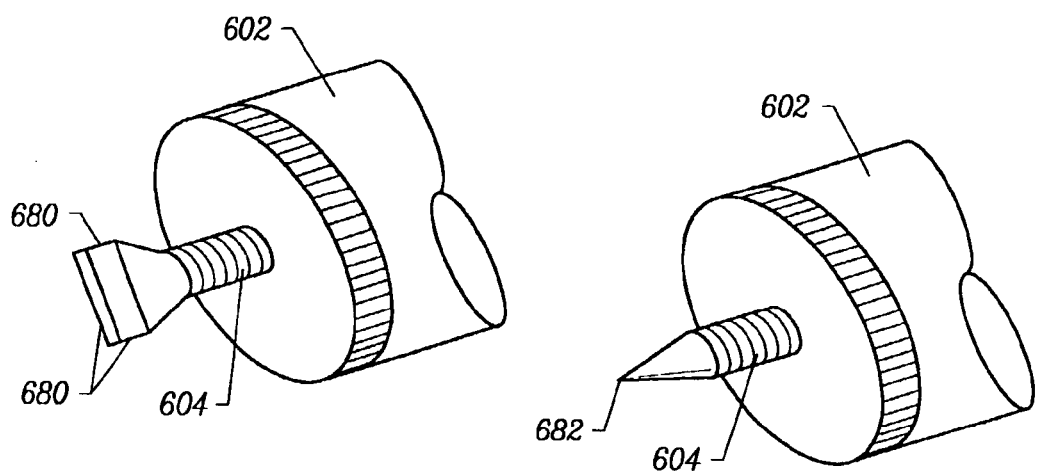
FIG. 28
FIG. 29

METHODS AND APPARATUS FOR SKIN TREATMENT

RELATED APPLICATIONS

The present invention is a non-provisional of U.S. Provisional No. 60/337,496 filed Nov. 8, 2001, the entirety of which is incorporated by reference.

BACKGROUND OF THE INVENTION

The present invention relates generally to the field of electrosurgery, and more particularly to surgical devices and methods which employ high frequency electrical energy to remove fatty tissue. The present invention also relates to methods and apparatus for electrosurgical treatment of skin for contraction of collagen fibers within the skin. The present invention also relates to methods and apparatus for electrosurgical induction of collagen deposition in the dermis.

Suction lipectomy, commonly known as liposuction or lipoxheresis, is a well known surgical procedure used for sculpturing or contouring the human body to increase the attractiveness of its form. In general, the procedure involves the use of a special type of curette or cannula which is coupled to an external source of suction. An incision is made in the target area and the fatty tissue is essentially vacuumed from the patient's body. This procedures has its disadvantages, however, because the fat is relatively difficult to separate from the surrounding tissue. Such separation often causes excessive bleeding and damage to adjacent tissue or muscles. A further problem is that the surgeon must be careful not to allow the suction to remove or injure any desirable tissues, such as muscle, blood vessels, skin, subcutaneous tissues and the like. In addition, it is often difficult to maintain constant suction without stopping to clean tissue fragments from the cannula. Normally, the surgeon attempts to compensate for this problem by rapidly moving the cannula within the cavity, and even periodically withdrawing it to allow the fat to move through the cannula. This causes further trauma and collateral damage to surrounding muscle, tissue and other body structures.

In an effort to resolve some of the drawbacks with conventional liposuction, ultrasonic probes for vibrating and aspirating adipose tissue have been developed. The ultrasonic vibrations physically melt the fatty tissue so that it can be emulsified and aspirated through the probe. These ultrasonic probes have reduced the physical exertion required by the surgeon to remove fatty tissue, increased the speed of the operation and reduced the collateral damage created at the incision point. One problem with these probes, however, is excess heat generation at the distal tip of the ultrasonic probe. For example, when the probe has been inserted into the fatty tissue near the skin or the peritoneum, resistance can be met, which increases the wattage at the tip of the probe. The heat generated at the tip of the probe from the increased wattage may be in excess of the heat required for melting the fatty tissue. This excess heat results in burning of tissue, collateral damage to muscles or blood vessels and even penetration of membranes such as the skin or the peritoneum.

RF energy has also been used in liposuction procedures to remove fatty tissue. In particular, microwave and monopolar RF devices have been used to heat and soften fatty tissue so that the tissue can be more readily detached from the adjacent tissue with a suction instrument. Similar to ultrasonic energy, however, current microwave and monopolar RF devices have difficulty controlling excess heat generation at the target site, resulting in undesirable collateral tissue damage. For example, conventional electrosurgical cutting devices typically operate by creating a voltage difference between the active electrode and the target tissue, causing an electrical arc to form across the physical gap between the electrode and tissue. At the point of contact of the electric arcs with tissue, rapid tissue heating occurs due to high current density between the electrode and tissue. This high current density causes cellular fluids to rapidly vaporize into steam, thereby producing a "cutting effect" along the pathway of localized tissue heating. This cutting effect generally results in the production of smoke, or an electrosurgical plume, which can spread bacterial or viral particles from the tissue to the surgical team or to other portions of the patient's body. In addition, the tissue is parted along the pathway of evaporated cellular fluid, inducing undesirable collateral tissue damage in regions surrounding the target tissue site.

Moreover, monopolar electrosurgery methods generally direct electric current along a defined path from the exposed or active electrode through the patient's body to the return electrode, which is externally attached to a suitable location on the patient's skin. In addition, since the defined path through the patient's body has a relatively high electrical impedance, large voltages must typically be applied between the active and return electrodes to generate a current suitable for cutting or coagulation of the target tissue. This current, however, may inadvertently flow along localized pathways in the body having less impedance than the defined electrical path. This situation will substantially increase the current flowing through these paths, possibly causing damage to or destroying tissue along and surrounding this pathway.

The skin is the largest organ of the human body, having a weight of approximately six pounds in the adult. The skin has important functions, including: protection from injury and infection; regulation of body temperature; and storage of fat, water, and vitamin D. The skin has a layered structure comprising the outer epidermis, the dermis, and the inner subcutis. The epidermis is a relatively thin layer. The dermis is a relatively thick layer containing the protein collagen, which provides strength and resilience to the skin. The subcutis lies below the dermis and consists of a network of collagen and fat cells.

Following an electrosurgical or conventional liposuction procedure, a pocket may be formed beneath the skin whence adipose tissue was removed, wherein the pocket is overlaid by an excessive area of skin or by a region of excessively loose skin. There is a need for apparatus and methods for treating the skin in a region having undergone liposuction, for the purpose of shrinking and/or tightening the skin in that region. There is a further need for shrinking and tightening the skin following or during face-lift and neck-lift cosmetic procedures. There is also a need for apparatus and methods for electrosurgically treating the skin in order to reduce or remove unwanted wrinkles in the skin.

SUMMARY OF THE INVENTION

The present invention provides systems, apparatus and methods for selectively applying electrical energy and suction to fatty or adipose tissue to remove the adipose tissue from the patient (e.g., liposuction, abdominoplasty and the like). The present invention provides apparatus and methods for performing cosmetic procedures for the rejuvenation of the skin.

In one aspect of the invention, a method for removing adipose or fatty tissue underlying a patient's epidermis in body regions, such as the abdomen, lower torso, thighs, face and neck, is disclosed. This method includes positioning one or more active electrode(s) and one or more return electrode(s) in close proximity to a target region of fatty tissue. A high frequency voltage is applied between the active and return electrodes, and the fatty tissue or fragments of the fatty tissue are aspirated from the target region. The high frequency voltage either heats and softens or separates the fatty tissue or completely removes at least a portion of the tissue. In both embodiments, the remaining fatty tissue is more readily detached from the adjacent tissue in the absence of energy, and less mechanical force is required for removal. The bipolar configuration of the present invention controls the flow of current to the immediate region around the distal end of the probe, which minimizes tissue necrosis and the conduction of current through the patient. The residual heat from the electrical energy also provides simultaneous hemostasis of severed blood vessels, which increases visualization and improves recovery time for the patient. The techniques of the present invention produce significantly less thermal energy than many conventional techniques, such as conventional ultrasonic and RF devices, which reduces collateral tissue damage and minimizes pain and postoperative scarring.

In one embodiment, the method comprises introducing a distal end of an electrosurgical instrument, such as a probe or a catheter, to the target site, and aspirating fatty tissue from the target site through one or more aspiration lumen(s) in the instrument. High frequency voltage is applied between one or more aspiration electrode(s) coupled to the aspiration lumen(s) and one or more return electrode(s) so that an electric current flows therebetween. The high frequency voltage is sufficient to remove or at least soften a portion of the tissue before the tissue passes into the aspiration lumen(s). This partial or total ablation reduces the size of the aspirated tissue fragments to inhibit clogging of the aspiration lumen.

In an exemplary embodiment, the tissue may be removed and/or softened by an electrosurgical probe having an aspiration lumen and one or more aspiration electrode(s) to prevent clogging of the lumen. The aspiration electrode(s) are usually located near or at the distal opening of the aspiration lumen so that tissue can be partially ablated before it becomes clogged in the aspiration lumen. In some embodiments, the aspiration electrodes(s) are adjacent to the distal opening, or they may extend across the distal opening of the lumen. The latter configuration has the advantage of ensuring that the fatty tissue passing through the aspiration lumen will contact the aspiration electrode(s). In other embodiments, the aspiration electrode(s) may be positioned within the aspiration lumen just proximal of the distal opening. This embodiment has the advantage of eliminating any possibility of contact between the surrounding tissue and the return electrode. The aspiration electrode(s) may comprise a loop, a coiled structure, a hook, or any other geometry suitable for ablating the aspirated tissue. In one representative embodiment, the electrosurgical probe comprises a pair of loop electrodes disposed across the distal end of the suction lumen. A more complete description of such a device can be found in Ser. No. 09/010,382, filed Jan. 21, 1998, previously incorporated herein by reference.

The electrosurgical probe will preferably also include one or more ablation electrode(s) for ablating or softening fatty tissue at the target site prior to aspiration of the remaining tissue fragments from the patient's body. Typically, the ablation electrode(s) are different from the aspiration electrode(s), although the same electrodes may serve both functions. In an exemplary embodiment, the probe includes a plurality of electrically isolated electrode terminals surrounding the distal opening of the aspiration lumen. High frequency voltage is applied between the electrode terminals and a return electrode to ablate or soften the fatty tissue at the target site. The non-ablated tissue fragments are then aspirated from the target site. Preferably, one or more of the electrode terminals are loop electrodes that extend across the distal opening of the suction lumen to ablate, or at least reduce the volume of, the tissue fragments, thereby inhibiting clogging of the lumen. The aspiration or loop electrodes may be energized with the active electrode terminal(s), or they may be isolated from the electrode terminal(s) so that the surgeon may select which electrodes are activated during the procedure.

In some embodiments, the return electrode(s) comprises an annular electrode member on the probe itself, spaced proximally from the aspiration and ablation electrodes. In these embodiments, electrically conductive fluid, such as isotonic saline, is preferably used to generate a current flow path between the aspiration and active electrode(s) and the return electrode(s). High frequency voltage is then applied between the aspiration and active electrode(s) and the return electrode(s) through the current flow path created by the electrically conductive fluid. Depending on the procedure, the electrically conductive fluid may be delivered to the target site through, for example, a fluid lumen in the probe or a separate instrument, or the fluid may already be present at the target site, as is the case in many arthroscopic procedures.

The return electrode(s) are preferably spaced from the active electrode(s) a sufficient distance to prevent arcing therebetween at the voltages suitable for tissue removal, and to prevent contact of the return electrode(s) with the target tissue. The current flow path between the active and return electrodes may be generated by directing an electrically conductive fluid along a fluid path past the return electrode and to the target site, or by locating a viscous electrically conductive fluid, such as a gel, at the target site, and submersing the active and return electrode(s) within the conductive gel. The electrically conductive fluid will be selected to have sufficient electrical conductivity to allow current to pass therethrough from the active to the return electrode, and such that the fluid ionizes into a plasma when subject to sufficient electrical energy, as discussed below. In the exemplary embodiment, the conductive fluid is isotonic saline, although other fluids may be selected, as described in co-pending Provisional Patent Application No. 60/098,122, filed Aug. 27, 1998, the complete disclosure of which is incorporated herein by reference.

In the exemplary embodiment, the adipose tissue is removed with molecular dissociation or disintegration processes. Conventional electrosurgery cuts through tissue by rapidly heating the tissue until cellular fluids explode, producing a cutting effect along the pathway of localized heating. The present invention volumetrically removes the tissue along the cutting pathway in a cool ablation process that minimizes thermal damage to surrounding tissue. In these processes, the high frequency voltage applied to the active electrode(s) is sufficient to vaporize an electrically conductive fluid (e.g., gel or saline) between the electrode(s) and the tissue. Within the vaporized fluid, a plasma is formed and charged particles (e.g., electrons) are accelerated towards the tissue to cause the molecular breakdown or disintegration of several cell layers of the tissue. This molecular dissociation is accompanied by the volumetric removal of the tissue. The ablation of target tissue by this process can be precisely controlled, thereby avoiding or minimizing damage to non-target tissue. This process can be precisely controlled to effect the volumetric removal of tissue as thin as 10 to 50 microns with minimal heating of, or damage to, surrounding or underlying tissue structures. A more complete description of this phenomena is described in commonly assigned U.S. Pat. No. 5,683,366, the complete disclosure of which is incorporated herein by reference.

The present invention offers a number of advantages over prior art RF, ultrasonic, microwave and laser techniques for removing or softening tissue. The ability to precisely control the volumetric removal of tissue results in a field of tissue removal that is very defined, consistent, and predictable. This precise heating also helps to minimize or completely eliminate damage to healthy tissue structures or nerves that are often adjacent to the target tissue. In addition, small blood vessels within the skin tissue are simultaneously cauterized and sealed as the tissue is removed to continuously maintain hemostasis during the procedure. This increases the surgeon's field of view, and shortens the length of the procedure. Moreover, since the present invention allows for the use of electrically conductive fluid (contrary to prior art bipolar and monopolar electrosurgery techniques), isotonic saline may be used during the procedure. Saline is the preferred medium for irrigation because it has the same concentration as the body's fluids and, therefore, is not absorbed into the body as much as other fluids.

In one aspect, the invention provides a method for improving the appearance of skin on the face and neck using an electrosurgical probe. Typically, the probe includes a shaft having a shaft distal end, an active electrode at the shaft distal end, and a return electrode spaced from the active electrode. In one embodiment, the method involves shrinking the skin at a target site of the patient's face or neck following a face-lift or neck-lift procedure. In one embodiment, the probe is adapted for penetrating the skin such that the shaft distal end is positioned at a subcutaneous location, and the method involves accessing the patient's dermis from the subcutaneous location. The active electrode is positioned within the dermis at the target site, and a high frequency voltage is applied between the active electrode and the return electrode in the sub-ablation mode, wherein the applied voltage effects contraction of the skin in the vicinity of the target site. Typically, the sub-ablation voltage is in the range of from about 20 volts RMS to 90 volts RMS. Optionally, the method may further involve removing excess tissue, such as adipose tissue or excessively loose skin, from the patient's face or neck prior to electrosurgically shrinking the skin. The excess tissue may be removed using conventional apparatus, or by the application of a high frequency voltage in the ablation mode, wherein the ablation level voltage is sufficient to cut the skin or volumetrically remove excess or unwanted tissue.

In another aspect, the invention provides a method for removing or reducing wrinkles on the skin of a patient. Typically, the method involves the use of an electrosurgical probe comprising a shaft having a shaft distal end, an active electrode at the shaft distal end, and a return electrode spaced from the active electrode. The method further involves positioning the active electrode within the dermis at the location of a wrinkle targeted for treatment. In one embodiment, positioning the active electrode in the dermis involves directly accessing the dermis by advancing the shaft distal end through the epidermis toward the dermis until the active electrode lies within the dermis. In an alternative embodiment, positioning the active electrode in the dermis involves advancing the shaft distal end in a first direction from the epidermis toward the subcutis until the shaft distal end has reached a subcutaneous location, and thereafter advancing the shaft distal end in a second direction from the subcutaneous location toward the epidermis until the active electrode lies within the dermis. That is to say, in the latter embodiment the active electrode is positioned within the dermis by subcutaneously accessing the dermal layer of the skin. In one aspect of the invention, the shaft distal end is at least somewhat flexible, and the probe is adapted for interconversion between a linear configuration and a curved configuration. The shaft distal end may be selectively deflectable (steerable) during a procedure, or may be pre-bent to a desired extent prior to performing a procedure.

Once the active electrode has been positioned within the dermis at the location of the target wrinkle, a sub-ablation voltage is applied between the active electrode and the return electrode, wherein the sub-ablation voltage is sufficient to induce localized collagen deposition. Such collagen deposition at the location of the wrinkle causes the wrinkle to be less noticeable (reduced) or essentially disappear (removed). Prior to or during application of the voltage, an electrically conductive fluid may be delivered to the working end of the probe to provide a current flow path between the active electrode and the return electrode. Typically, wrinkles targeted for treatment are on the face or neck, often being around the eyes or around the mouth.

According to another aspect of the invention, there is provided a method for treating the skin of a patient, in conjunction with a lipectomy procedure, using an electrosurgical probe. Typically, the probe includes a shaft having a shaft distal end, an active electrode disposed at the shaft distal end, and a return electrode spaced from the active electrode. In one embodiment, the skin is treated electrosurgically in order to shrink and/or tighten the skin in the region of the liposuction procedure. The active electrode is positioned in at least close proximity to the dermis in the region of the liposuction, and a high frequency sub-ablation voltage is applied between the active electrode and the return electrode, wherein the sub-ablation voltage is effective in shrinking the skin due to the controlled heating of collagen fibers in the dermis. Typically, the electrosurgical treatment (e.g., the voltage parameters) is selected to heat the dermis to a temperature in the range from about 60° C. to 70° C., which is a suitable temperature range for effecting shrinkage of mammalian collagen, as described hereinbelow. In one embodiment, the active electrode comprises a material such as tungsten, stainless steel, gold, platinum, titanium, molybdenum, nickel, or their alloys, and the like.

In another embodiment of the invention, there is provided a method for performing a face-lift or a neck-lift procedure on a patient, using an electrosurgical instrument. Typically, the instrument includes a shaft having a shaft distal end, an electrically insulating electrode support at the shaft distal end, an active electrode mounted in the electrode support, and a return electrode spaced from the active electrode. In one embodiment, the method involves accessing the patient's dermis by advancing the shaft distal end from a subcutaneous location (i.e., from the underside of the skin), so that the active electrode is positioned within the dermis or subcutis at a target site. Once the active electrode is so positioned, a high frequency voltage is applied between the active electrode and the return electrode in the sub-ablation mode, wherein the voltage effects contraction of the skin in the vicinity of the active electrode. The active electrode may be moved over the underside of the skin during application of the high frequency voltage, in order to contract collagen fibers over a relatively large area of the dermis. Optionally, excess skin tissue or adipose tissue may be selectively removed from one or more regions of the face or neck prior to shrinking the skin. In one embodiment, the electrode support and the active electrode are arranged laterally on the shaft distal end to facilitate access to the target site during certain procedures.

In another aspect of the invention there is provided an electrosurgical instrument for treating the skin of a patient. The instrument generally comprises a shaft having a shaft distal end and a shaft proximal end, and an electrode assembly disposed at the shaft distal end. The shaft distal end is adapted for penetrating the skin to a subcutaneous location. As an example, the shaft may comprise a narrow diameter stainless steel rod, e.g., having dimensions similar to those of a hypodermic needle. The electrode assembly comprises an electrically insulating electrode support, an active electrode terminal on the electrode support, and a return electrode disposed proximal to the active electrode terminal. In one embodiment, the shaft distal end is adapted for transformation (or interconversion) between a linear configuration, adapted for penetrating the skin to a subcutaneous location, and a curved configuration, adapted for guiding the active electrode from the subcutaneous location to a target location within the dermis.

A further understanding of the nature and advantages of the invention will become apparent by reference to the remaining portions of the specification and drawings.

BRIEF DESCRIPTION OF THE DRAWINGS

FIGS. 9A, 10A, 11A, 12A, and 13 are side views of the individual wafer layers of the electrode support;

FIGS. 9B, 10B, 11B, and 12B are cross-sectional views of the individual wafer layers;

FIG. 27 is a detailed end view of an electrosurgical probe having an elongate, linear array of electrode terminals suitable for use in surgical cutting;

FIG. 28 is a detailed view of a single electrode terminal having a flattened end at its distal tip;

FIG. 29 is a detailed view of a single electrode terminal having a pointed end at its distal tip;

DESCRIPTION OF SPECIFIC EMBODIMENTS

Figure 1:
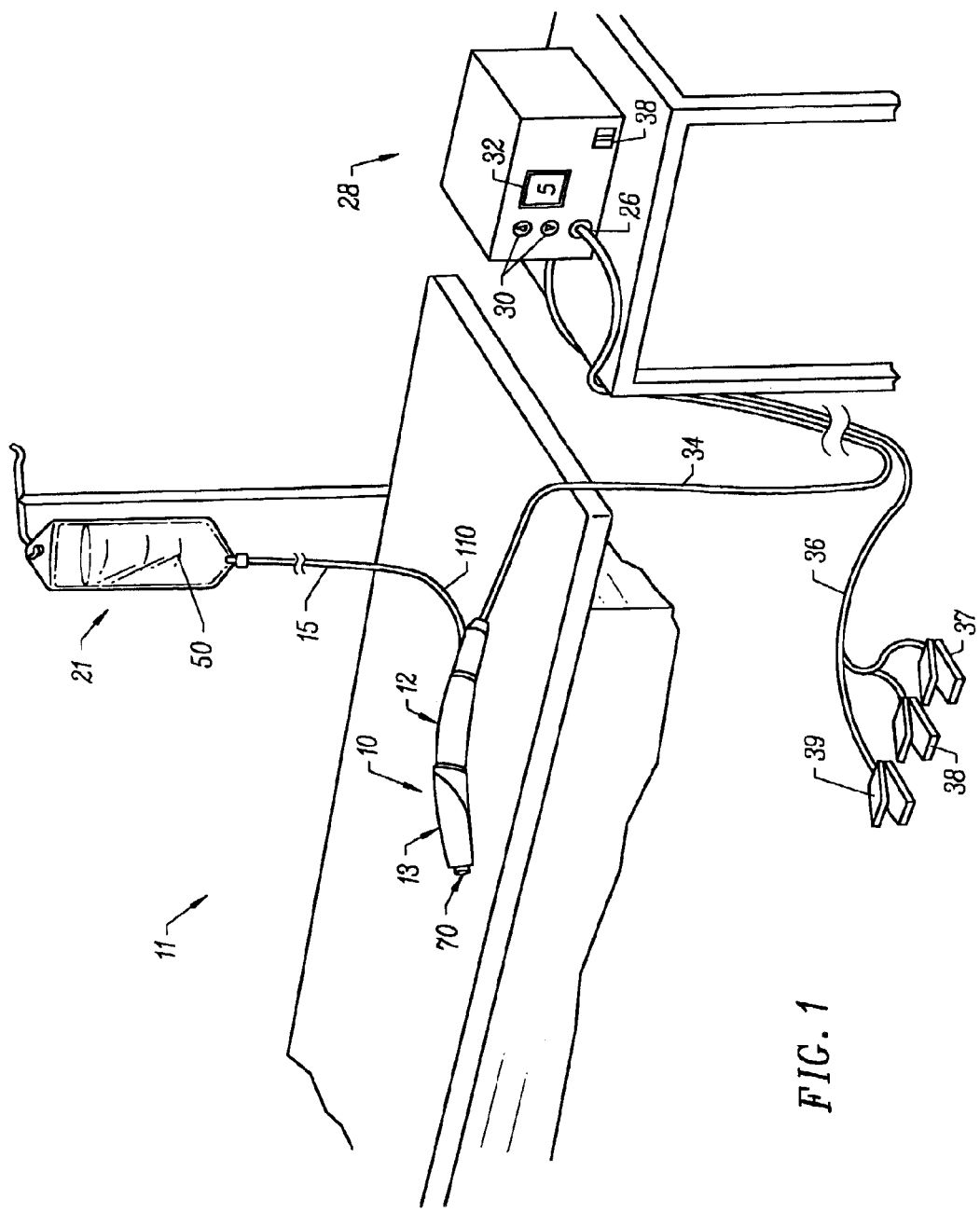
FIG. 1 is a perspective view of an electrosurgical system for treating a patient's skin including an electrosurgical generator and an electrosurgical probe or handpiece.

The present invention provides systems and methods for selectively applying energy to a target location within or on a patient's body, particularly including procedures on an external body surface, such as epidermal and dermal tissues in the skin, or the underlying subcutaneous tissue. The present invention also provides methods and apparatus for removing fatty or adipose tissue underlying the epidermal and dermal layers of the skin, such as liposuction, abdominoplasties, or other lipectomy procedures. The present invention also relates to procedures for skin tissue cutting, ablation, incising or removal in the epidermis or dermis, e.g., the removal of pigmentations, vascular lesions (e.g., leg veins), scars, tattoos, etc., and for other surgical procedures on the skin, such as tissue rejuvenation, skin shrinkage, blepharoplasty, browlifts, cosmetic surgery, wrinkle removal, face-lifts and neck-lifts, as well as hair removal and/or hair transplant procedures. The present invention is also concerned with shrinkage of skin by electrosurgical treatment of the underside of the skin, e.g., at the site of a liposuction or face-lift procedure. In addition, the systems and methods can be applied equally well to procedures involving other tissues of the body, as well as to other procedures including open surgery, arthroscopic surgery, laparoscopic surgery, thoracoscopic surgery, and other endoscopic surgical procedures.

In one embodiment, the present invention applies high frequency (RF) electrical energy to one or more electrode terminals underlying an external body surface, such as the outer surface of the skin, to soften and/or ablate fatty tissue in order to aspirate the fatty tissue from the patient's body. Depending on the specific procedure, the present invention may be used to: (1) volumetrically remove the fatty tissue (i.e., ablate or effect molecular dissociation of adipose tissue); (2) decouple or soften fatty tissue from adjacent tissue so that the fatty tissue can be more easily aspirated; (3) shrink and tighten the skin by controlled heating of the dermis; (4) induce localized collagen deposition in the dermis to reduce or remove skin wrinkles; (5) shrink or contract collagen-containing connective tissue; and/or (6) coagulate blood vessels underlying the surface of the skin.

In one embodiment, the present invention applies high frequency (RF) electrical energy to one or more electrode terminals underlying, within, or adjacent to the skin, in order to contract collagen fibers within the dermis. The RF energy heats the tissue in a controlled manner, either directly by virtue of the electrical current flowing therethrough, or indirectly by exposing the tissue to fluid heated by the RF energy, to elevate the tissue temperature from normal body temperatures (e.g., 37° C.) to a temperature in the range of from about 45° C. to 90° C., and preferably in the range of from about 60° C. to 70° C.

Thermal shrinkage of mammalian collagen occurs within a temperature range of from about 60° C. to 70° C. (Deak, G., et al., "The Thermal Shrinkage Process of Collagen Fibres as Revealed by Polarization Optical Analysis of Topooptical Staining Reactions," Acta Morphologica Acad. Sci. of Hungary, Vol. 15(2), pp 195–208, 1967). While not being bound by theory, previously reported research has attributed thermal shrinkage of collagen to the cleaving of the internal stabilizing cross-linkages within the collagen matrix (Deak, G., et al., ibid.). It has also been reported that when collagen is exposed to a temperature above 70° C., the collagen matrix begins to relax again, and the shrinkage effect is reversed, resulting in no net shrinkage (see, for example, Allain, J. C., et al., "Isometric Tensions Developed During the Hydrothermal Swelling of Rat Skin," Connective Tissue Research, Vol. 7, pp 127–133, 1980). Consequently, the controlled heating of tissue to a precise temperature is critical to the achievement of effective collagen shrinkage. A more detailed description of collagen shrinkage can be found in U.S. Pat. No. 6,159,194.

According to another aspect of the present invention, tissue is ablated or removed through molecular dissociation or disintegration of tissue components (i.e., by breaking the molecular bonds of the tissue components). In this procedure, a high frequency voltage is applied between one or more electrode terminal(s) and one or more return electrode(s) to develop high electric field intensities in the vicinity of the target tissue site. The high electric field intensities lead to electric field induced molecular breakdown of target tissue through molecular dissociation (rather than thermal evaporation or carbonization). Applicant believes that the tissue structure is volumetrically removed through molecular disintegration of larger organic molecules into smaller molecules and/or atoms, such as hydrogen, oxides of carbon, hydrocarbons and nitrogen compounds. This molecular disintegration completely removes the tissue structure, as opposed to dehydrating the tissue material by the removal of liquid within the cells of the tissue, as is typically the case with electrosurgical desiccation and vaporization processes of the prior art.

The high electric field intensities may be generated by applying a high frequency voltage that is sufficient to vaporize an electrically conductive fluid over at least a portion of the electrode terminal(s) in the region between the distal tip of the electrode terminal(s) and the target tissue. The electrically conductive fluid may be a liquid, such as isotonic saline, delivered to the target site, or a viscous fluid, such as a gel, that is located at the target site. In the latter embodiment, the electrode terminal(s) are submersed in the electrically conductive gel during the surgical procedure. Since the vapor layer or vaporized region has a relatively high electrical impedance, it increases the voltage differential between the electrode terminal tip and the tissue and causes ionization within the vapor layer due to the presence of an ionizable species (e.g., sodium when isotonic saline is the electrically conductive fluid). This ionization, under optimal conditions, induces the discharge of energetic electrons and photons from the vapor layer and to the surface of the target tissue. This energy may be in the form of energetic photons (e.g., ultraviolet radiation), energetic particles (e.g., electrons) or a combination thereof. A more detailed description of this phenomenon can be found in commonly assigned U.S. Pat. No. 5,683,366 the complete disclosure of which is incorporated herein by reference.

In the above procedure, it may also be desirable to effect collagen shrinkage or contraction of the tissue layers underlying the epidermal tissue. In these procedures, the temperature of the electrode terminal(s) can be carefully controlled such that sufficient thermal energy is transferred to these underlying layers to contract the collagen connective tissue. The thermal energy may be transferred directly through RF current that passes through and resistively heats the underlying tissue layers, or it may be transferred indirectly by heating the electrically conductive fluid, and allowing the heated fluid to contact the underlying layers after the epidermal layers have been removed. A complete description of suitable methods of contracting collagen tissue with RF energy is described in U.S. Pat. No. 6,159,194, the complete disclosure of which has previously been incorporated herein by reference.

In one method of the present invention, one or more electrode terminals are brought into close proximity to tissue at a target site, and the power supply is activated in the ablation mode such that sufficient voltage is applied between the electrode terminals and the return electrode to volumetrically remove the tissue through molecular dissociation, as described below. During this process, vessels within the tissue will be severed. Smaller vessels will be automatically sealed with the system and method of the present invention. Larger vessels, and those with a higher flow rate, such as arterial vessels, may not be automatically sealed in the ablation mode. In these cases, the severed vessels may be sealed by activating a control (e.g., a foot pedal) to reduce the voltage of the power supply into the coagulation (sub-ablation) mode. In the sub-ablation mode, the electrode terminals may be pressed against the severed vessel to provide sealing and/or coagulation of the vessel. Alternatively, a coagulation electrode located on the same or a different instrument may be pressed against the severed vessel. Once the vessel is adequately sealed, the surgeon activates a control (e.g., another foot pedal) to increase the voltage of the power supply back into the ablation mode.

The present invention is also useful for ablating, cutting or softening tissue around nerves, such as cranial nerves, e.g., facial nerves, vestibulocochlear nerves and the like. One of the significant drawbacks with prior art RF devices and lasers is that these devices do not differentiate between the target tissue and the surrounding nerves or bone. Therefore, the surgeon must be extremely careful during these procedures to avoid damage to the nerves within and around the target site. In the present invention, the Coblation™ process for removing tissue results in extremely small depths of collateral tissue damage as discussed above. This allows the surgeon to remove, soften or cut tissue close to a nerve without causing collateral damage to the nerve fibers.

In addition to the generally precise nature of the novel mechanisms of the present invention, applicant has discovered an additional method of ensuring that adjacent nerves are not damaged during tissue removal. According to the present invention, systems and methods are provided for distinguishing between the fatty tissue immediately surrounding nerve fibers and the normal tissue that is to be removed during the procedure. Nerves usually comprise a connective tissue sheath, or epineurium, enclosing the bundles of nerve fibers, each bundle being surrounded by its own sheath of connective tissue (the perineurium) to protect these nerve fibers. The outer protective tissue sheath or epineurium typically comprises a fatty material having substantially different electrical properties than the normal target tissue, such as collagen-containing connective tissue. The system of the present invention measures the electrical properties of the tissue at the tip of the probe with one or more sensing electrode(s). These electrical properties may include electrical conductivity at one, several, or a range of frequencies (e.g., in the range from 1 kHz to 100 MHz), dielectric constant, capacitance, or combinations of these. In this embodiment, an audible signal may be produced when the sensing electrode(s) at the tip of the probe detects the fatty material surrounding a nerve, or direct feedback control can be provided to only supply power to the electrode terminal(s), either individually or to the complete array of electrodes, if and when the tissue encountered at the tip or working end of the probe is normal tissue based on the measured electrical properties.

In addition to the above, applicant has discovered that the Coblation® mechanism of the present invention can be manipulated to ablate or cut certain tissue structures, while having little effect on other tissue structures. As discussed above, in one aspect the present invention uses a technique of vaporizing electrically conductive fluid to form a plasma layer or pocket around the electrode terminal(s), and then inducing the discharge of energy from this plasma or vapor layer to break the molecular bonds of the tissue structure. Based on initial experiments, applicants believe that the free electrons within the ionized vapor layer are accelerated in the high electric fields near the electrode tip(s). When the density of the vapor layer (or within a bubble formed in the electrically conducting liquid) becomes sufficiently low (i.e., less than approximately $10^{20}$ atoms/cm$^3$ for aqueous solutions), the electron mean free path increases to enable subsequently injected electrons to cause impact ionization within these regions of low density (i.e., vapor layers or bubbles). Energy evolved by the energetic electrons (e.g., 4 to 5 eV) can subsequently bombard a molecule and break its bonds, dissociating a molecule into free radicals, which then combine into final gaseous or liquid species.

The energy evolved by the energetic electrons may be varied by adjusting a variety of factors, such as: the number of electrode terminals; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; and other factors. Accordingly, these factors can be manipulated to control the energy level of the excited electrons. Since different tissue structures have different molecular bonds, the present invention can be configured to break the molecular bonds of certain tissue, while having too low an energy to break the molecular bonds of other tissue. For example, fatty tissue, (e.g., adipose tissue) has double bonds that require a substantially higher energy level than 4 to 5 eV to break. Accordingly, factors such as applied voltage and power may be adjusted such that the target tissue (e.g., adipose tissue, dermal tissue) may be ablated or modified according to a particular procedure. A more complete description of this phenomenon can be found in co-pending U.S. patent application Ser. No. 09/032,375, filed Feb. 27, 1998, the complete disclosure of which is incorporated herein by reference. In one embodiment, the present invention may be used to effectively ablate cells to release the inner fat content in a liquid form.

The present invention also provides systems, apparatus and methods for selectively removing tumors, e.g., facial tumors, or other undesirable body structures while minimizing the spread of viable cells from the tumor. Conventional techniques for removing such tumors generally result in the production of smoke in the surgical setting, termed an electrosurgical or laser plume, which can spread intact, viable bacterial or viral particles from the tumor or lesion to the surgical team or to other portions of the patient's body. This potential spread of viable cells or particles has resulted in increased concerns over the proliferation of certain debilitating and fatal diseases, such as hepatitis, herpes, HIV and papillomavirus. In the present invention, high frequency voltage is applied between the electrode terminal(s) and one or more return electrode(s) to volumetrically remove at least a portion of the tissue cells in the tumor through the dissociation or disintegration of organic molecules into non-viable atoms and molecules. Specifically, the present invention converts the solid tissue and cells into non-condensable gases that are no longer intact or viable, and thus, not capable of spreading viable tumor particles to other portions of the patient's brain or to the surgical staff. The high frequency voltage is preferably selected to effect controlled removal of these tissues and cells, while minimizing substantial tissue necrosis to surrounding or underlying tissue. A more complete description of this phenomenon can be found in co-pending U.S. patent application Ser. No. 09/109,219, filed Jun. 30, 1998, the complete disclosure of which is incorporated herein by reference The electrosurgical instrument will comprise a shaft or a handpiece having a proximal end and a distal end which supports one or more electrode terminal(s). The shaft or handpiece may assume a wide variety of configurations, with the primary purpose being to mechanically support the active electrode and permit the treating physician to manipulate the electrode from a proximal end of the shaft. For dermatology procedures, the shaft will have any suitable length and diameter that would facilitate handling the instrument by the surgeon. For lipectomy procedures, the shaft will preferably have a distal end suitable for delivery through a percutaneous penetration in the patient's skin.

The present invention may use a single active electrode terminal or an electrode array distributed over a contact surface of an instrument. In the latter embodiment, the electrode array usually includes a plurality of independently current-limited and/or power-controlled electrode terminals to apply electrical energy selectively to the target tissue while limiting the unwanted application of electrical energy to the surrounding tissue and environment resulting from power dissipation into surrounding electrically conductive liquids, such as blood, normal saline, electrically conductive gel, and the like. The electrode terminals may be independently current-limited by isolating the terminals from each other and connecting each terminal to a separate power source that is isolated from the other electrode terminals. Alternatively, the electrode terminals may be connected to each other at either the proximal or distal ends of the probe to form a single wire that couples to a power source.

The electrode terminal(s) are preferably supported within or by an inorganic insulating support positioned near the distal end of the instrument shaft. The return electrode may be located on the instrument shaft, on another instrument, or on the external surface of the patient (i.e., a dispersive pad). The close proximity of nerves and other sensitive tissue in the face, however, makes a bipolar design more preferable because this minimizes the current flow through healthy tissue and surrounding nerves. Accordingly, the return electrode is preferably either integrated with the instrument body, or another instrument located in close proximity to the distal end of the instrument. The proximal end of the instrument will include the appropriate electrical connections for coupling the return electrode(s) and the electrode terminal(s) to a high frequency power supply, such as an electrosurgical generator.

The current flow path between the electrode terminals and the return electrode(s) may be generated by submerging the tissue site in an electrical conducting fluid (e.g., within a viscous fluid, such as an electrically conductive gel) or by directing an electrically conductive fluid along a fluid path to the target site (i.e., a liquid, such as isotonic saline, or a gas, such as argon). The conductive gel may also be delivered to the target site to achieve a slower more controlled delivery rate of conductive fluid. In addition, the viscous nature of the gel may allow the surgeon to more easily contain the gel around the target site (e.g., rather than attempting to contain isotonic saline). A more complete description of an exemplary method of directing electrically conductive fluid between the active and return electrodes is described in U.S. Pat. No. 5,697,281, previously incorporated herein by reference. Alternatively, the body's natural conductive fluids, such as blood, may be sufficient to establish a conductive path between the return electrode(s) and the electrode terminal(s), and to provide the conditions for establishing a vapor layer, as described above. However, conductive fluid that is introduced to the patient is generally preferred over blood because blood will tend to coagulate at certain temperatures. Advantageously, a liquid electrically conductive fluid (e.g., isotonic saline) may be used to concurrently "bathe" the target tissue surface to provide an additional means for removing any tissue, and to cool the region of the target tissue ablated in the previous moment.

The power supply may include a fluid interlock for interrupting power to the electrode terminal(s) when there is insufficient conductive fluid around the electrode terminal (s). This ensures that the instrument will not be activated when conductive fluid is not present, minimizing the tissue damage that may otherwise occur. A more complete description of such a fluid interlock can be found in commonly assigned, co-pending U.S. application Ser. No. 09/058,336, filed Apr. 10, 1998, the complete disclosure of which is incorporated herein by reference.

In lipectomy procedures, it may also be necessary to retrieve or aspirate the electrically conductive fluid, the non-condensable gaseous products of ablation and/or fatty tissue fragments that have not been completed ablated in situ. For example, in liposuction procedures, it may be desired to remove the underlying fatty tissue that is not ablated in situ by the electrical energy. This may be accomplished by first breaking down this tissue with the Coblation® mechanism of the present invention, and then aspirated the remaining tissue fragments from the patient. Accordingly, the system of the present invention may include one or more suction or aspiration lumen(s) in the instrument, or on another instrument, coupled to a suitable vacuum source for aspirating fluids from the target site. In addition, the invention may include one or more aspiration electrode(s) coupled to the distal end of the suction lumen for ablating, or at least reducing the volume of, non-ablated tissue fragments that are aspirated into the lumen. The aspiration electrode(s) function mainly to inhibit clogging of the suction lumen that may otherwise occur as larger tissue fragments are drawn therein. The aspiration electrode(s) may be different from the ablation electrode terminal(s), or the same electrode(s) may serve both functions. A more complete description of instruments incorporating aspiration electrode(s) can be found in commonly assigned, U.S. Pat. No. 6,190,381, the complete disclosure of which is incorporated herein by reference.

In one configuration, each individual electrode terminal in the electrode array is electrically insulated from all other electrode terminals in the array of an electrosurgical instrument, and each terminal is connected to a power source which is isolated from each of the other electrode terminals in the array, or to circuitry which limits or interrupts current flow to the electrode terminal when low resistivity material (e.g., blood, electrically conductive saline irrigant or electrically conductive gel) causes a lower impedance path between the return electrode and the individual electrode terminal. The isolated power sources for each individual electrode terminal may be separate power supply circuits having internal impedance characteristics which limit power to the associated electrode terminal when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the electrode terminals through independently actuatable switches, or by independent current limiting elements, such as inductors, capacitors, resistors and/or combinations thereof. The current limiting elements may be provided in the probe, connectors, cable, controller or along the conductive path from the controller to the distal tip of the probe. Alternatively, the resistance and/or capacitance may occur on the surface of the active electrode terminal(s) due to oxide layers which form selected electrode terminals (e.g., titanium or a resistive coating on the surface of metal, such as platinum).

The tip region of the probe may comprise many independent electrode terminals designed to deliver electrical energy in the vicinity of the tip. The selective application of electrical energy to the conductive fluid is achieved by connecting each individual electrode terminal and the return electrode to a power source having independently controlled or current limited channels. The return electrode may be a tubular member of conductive material, proximal to the electrode array at the tip, which also serves as a conduit for the supply of the electrically conductive fluid between the active and return electrodes. The application of high frequency voltage between the return electrode and the electrode array results in the generation of high electric field intensities at the distal tips of the electrode terminals with conduction of high frequency current from each individual electrode terminal to the return electrode. The current flow from each individual electrode terminal to the return electrode is controlled by either active or passive means, or a combination thereof, to deliver electrical energy to the surrounding conductive fluid while minimizing energy delivery to surrounding (non-target) tissue.

The application of a high frequency voltage between the return electrode and the electrode array for appropriate time intervals effects heating of the conductive fluid and contraction of the target tissue. The tissue volume over which energy is dissipated (i.e., a high current density exists) may be precisely controlled, for example, by the use of a multiplicity of small electrode terminals whose effective diameters or principal dimensions range from about 10 mm to 0.01 mm, preferably from about 5 mm to 0.05 mm, and more preferably from about 3 mm to 0.1 mm. Electrode areas for both circular and non-circular terminals will have a contact area (per electrode terminal) below 25 $mm^2$, preferably being in the range from 0.0001 $mm^2$ to 1 $mm^2$, and more preferably from 0.005 $mm^2$ to 0.5 $mm^2$. The circumscribed area of the electrode array is in the range from 0.25 $mm^2$ to 75 $mm^2$, preferably from 0.5 $mm^2$ to 40 $mm^2$, and will usually include at least two isolated electrode terminals and preferably about three electrode terminals. Of course, the array may include more than three electrode terminals (e.g., 50 or more electrode terminals) disposed over the distal contact surfaces on the shaft. The use of small diameter electrode terminals increases the electric field intensity and reduces the extent or depth of tissue heating as a consequence of the divergence of current flux lines which emanate from the exposed surface of each electrode terminal.

The electrode terminal(s) are formed over a tissue treatment surface on the shaft of the electrosurgical probe. The return electrode surface may be recessed relative to the distal end of the probe and may be recessed within a fluid conduit provided for the introduction of electrically conductive fluid to the site of the target tissue and electrode terminal(s).

The area of the tissue treatment surface can vary widely, and the tissue treatment surface can assume a variety of geometries, with particular areas and geometries being selected for specific applications. Active electrode surfaces can have areas in the range from 0.25 $mm^2$ to 75 $mm^2$, usually being from about 0.5 $mm^2$ to 40 $mm^2$. The geometries can be planar, concave, convex, hemispherical, conical, linear "in-line" array, or virtually any other regular or irregular shape. Most commonly, the active electrode(s) or electrode terminal(s) will be formed at the distal tip of the electrosurgical probe shaft, frequently being planar, disk-shaped, or hemispherical surfaces for use in reshaping procedures or being linear arrays for use in cutting. Alternatively or additionally, the active electrode(s) may be formed on lateral surfaces of the electrosurgical probe shaft (e.g., in the manner of a spatula), facilitating access to certain body structures in endoscopic or percutaneous procedures.

In one embodiment, the electrode array comprises a plurality of substantially elongate electrode terminals spaced on the contact surface of the shaft. Preferably, the contact surface is an electrically insulating electrode support member extending from the shaft of the probe. The elongate electrode terminals will typically have a length of about 0.5 to 30 mm, preferably about 1 to 15 mm, and more preferably about 3 to 7 mm. The width of the elongate electrode terminals is usually about 0.01 to 2 mm, preferably about 0.05 to 1 mm, and more preferably about 0.1 to 0.5 mm. The elongate electrode terminals will be spaced from each other by a distance of about 0.05 to 4 mm, preferably about 0.1 mm to 2 mm. Although the array may comprise one electrode terminal or over 50 electrode terminals, applicant has found that two to ten electrode terminals provides a substantially uniform application of energy to the tissue at the treatment site.

In the exemplary embodiment, the electrode support comprises a plurality of wafer layers bonded together, e.g., by a glass adhesive or the like. The wafer layers each have conductive strips printed thereon to form the electrode terminal(s) and the return electrode(s). In one embodiment, the proximal end of the wafer layers will have a number of holes extending from the conductor strips to an exposed surface of the wafer layers for connection to electrical conductor lead traces in the electrosurgical probe or hand-piece. The wafer layers preferably comprise a ceramic material, such as alumina, and the electrode will preferably comprise a metallic material, such as gold, platinum, palladium, tungsten, silver, or their alloys, and the like. Suitable multilayer ceramic electrodes are commercially available from e.g., VisPro Corporation of Beaverton, Oreg.

The electrically conductive fluid should have a threshold conductivity to provide a suitable conductive path between the return electrode and the electrode terminal(s). The electrical conductivity of the fluid (in units of milliSiemens per centimeter or mS/cm) will usually be greater than 0.2 mS/cm, preferably will be greater than 2 mS/cm, and more preferably greater than 10 mS/cm. In an exemplary embodiment, the electrically conductive fluid is isotonic saline, which has a conductivity of about 17 mS/cm. Alternatively, the fluid may be an electrically conductive gel or spray, such as a saline electrolyte gel, a conductive ECG spray, an electrode conductivity gel, an ultrasound transmission or scanning gel, or the like. Suitable gels or sprays are commercially available from Graham-Field, Inc. of Hauppauge, N.Y. In addition, other electrically conductive fluids may be used, as described in U.S. Provisional Patent Application No. 60/098,122, filed Aug. 27, 1998, the complete disclosure of which is incorporated herein by reference.

In some embodiments, the electrode support and the fluid outlet may be recessed from an outer surface of the probe or handpiece to confine the electrically conductive fluid to the region immediately surrounding the electrode support. In addition, the shaft may be shaped so as to form a cavity around the electrode support and the fluid outlet. This helps to assure that the electrically conductive fluid will remain in contact with the electrode terminal(s) and the return electrode(s) to maintain the conductive path therebetween. In addition, this will help to maintain a vapor or plasma layer between the electrode terminal(s) and the tissue at the treatment site throughout the procedure, which reduces the thermal damage that might otherwise occur if the vapor layer were extinguished due to a lack of conductive fluid. The electrically conductive fluid also helps maintain the tissue temperature as low as possible during the procedure.

The voltage applied between the return electrode and the electrode array will be at high or radio frequency (RF), typically between about 5 kHz and 20 MHz, usually being between about 30 kHz and 2.5 MHz, preferably being between about 50 kHz and 500 kHz, more preferably less than 350 kHz, and often between about 100 kHz and 200 kHz. The RMS (root mean square) voltage applied will usually be in the range from about 5 volts RMS to 1000 volts RMS, typically being in the range of from about 10 volts RMS to 500 volts RMS, depending on the electrode terminal size, the operating frequency and the operation mode of the particular procedure or desired effect on the tissue (i.e., contraction, coagulation or ablation). Typically, the peak-to-peak voltage will be in the range of 10 to 2000 volts, usually in the range of 20 to 1200 volts, and often in the range of from about 40 to 800 volts (again, depending on the electrode size, the operating frequency and the operation mode).

Figure 21:
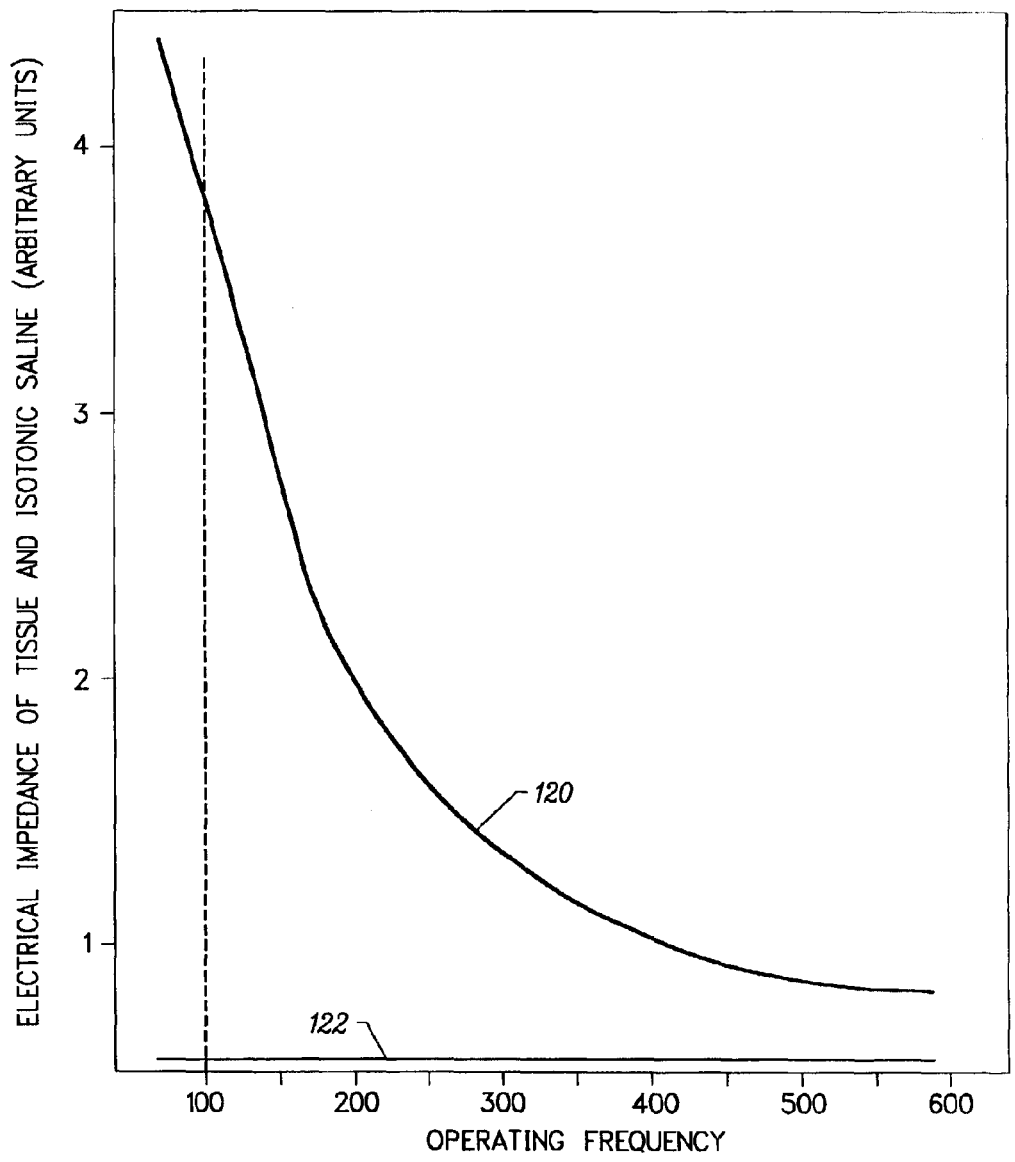
FIG. 21 is a graph illustrating the electrical impedance of tissue and isotonic saline with operating frequency.

An important aspect of the present invention is the discovery that the frequency of the output voltage of the generator can be selected to control the depth of tissue heating. Referring to FIG. 21, the electrical impedance of tissue is known to decrease with increasing frequency due to the electrical properties of cell membranes which surround electrically conductive cellular fluid. As shown, the electrical impedance of tissue to current at a frequency of 100 kHz is on the order of four times larger than at a frequency of 450 to 500 kHz. As a result of the higher tissue impedance at lower frequency, the current flux lines tend to penetrate less deeply resulting in a smaller depth of tissue heating. This principle of operation of the present invention can be used to advantage in applications where the depth of tissue heating is to be maintained small (e.g., in the range of from about 0.2 to 0.5 mm). Preferably, the operating frequency should be below 350 kHz for applications requiring shallow depths of tissue heating (e.g., less than 1.5 mm). Conversely, in situations where much larger depths of tissue heating are to be effected, a higher output voltage frequency may be used. By way of example, to achieve therapeutic collagen shrinkage to a depth of 1.5 to 3.0 mm, a higher operating frequency may be used (e.g., 500 kHz). Alternatively, the diameter of the electrode terminals and/or the spacing between the outer perimeter of the electrode terminals and the electrode support member may be selected to increase the depth of current penetration. By way of example, increasing the distance between the outer perimeter of the support member and the electrode terminals will increase the depth of heating for a given operating frequency.

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with e.g., lasers claiming small depths of necrosis, which are generally pulsed at about 10 Hz to 20 Hz). In addition, the duty cycle (i.e., cumulative time in any one-second interval that energy is applied) is on the order of about 50% for the present invention, as compared with pulsed lasers which typically have a duty cycle of about 0.0001%.

The preferred power source of the present invention delivers a high frequency current selectable to generate average power levels ranging from several milliwatts to tens of watts per electrode, depending on the volume of target tissue being treated, the total number of electrode(s), and/or the maximum allowed temperature selected for the probe tip. The power source allows the user to select the voltage level according to the specific requirements of a particular arthroscopic surgery, cosmetic surgery, dermatological procedure, ophthalmic procedures, open surgery or other endoscopic surgery procedure. A description of a suitable power source can be found in U.S. Provisional Patent Application No. 60/062,997, filed on Oct. 23, 1997, the complete disclosure of which has been previously incorporated herein by reference.

The power source may be current limited or otherwise controlled so that undesired heating of the target tissue or surrounding (non-target) tissue does not occur. In a presently preferred embodiment of the present invention, current limiting inductors are placed in series with each independent electrode terminal, where the inductance of the inductor is in the range of 10 uH to 50,000 uH, depending on the electrical properties of the target tissue, the size of the electrode terminal(s), the desired tissue heating rate and the operating frequency. Alternatively, capacitor-inductor (LC) circuit structures may be employed, as described previously in PCT application No. PCT/US94/05168, the complete disclosure of which is incorporated herein by reference. Additionally, current limiting resistors may be selected. Preferably, these resistors will have a large positive temperature coefficient of resistance so that, as the current level begins to rise for any individual electrode terminal in contact with a low resistance medium (e.g., saline irrigant or conductive gel), the resistance of the current limiting resistor increases significantly, thereby minimizing the power delivery from said electrode terminal into the low resistance medium (e.g., saline irrigant or conductive gel).

It should be clearly understood that the invention is not limited to electrically isolated electrode terminals, or even to a plurality of electrode terminals. For example, the array of active electrode terminals may be connected to a single lead that extends through the probe shaft to a power source of high frequency current. Alternatively, the probe may incorporate a single electrode that extends directly through the probe shaft or is connected to a single lead that extends to the power source.

Referring to FIG. 1, an electrosurgical system 11 generally comprises an electrosurgical handpiece or probe 10 connected to a power supply 28 for providing high frequency voltage to a target site, and a fluid source 21 for supplying electrically conductive fluid 50 to probe 10. Probe 10 generally includes a proximal handle 12 and a distal tip 13 having an electrode support member 70 with one or an array of electrode terminals 58 and one or more return electrodes 100, 102 (see FIGS. 2, 4 and 5) disposed on the support member 70. A connecting cable 34 has a connector 26 for electrically coupling the electrodes in probe 10 to power supply 28. The electrode terminals 58 are electrically isolated from each other, and each of the terminals 58 is connected to an active or passive control network within power supply 28 by means of a plurality of individually insulated conductors (not shown). A fluid supply tube 15 is connected to a fluid tube 110 of probe 10 for supplying electrically conductive fluid 50 to a distal tip 13 (see FIGS. 16A, 16B, and 17).

Power supply 28 has an operator controllable voltage level adjustment 30 to change the applied voltage level, which is observable at a voltage level display 32. Power supply 28 also includes first, second and third foot pedals 37, 38, 39 and a cable 36 which is removably coupled to power supply 28. The foot pedals 37, 38, 39 allow the surgeon to remotely adjust the energy level applied to electrode terminals 58. In an exemplary embodiment, first foot pedal 37 is used to place the power supply into the "ablation" mode and second foot pedal 38 places power supply 28 into the "sub-ablation" or coagulation mode. The third foot pedal 39 allows the user to adjust the voltage level within the ablation mode. In the ablation mode, a sufficient voltage is applied to the electrode terminals to establish the requisite conditions for molecular dissociation of the tissue (e.g., by vaporizing a portion of the electrically conductive fluid, ionizing the vapor layer, and accelerating charged particles against the tissue). As discussed above, the requisite voltage level for ablation will vary depending on the number, size, shape and spacing of the electrodes, the distance to which the electrodes extend from the support member, etc. When the surgeon is using the power supply in the "ablation" mode, voltage level adjustment 30 or third foot pedal 39 may be used to adjust the voltage level to adjust the degree or aggressiveness of the ablation.

Of course, it will be recognized that the voltage and modality of the power supply may be controlled by other input devices. However, applicant has found that foot pedals are convenient methods of controlling the power supply while manipulating the probe during a surgical procedure.

In the coagulation or sub-ablation mode, the power supply 28 applies a low enough voltage to one or more electrode terminals (or one or more coagulation electrodes) to avoid vaporization of the electrically conductive fluid, formation of a plasma and subsequent molecular dissociation of the tissue. The surgeon may automatically toggle the power supply between the ablation and sub-ablation modes by alternatively stepping on foot pedals 37, 38, respectively. This allows the surgeon to quickly move between coagulation and ablation in situ, without having to remove his/her concentration from the surgical field or without having to request an assistant to switch the power supply. By way of example, as the surgeon is sculpting soft tissue in the ablation mode, the probe typically will simultaneously seal and/or coagulate small severed vessels within the tissue. However, larger vessels, or vessels with high fluid pressures (e.g., arterial vessels) may not be sealed in the ablation mode. Accordingly, the surgeon can simply step on foot pedal 38, automatically lowering the voltage level below the threshold level for ablation, and apply sufficient pressure onto the severed vessel for a sufficient period of time to seal and/or coagulate the vessel. After this is completed, the surgeon may quickly move back into the ablation mode by stepping on foot pedal 37. A specific design of a suitable power supply for use with the present invention can be found in U.S. Provisional Patent Application 60/062,997, filed Oct. 23, 1997.

Figure 2:
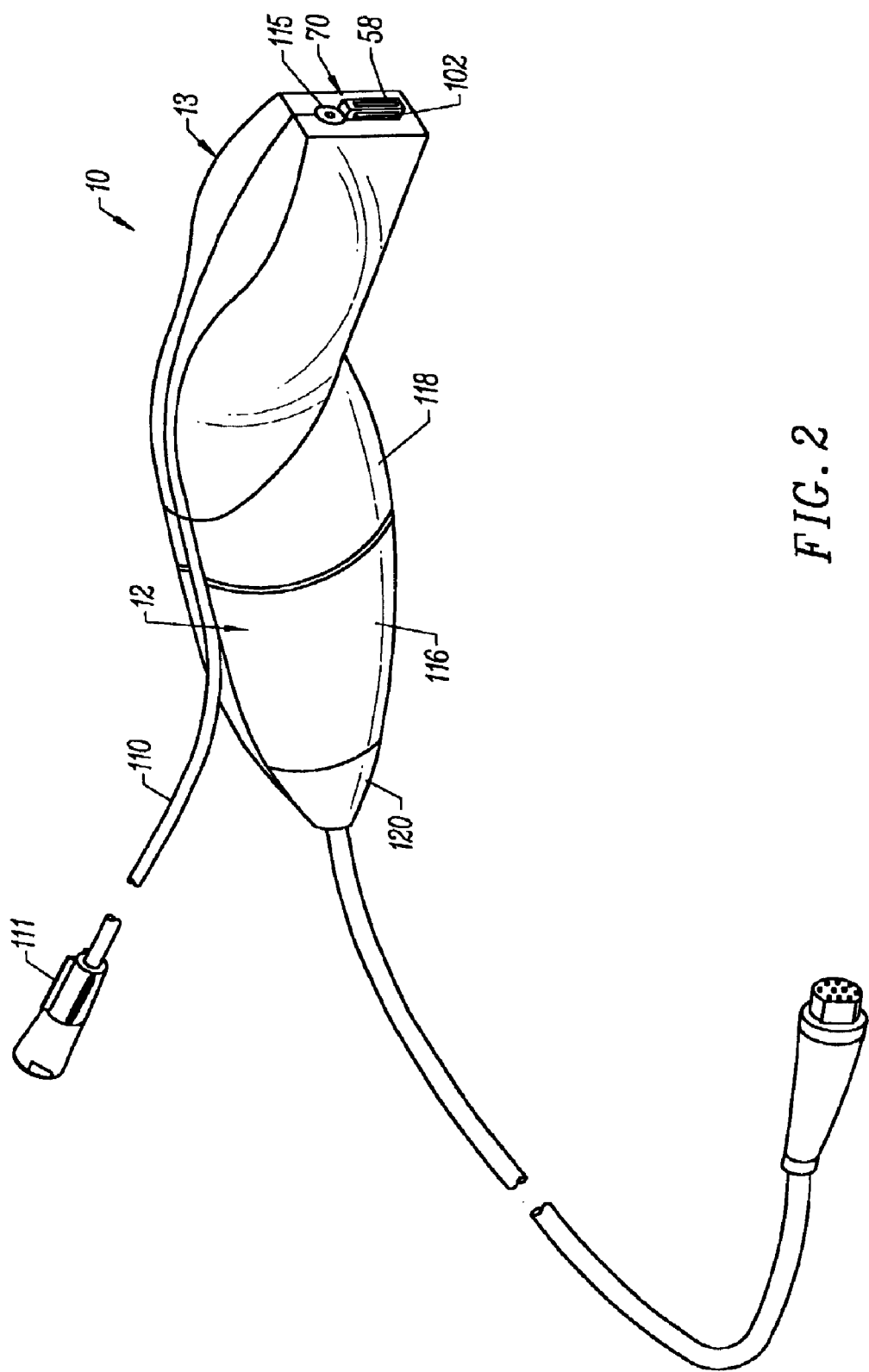
FIG. 2 is a perspective view of one embodiment of an electrosurgical probe constructed according to the principles of the present invention.
Figure 5:
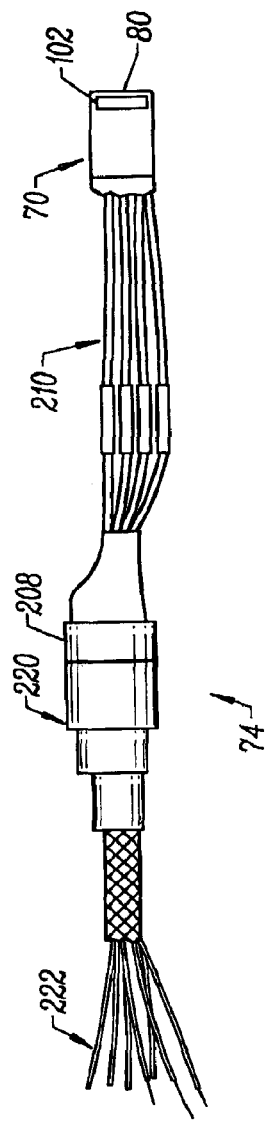
FIG. 5 illustrates the electrical connections and the electrode support of the handpiece in greater detail.

Referring now to FIGS. 2–5, an exemplary electrosurgical probe 10 comprises a shaft or disposable tip 13 removably coupled to a proximal handle 12, and an electrically insulating electrode support member 70 extending from tip 13 for supporting a plurality of electrode terminals 58 (see FIGS. 2 and 5). Tip 13 and handle 12 typically comprise a plastic material that is easily molded into a suitable shape for handling by the surgeon. As shown in FIGS. 3 and 5, handle 12 defines an inner cavity 72 that houses the electrical connections 74 (discussed below in reference to FIG. 5), and provides a suitable interface for connection to electrical connecting cable 34 (see FIG. 1). In the exemplary embodiment, handle 12 is constructed of a steam autoclavable plastic or metal (e.g., polyethylether ketone, or a stable metal alloy containing aluminum and/or zinc so that it can be re-used by sterilizing handle 12 between surgical procedures. High service temperature materials are preferred, such as a silicone cable jacket and a polyetherimide or ULTEM® handpiece that can withstand a repeated exposure to high temperatures.

Figure 3A:
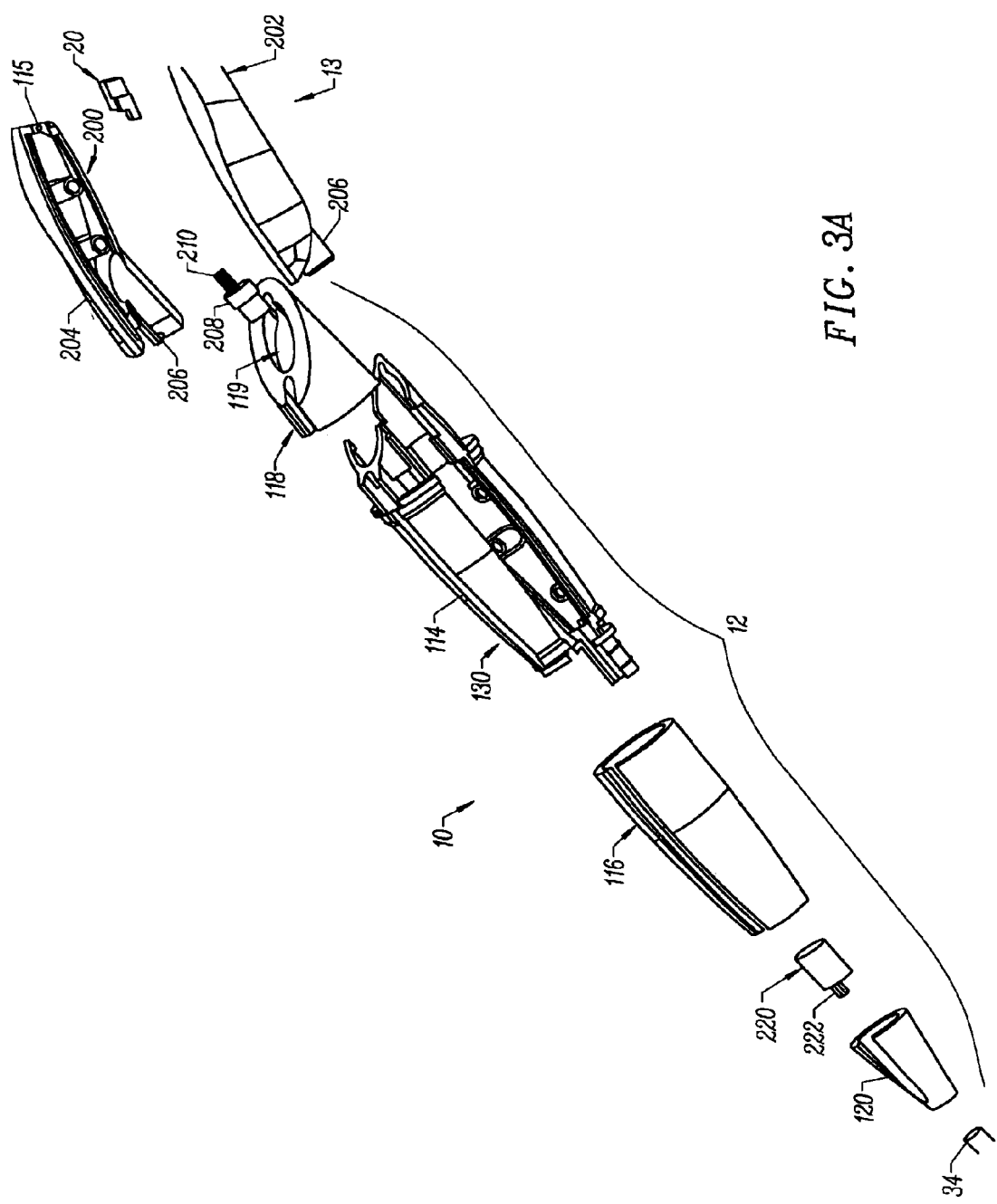
FIGS. 3A–3C are exploded, isometric views of the probe of FIG. 2.
Figure 3B:
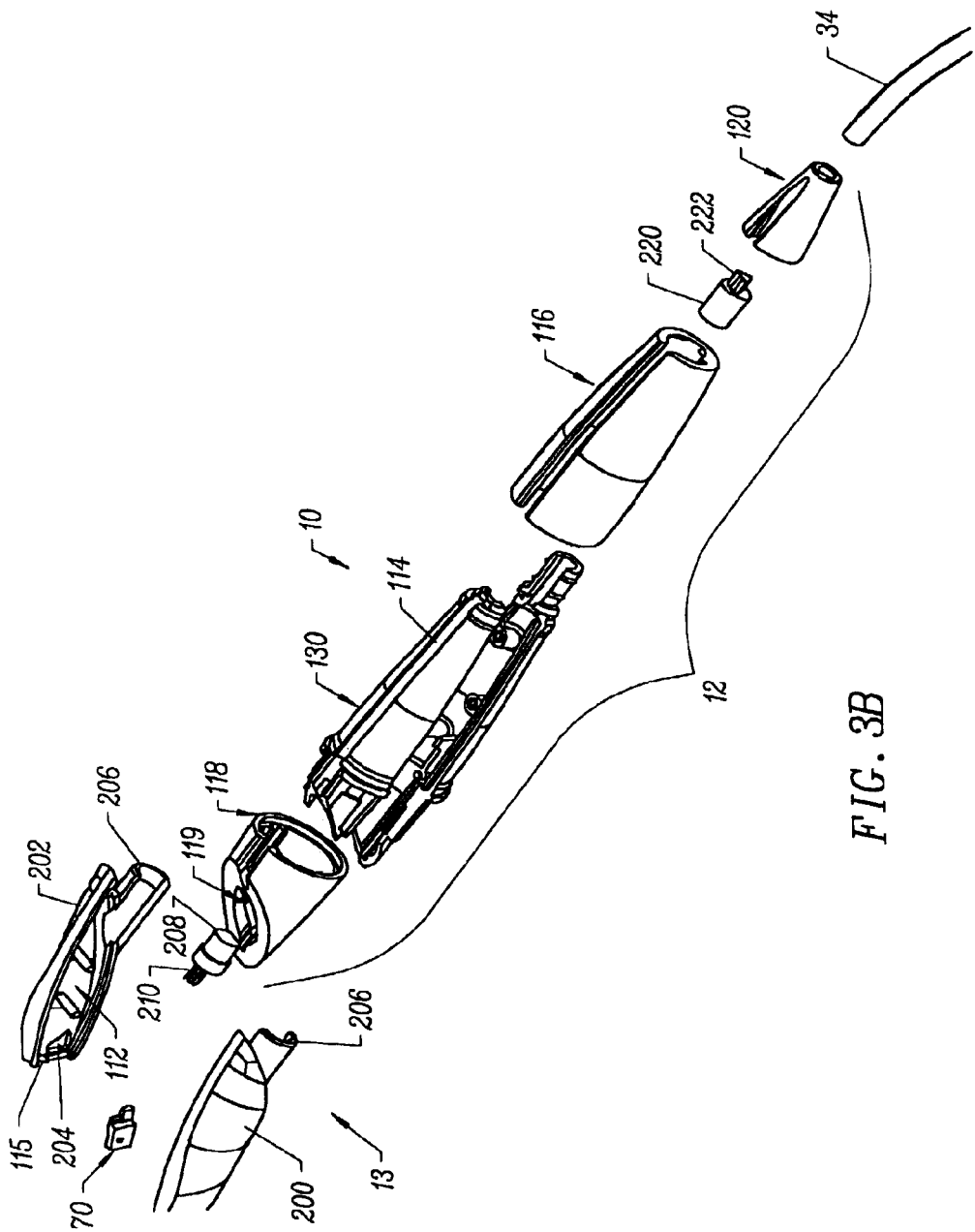
Figure 3C:
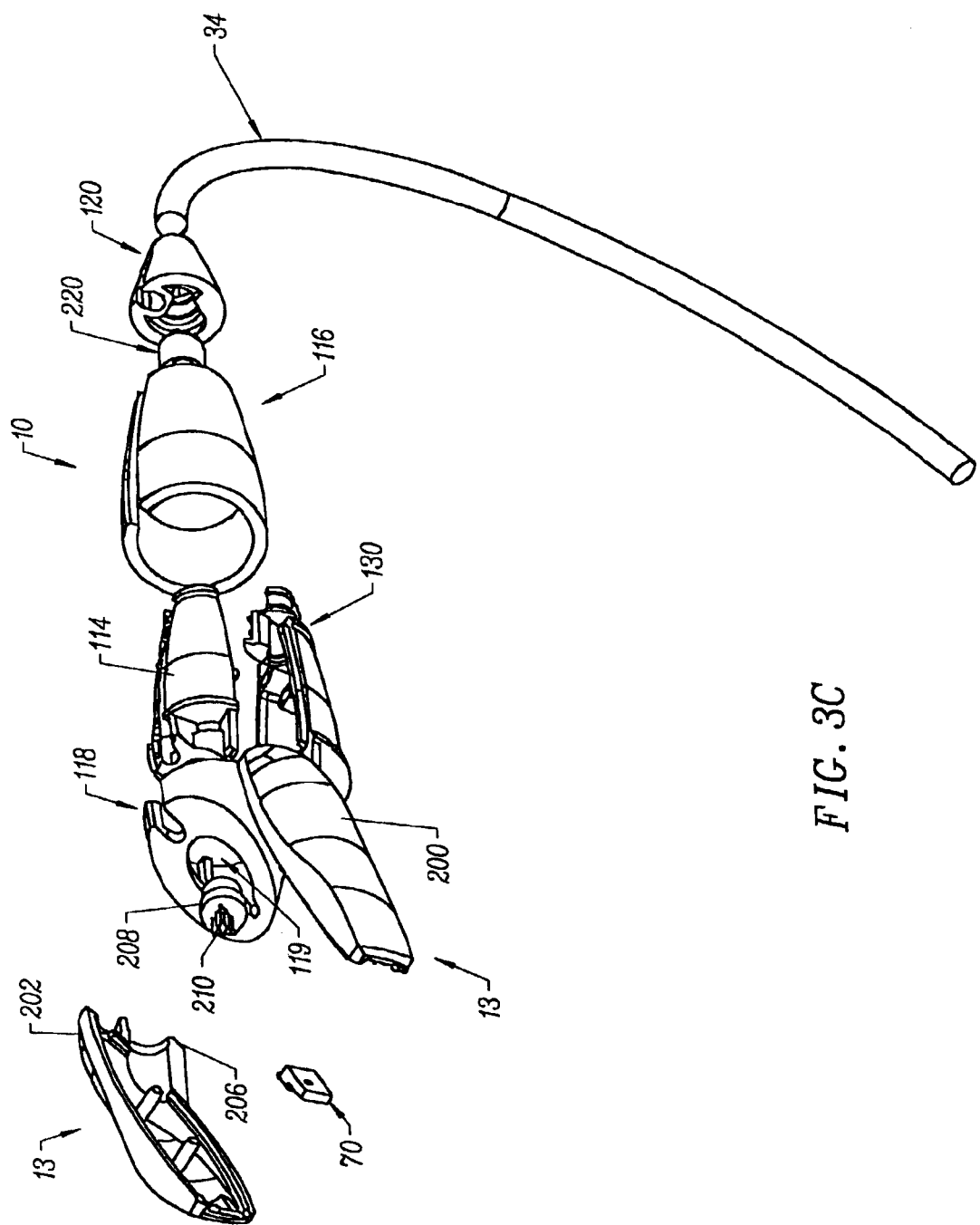

Referring to FIGS. 3A–3C, tip 13 preferably comprises first and second housing halves 200, 202 that snap fit together, and form a recess 204 therebetween for holding electrode support member 70 within the tip 13. Electrode support member 70 extends from the distal end of tip 13 (usually by about 0.5 to 20 mm), and provides support for a plurality of electrically isolated electrode terminals 58 and one or more return electrodes 100, 102 (see FIG. 4). Alternatively, electrode support member 70 may be recessed from the distal end of tip 13 to help confine the electrically conductive fluid around the electrode terminals 58 during the surgical procedure, as discussed above. Electrode support member 70 has a substantially planar tissue treatment surface 80 that is usually disposed at an angle of about 10° to 90° relative to the longitudinal axis of handle 12 to facilitate handling by the surgeon. In the exemplary embodiment, this function is accomplished by orienting tip 13 at an acute angle relative to the longitudinal axis of handle 12.

In the embodiment shown in FIGS. 2–5, probe 10 includes first and second return electrodes 100, 102 for completing the current path between electrode terminals 58 and power supply 28 (see FIG. 1). As shown, return electrodes 100, 102 preferably have fluid contact surfaces on either lateral surface 104, 106 of electrode support member 70 slightly proximal to tissue treatment surface 80, typically about 0.1 to 2 mm, preferably about 0.2 to 1 mm. Return electrodes 100, 102 will usually have an exposed surface area of about 5 mm$^2$ to 25 mm$^2$, preferably about 18 mm$^2$ to about 20 mm$^2$. Return electrodes 100, 102 are coupled to a connector 104 (details of this connection are discussed below) that extends to the proximal end of handle 13, where it is suitably connected to power supply 28 (FIG. 1).

Referring to FIGS. 3A–3C and FIG. 5, tip 13 further includes a proximal hub 206 for supporting a male electrical connector 208 that holds a plurality of wires 210 each coupled to one of the electrode terminals 58 and the return electrodes 100, 102 on support member 70 (see FIGS. 7–13 for details of the representative support member 70). A female connector 220 housed within handle 12 is removably coupled to male connector 208, and a plurality of wires 222 extend from female connector 220 through a strain relief 120 to cable 34. Both sets of wires 210, 222 are insulated to prevent shorting in the event of fluid ingress into the probe 10. This design allows for removable connection of the electrodes in tip 13 with the connector 220 within handle 12 so that the handle can be re-used with different tips 13. Probe 10 will preferably also include an identification element, such as a coded resistor (not shown), for programming a particular voltage output range and mode of operation for the power supply. This allows the power supply to be employed with a variety of different probes for a variety of different applications.

As shown in FIG. 5, return electrodes 100, 102 are not directly connected to electrode terminals 58. To complete this current path so that electrode terminals 58 are electrically connected to return electrodes 102, 100, electrically conductive fluid (e.g., isotonic saline or electrically conducting gel) is located between the active and return electrodes during a surgical procedure. In the representative embodiment, probe 10 includes a fluid tube 110 (FIG. 2) for delivering electrically conductive fluid to the target site. Fluid tube 110 is sized to extend through a groove 114 in handle 12 and through an inner cavity 112 (FIG. 3 and FIGS. 3A–3C) in tip 13 to a distal opening 115 (FIG. 4) located adjacent electrode support member 70. Tube 110 extends all the way through inner cavity 112 to opening 115 to eliminate any possible fluid ingress into cavity 112. As shown in FIGS. 1 and 2, fluid tube 110 includes a proximal connector 111 for coupling tube 110 to an electrically conductive fluid source 21.

Probe 10 will also include a valve or equivalent structure for controlling the flow rate of the electrically conductive fluid to the target site. In the representative embodiment shown in FIGS. 3A–3C, handle 12 comprises a main body 130 coupled between distal hub 118 and strain relief 120, and a rotatable sleeve 116 around main body 130. Distal hub 118 has an opening 119 for receiving proximal hub 206 of tip 13 for removably coupling the tip 13 to the handle 12. Sleeve 116 is rotatably coupled to strain relief 120 and distal hub 118 to provide a valve structure for fluid tube 110. As shown in FIG. 2, fluid tube 110 extends through groove 114 from strain relief 120, through main body 130 and distal hub 118 to tip 13. Rotation of sleeve 116 will impede, and eventually obstruct, the flow of fluid through tube 110. Of course, this fluid control may be provided by a variety of other input and valve devices, such as switches, buttons, etc.

In alternative embodiments, the fluid path may be directly formed in probe 10 by, for example, a central inner lumen or an annular gap (not shown) within the handle and the tip. This inner lumen may be formed near the perimeter of the probe 10 such that the electrically conductive fluid tends to flow radially inward towards the target site, or the inner lumen may be formed towards the center of probe 10 so that the fluid flows radially outward. In addition, the electrically conductive fluid may be delivered from a fluid delivery element (not shown) that is separate from probe 10. In arthroscopic surgery, for example, a joint cavity will be flooded with isotonic saline and the probe 10 will be introduced into this flooded cavity. Electrically conductive fluid will be continually resupplied to maintain the conduction path between return electrodes 100, 102 and electrode terminals 58. A more complete description of alternative electrosurgical probes incorporating one or more fluid lumen(s) can be found in U.S. Pat. No. 5,697,281, the complete disclosure of which has previously been incorporated herein by reference.

Figure 4:
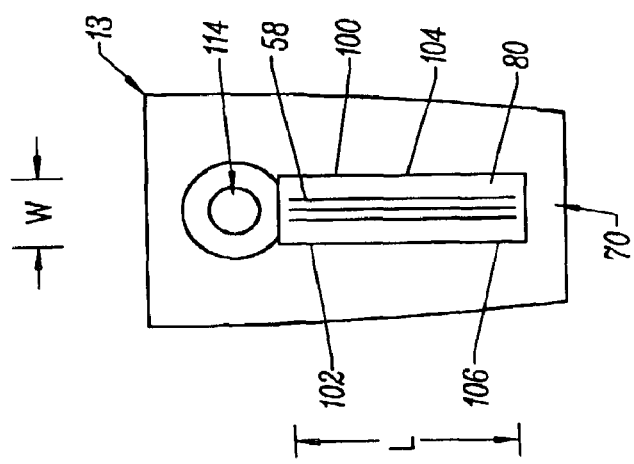
FIG. 4 is an end view of the distal tip of the probe, illustrating an electrode support with a plurality of electrode terminals.
Figure 6:
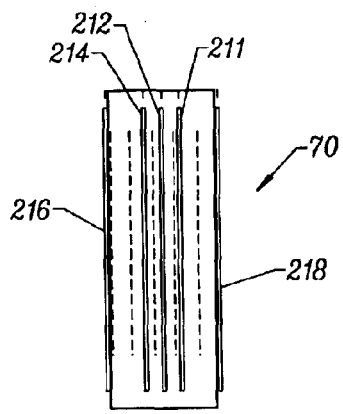
FIG. 6 is an end view of an exemplary electrode support comprising a multi-layer wafer with plated conductors for electrodes.

Referring to FIGS. 4 and 5, electrically isolated electrode terminals 58 are spaced apart over tissue treatment surface 80 of electrode support member 70. In the representative embodiment, the tissue treatment surface 80 has a rectangular cross-sectional shape with a length L in the range of about 0.5 mm to 20 mm (typically about 2 to 10 mm), and a width W in the range from 0.3 mm to 10 mm (typically about 0.5 to 4 mm). The individual electrode terminals 58 have the dimensions described above, and in one embodiment terminals 58 are substantially flush with tissue treatment surface 80. Applicant has found that this configuration minimizes any sharp electrode edges and/or corners that would promote excessively high electric field intensities and associated current densities when a high frequency voltage is applied to the electrode terminals, thereby preventing excessively high rates of ablation, as is preferred for removing thin layers of tissue (e.g., epidermal layers), or completely avoiding ablation in procedures calling for modification (e.g., shrinkage) of target tissue.

It should be noted that the electrode terminals 58 may protrude slightly outward from surface 80, typically by a distance from 0 mm to 2 mm, or the electrode terminals may be recessed from this surface. For example, the electrode terminals 58 may be recessed by a distance from 0.01 mm to 1 mm, preferably 0.01 mm to 0.2 mm. In one embodiment of the invention, the electrode terminals are axially adjustable relative to the tissue treatment surface so that the surgeon can adjust the distance between the treatment surface and the electrode terminals.

Referring now to FIGS. 7–13, an exemplary electrode support member 70 will be described in detail. As shown, electrode support member 70 preferably comprises a multilayer substrate comprising a suitable high temperature, electrically insulating material, such as ceramic. The multilayer substrate is a thin or thick-film hybrid having conductive strips that are adhered to the ceramic wafer layers (e.g., thick-film printed and fired onto or plated onto the ceramic wafers). The conductive strips typically comprise tungsten, gold, nickel, silver, platinum or equivalent materials. In the exemplary embodiment, the conductive strips comprise gold, and they are co-fired together with the wafer layers to form an integral package. The conductive strips are coupled to external wire connectors by holes or vias that are drilled through the ceramic layers, and plated or otherwise covered with conductive material.

Figures 7, 8:
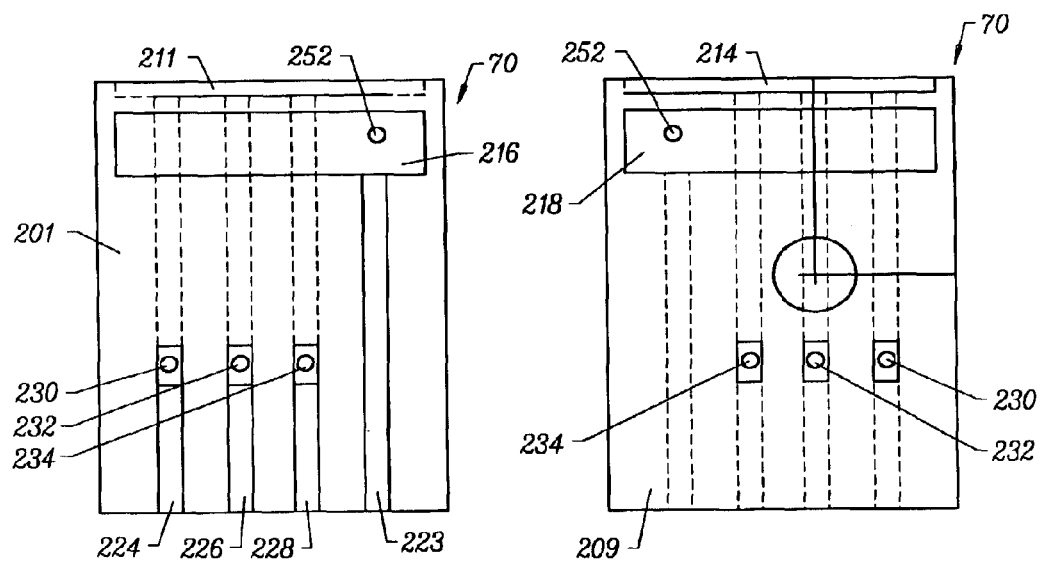
FIGS. 7 and 8 are side views of the electrode support of FIG. 7.

In the representative embodiment, support member 70 comprises five ceramic layers 201, 203, 205, 207, 209 (see FIGS. 9A–13), three gold plated electrode terminals 211, 212, 214 and first and second gold plated return electrodes 216, 218. As shown in FIGS. 8, 9A and 9B, a first ceramic layer 201, which is one of the outer layers of support 70, includes first gold plated return electrode 216 on a lateral surface 220 thereof. First ceramic layer 200 further includes a gold conductive strip 223 extending from return electrode 216 to the proximal end of the layer 201 for coupling to a lead wire (not shown), and three gold conductive lines 224, 226, 228 extending from a mid-portion of the layer 201 to its proximal end. Conductive strips 224, 226, 228 are each coupled to one of the electrode terminals 210, 212, 214 by conductive holes or vias 230, 232, 234, respectively. As shown, all three vias 230, 232, 234 extend through wafer layer 201.

Figure 11A:
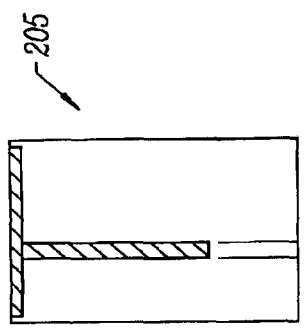
Figure 11B:
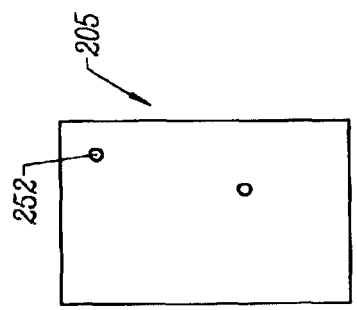
Figure 12A:
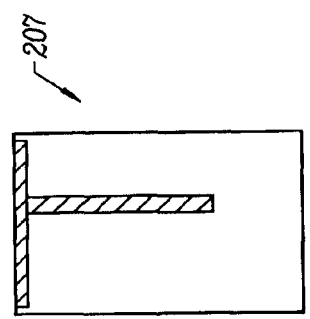
Figure 12B:
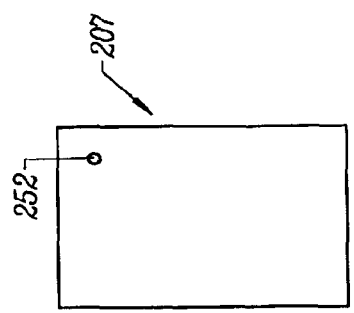
Figure 13:
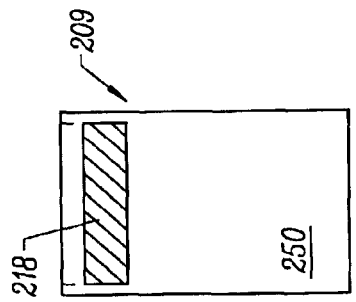

Referring to FIGS. 10A and 10B, a second wafer layer 203 is bonded between the outer wafer layer 201 and a middle wafer layer 205 (FIGS. 11A and 11B). As shown, first electrode terminal 211 is attached to the distal surface of second wafer layer 203, and a conductive strip 240 extends to via 230 to couple electrode terminal 211 to a lead wire. Similarly, wafer layers 205 and 207 (FIGS. 11A and 12B) each have an electrode terminal 212, 214, respectively, plated to their distal surfaces, and a conductive strip 242, 244, respectively, extending to one of the vias 232, 234, respectively. Note that the vias only extend as far as necessary through the ceramic layers. As shown in FIG. 13, another outer wafer layer 209 has a second return electrode 218 plated to the lateral surface 250 of layer 209. The second return electrode 218 is coupled directly to the first return electrode 216 through a via 252 extending through the entire ceramic substrate.

Figure 14:
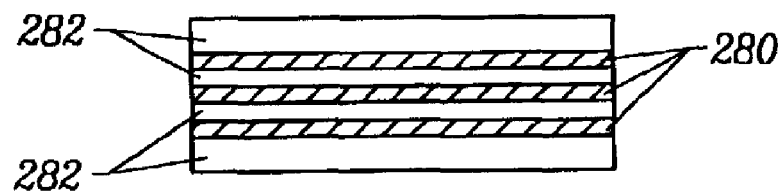
FIGS. 14 and 15 illustrate an alternative multi-layer wafer design according to the present invention.
Figure 15:
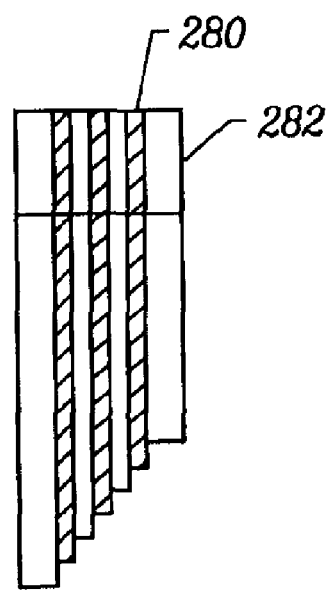

Of course, it will be recognized that a variety of different types of multilayer wafers may be constructed according to the present invention, For example, FIGS. 14 and 15 illustrate an alternative embodiment of the multilayer ceramic wafer, wherein the electrode terminals comprise planar strips 280 that are plated or otherwise bonded between the ceramic wafer layers 282. Each of the planar strips 280 has a different length, as shown in FIG. 15, so that the electrode terminals can be electrically isolated from each other, and coupled to lead wires by vias (not shown).

Figure 16A:
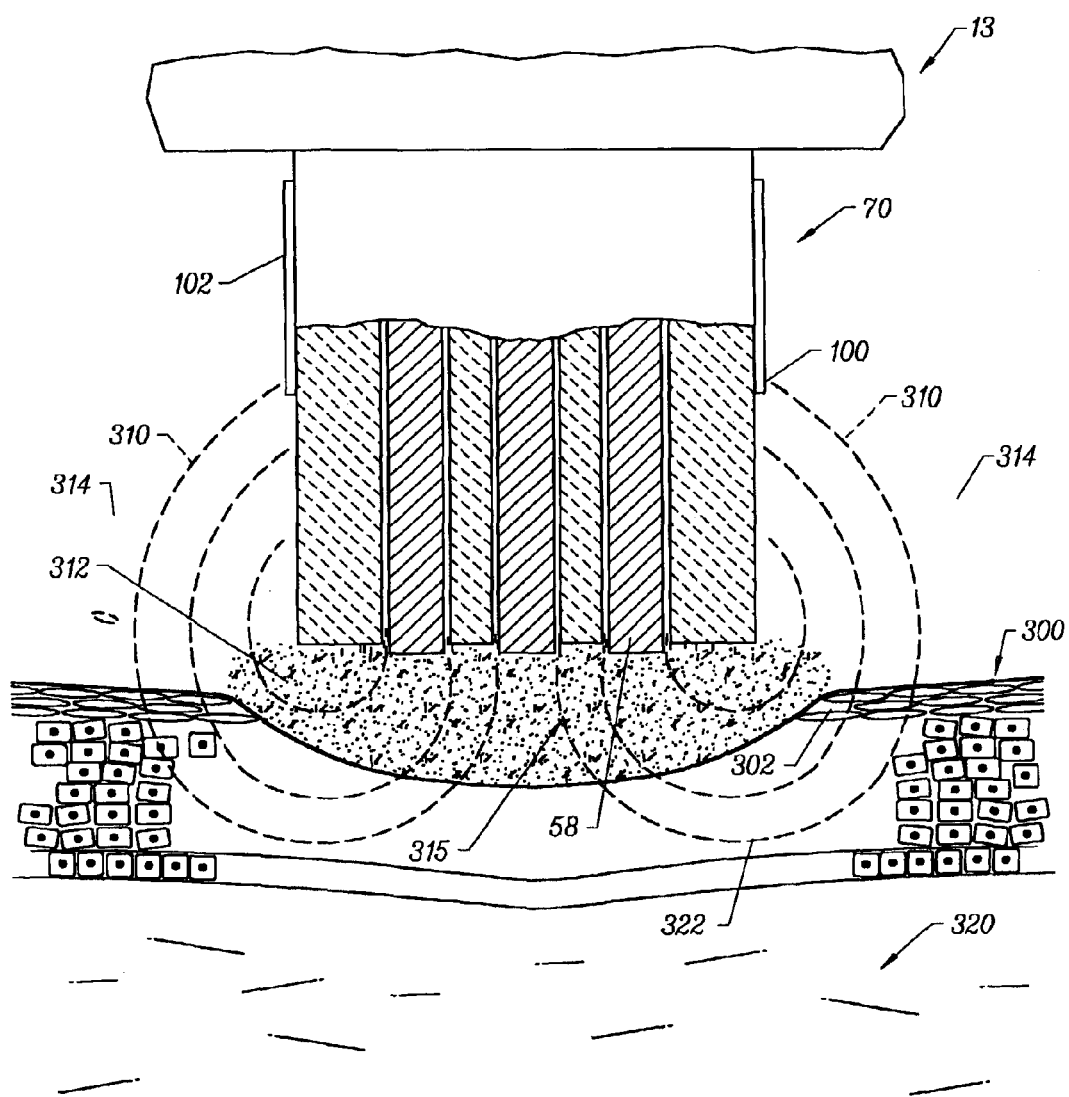
FIG. 16A illustrates a method for treating the outer layer of a patient's skin in a skin resurfacing procedure, wherein an outer layer of epidermis is removed or ablated and the collagen fibers in the underlying dermis are contracted.
Figure 16B:
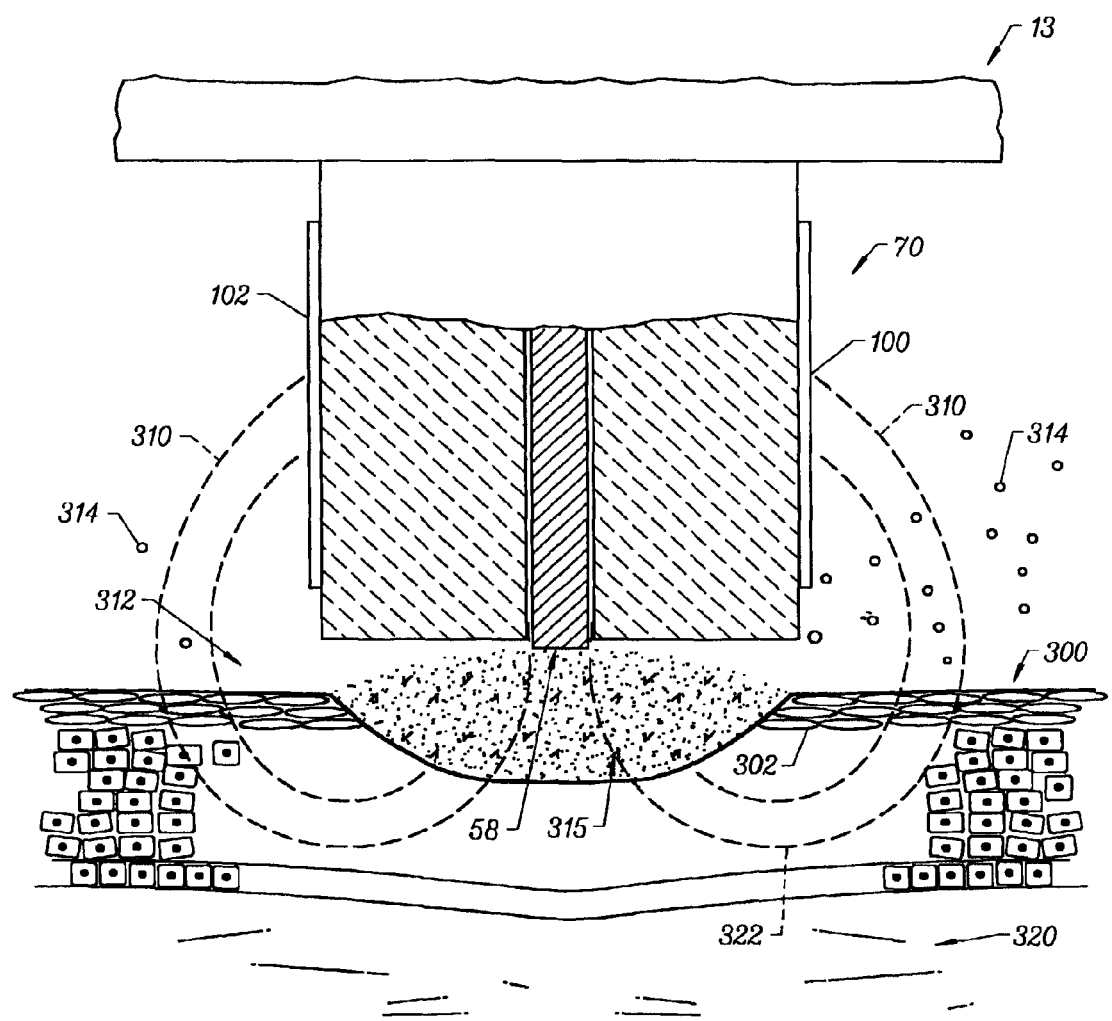
FIG. 16B illustrates a method for treating the outer layer of a patient's skin in a skin resurfacing procedure with an electrosurgical probe having a single, active electrode terminal.

Referring now to FIGS. 16A and 16B, a method of treating tissue on the outer skin of a patient according to the present invention will now be described. As shown, distal tip 13 of probe 10 is positioned such that electrode support 70 is adjacent to the target tissue 302 at the treatment site 300. Electrically conductive fluid 304 is delivered through fluid tube 110 (FIG. 2) through distal opening 115 to the treatment site 300. The rate of fluid flow is controlled with rotatable sleeve 116 (FIG. 3A) such that the zone between the tissue 302 and electrode support 70 is constantly immersed in the fluid. The power supply 28 is then turned on and adjusted such that a high frequency voltage is applied between electrode terminal(s) 58 and return electrodes 100, 102. The electrically conductive fluid 304 provides the conduction path (see current flux lines 310) between electrode terminal (s) 58 and the return electrodes 100, 102 on either side of electrode support 70.

In an exemplary embodiment, the high frequency voltage is sufficient to convert the electrically conductive fluid 304 between the target tissue 302 and electrode terminals 58 into an ionized vapor layer 312 or plasma. As a result of the applied voltage between electrode terminals 58 and the target tissue 302 (i.e., the voltage gradient across the plasma layer 312), charged particles 315 in the plasma (viz., electrons) are accelerated towards the tissue. At sufficiently high voltages, these charged particles 315 gain sufficient energy to cause dissociation of the molecular bonds of tissue components. This molecular dissociation is accompanied by the volumetric removal (i.e., ablative sublimation) of tissue and the production of low molecular weight gases 314, such as oxygen, nitrogen, carbon dioxide, hydrogen and methane. The ablation of target tissue by this process can be precisely controlled, thereby avoiding or minimizing damage to non-target tissue.

In some embodiments, the applied voltage will be sufficient to apply thermal energy to the underlying tissue 320, but insufficient to ablate or vaporize the tissue. This thermal energy will be sufficient to elevate the tissue temperature from normal body temperatures (e.g., 37° C.) to temperatures in the range of from about 45° C. to 90° C., preferably in the range of from about 55° C. to 70° C. and, for the case of skin, and more preferably in the range of about 55° C. to 62° C. This temperature elevation causes contraction of the collagen fibers within the underlying tissue 320. This method tightens the underlying dermis to remove wrinkles and rejuvenate the skin. In some embodiments, such tightening of the dermis may be performed in conjunction with removal of the surface layer(s) (epidermis) of the skin.

Figure 17:
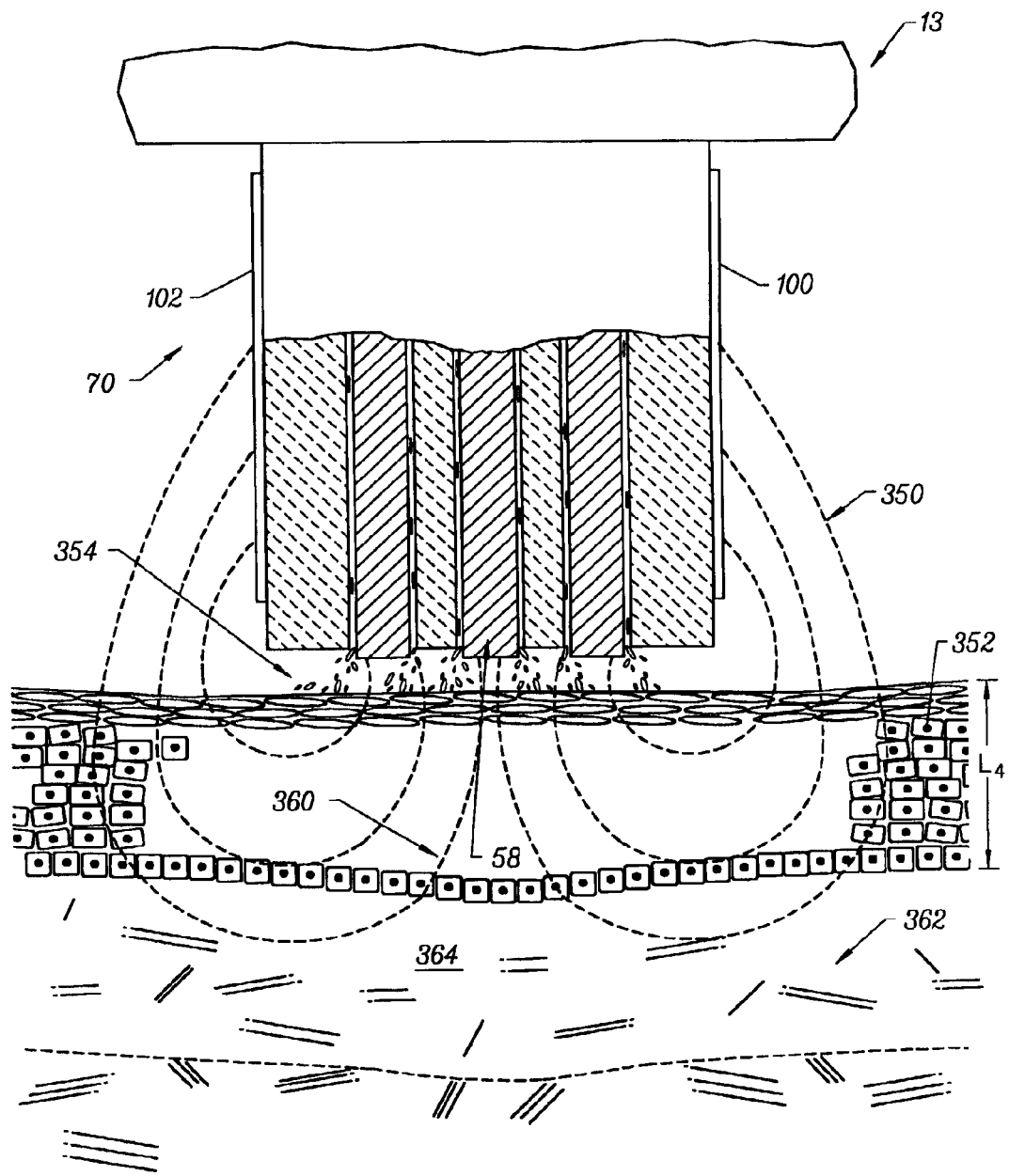
FIG. 17 illustrates a method of skin resurfacing wherein the epidermal layer is separated from the dermis, and then removed by wiping away the separated layer.

An alternative method for skin rejuvenation or wrinkle removal is shown in FIG. 17. In this method, when a voltage is applied between the electrode terminals 58 and the return electrodes 100, 102, electric current flows between the electrode terminals 58 and the return electrode 100, 102 along current flux lines 350. The current flux lines 350 flow a short distance, $L_4$ into the surface of epidermal tissue 352 and through the electrically conductive fluid 354 in the region above the surface of the tissue to complete the current flow path between the electrode terminals 58 and the return electrodes 100, 102. As a consequence of the electrical impedance of the tissue and the proper selection of the applied frequency, voltage, and current, heating of the epidermal tissue 352 occurs in a region 360 below the surface of the tissue 352. This heating elevates the temperature of the tissue and separates the epidermal tissue layer 352 from the underlying dermis 362. The epidermal tissue layer 352 may then be removed by flushing the treatment site, or by brushing away this tissue layer 352 with, for example, a cloth pad, gauze, etc. In skin rejuvenation procedures, collagen may be injected into the dermis after the epidermis has been removed to rejuvenate skin that has lost its elasticity.

In addition, the heating from current flux lines 350 may be sufficient to elevate the temperature of the tissue 364 in the dermis 362 from normal body temperature (e.g. 37° C.) to a temperature in the range of from about 55° C. to 85° C., preferably in the range of from about 60° C. to 70° C. This heating of the dermis 362 will cause irreversible contraction of the collagen within the dermis.

Figure 18A:
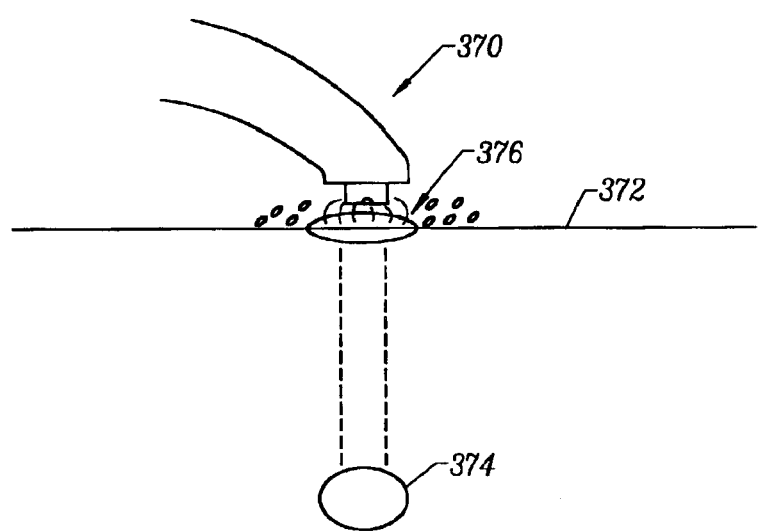
FIGS. 18A and 18B illustrate a method for treating a vascular lesion.
Figure 18B:
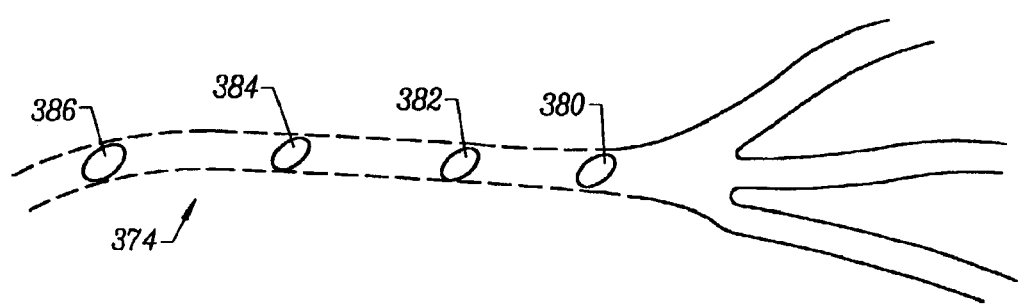

FIGS. 18A and 18B illustrate a method for treating a vascular lesion, such as a port wine stain, face vein, birth mark or the like. As shown in FIG. 18A, an electrosurgical probe 370 is placed on or adjacent to the surface of the skin 372 above the blood vessel 374 to be treated. A voltage is applied between the active and return electrodes (not shown) in the presence of electrically conductive fluid 376 to ablate or cause molecular dissociation of the tissue adjacent the probe 370. As the tissue is removed, the probe will be axially translated through the deepening hole to the vessel 374 (note that a substantially linear probe shaft is preferred in this embodiment). A more complete description of systems and methods for forming channels or holes through tissue is described in commonly assigned, U.S. Pat. No. 5,683,366, the complete disclosure of which is incorporated herein by reference. Once the probe approaches the vessel, thermal energy will be delivered into the vessel via resistive heating as current passes through the tissue. This thermal energy will eventually be sufficient to coagulate the blood vessel 374 and collapse the vessel at that site.

In order to collapse or coagulate a long length of the vessel 374, multiple treatment sites may be necessary. As shown in FIG. 18B, it is desirable to locate the first treatment site 380 at a downstream point with respect to the flow of blood in the vessel. The surgeon may then sequentially treat the vessel at multiple sites (382, 384, 386) upstream from the first site 380.

Figure 19:
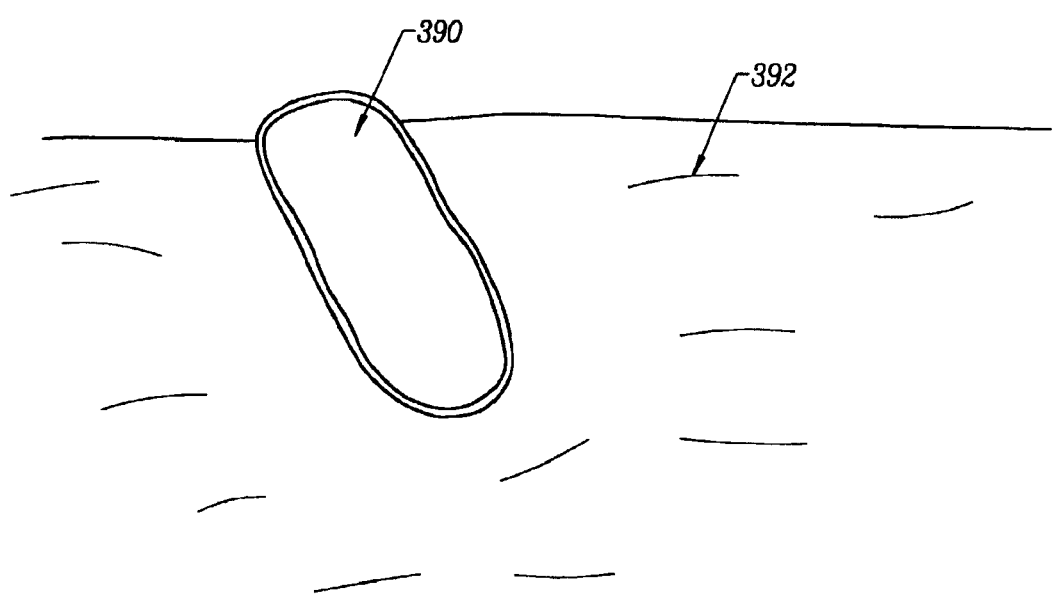
FIG. 19 illustrates a method of removing scalp tissue and/or hair according to the present invention.

Referring now to FIG. 19, a method for transplanting hair according to the present invention is described. A strip of hair (not shown) from a donor region is first excised from the patient. The hair may be excised by removing the tissue around the strip in a similar manner as described above. The hemostatic effects of the electrosurgical system of the present invention result in minimal bleeding at the donor site. The strip is then lifted from the scalp and sutures are used to close the opening.

One of the probes described above are then used to produce incisions 390 in the recipient area 392. As shown in FIG. 19, the depth and diameter of the incision 390 can be accurately controlled. The incisions are preferably formed at an angle to improve the retention of the graft and to form a more cosmetically suitable appearance.

Figure 20:
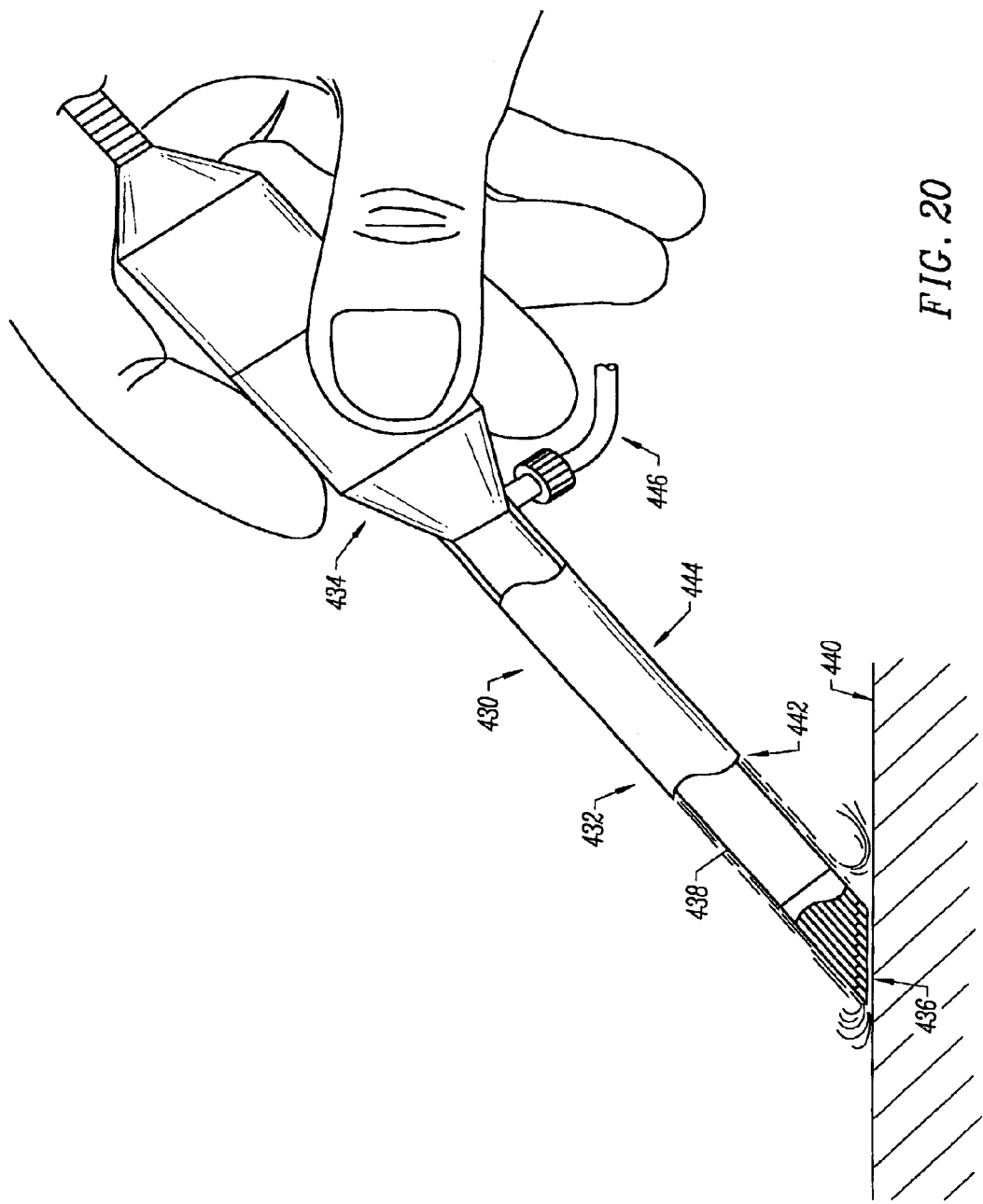
FIG. 20 is a cross-sectional view of an alternative electrosurgical probe for applying high frequency voltage to tissue layers on the skin.

FIG. 20 illustrates an alternative embodiment, where an electrosurgical probe 430 is utilized to remove the surface layers of the epidermis 440. Probe 430 includes a shaft 432 coupled to a proximal handle 434 for holding and controlling shaft 432. Similar to previous embodiments, probe 430 includes an active electrode array 436 at the distal tip of shaft 432, an annular return electrode 438 extending through shaft 432 and spaced proximally from the active electrode array 436, and an annular lumen 442 between return electrode 438 and an outer insulating sheath 444. Probe 430 further includes a liquid supply conduit 446 attached to handle 434 and in fluid communication with lumen 442, and a source of electrically conductive fluid (not shown) for delivering the fluid past return electrode 438 to the target site on the epidermis 440. As discussed above, electrode array 436 is preferably flush with the distal end of shaft 432 or distally extended from the distal end by a small distance (on the order of 0.005 inches) so as to minimize the depth of ablation. Preferably, the distal end of shaft 432 is beveled to improve access and control of probe 430 while treating the epidermal tissue.

Figure 22:
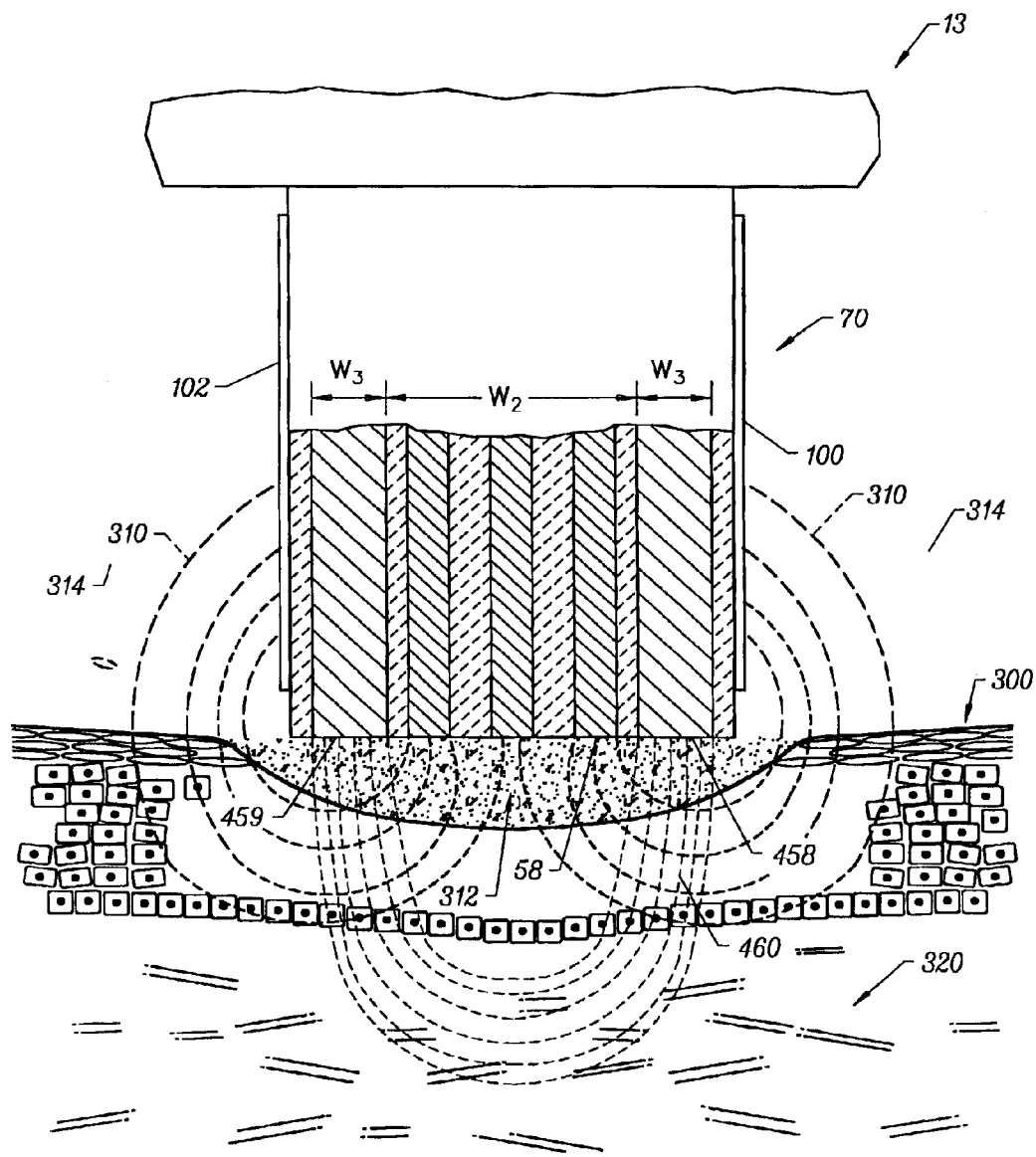
FIG. 22 illustrates another embodiment of the probe of the present invention, incorporating additional electrodes sized for contraction of tissue.

Yet another embodiment of the present invention is shown in FIG. 22. This embodiment is similar to that shown in FIG. 16 and described above, with the exception that additional electrode terminals 458, 459 are positioned at the distal tip 70 of the probe. Electrode terminals 458, 459 may be the same size as ablation electrode terminals 58, larger as shown in FIG. 22. One operating arrangement is to connect electrode terminals 458, 459 to two poles of a high frequency generator to form a bipolar circuit allowing current to flow between terminals 458, 459 as shown by current flux lines 460. The electrode terminals 458, 459 are electrically isolated from ablation electrodes 58. By proper selection of the interelectrode spacing, $W_2$, and electrode width, $W_3$, and the frequency, the current flux lines 460 can be caused to flow below the epidermal layer to effect collagen shrinkage in region 320 as described hereinabove.

In this embodiment, the voltage will preferably be sufficient to establish high electric field intensities between the active electrode array 436 and the epidermal tissue 440 to thereby induce molecular breakdown or disintegration of several cell layers of the epidermal tissue. As described above, a sufficient voltage will be applied to develop a thin layer of vapor within the electrically conductive fluid and to ionize the vaporized layer or region between the active electrode(s) and the target tissue. Energy in the form of photons and/or energetic electrons are discharged from the vapor layer to ablate the epidermal tissue, thereby minimizing necrosis of surrounding tissue and underlying cell layers, such as cell structures in the stratum lucidium and/or stratum granulosum.

Figure 23:
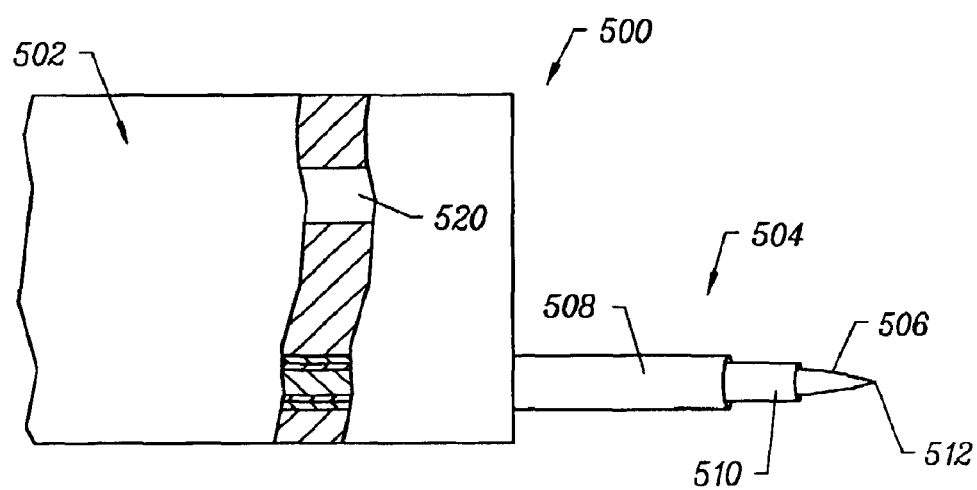
FIG. 23 illustrates another embodiment of the probe of the present invention, specifically designed for creating incisions in external skin surfaces.

FIG. 23 illustrates a distal portion of another electrosurgical probe 500 according to the present invention, particularly useful for cutting or creating incisions in an external skin surface. Probe 500 comprises a support member 502 coupled to a shaft or disposable tip (not shown) as described in previous embodiments. Support member 502 preferably comprises an inorganic electrically insulating material, such as ceramic, glass or glass-ceramic. In this embodiment, however, support member 502 may comprise an organic material, such as plastic, because the active electrode 506 and return electrode 508 are both spaced away from support member 502. Thus, the high intensity electric fields may be far enough away from support member 502 so as to allow an organic material.

An electrode assembly 504 extends from a distal end of support member 502, preferably by a distance of about 2 to 20 mm. Electrode assembly 504 comprises a single, active electrode 506 and a return electrode sleeve 508 spaced proximally from active electrode 506 by an insulation member 510, which preferably comprises an inorganic material, such as ceramic, glass or glass-ceramic. As shown, active electrode 506 preferably tapers to a sharp distal end 512 to facilitate the cutting or incising of tissue. In the exemplary embodiment, active electrode 506 has a proximal diameter of about 0.2 to 20 mm and a distal diameter of less than about 0.2 mm. Return electrode 508 is spaced from active electrode 506 by a sufficient distance to prevent shorting or arcing therebetween at sufficient voltages to allow the volumetric removal of tissue. In the representative embodiment, the distal exposed portion of return electrode 508 is spaced about 0.5 to about 5 mm from the proximal exposed portion of active electrode 506. Of course, it will be recognized that the present invention is not limited to the particular dimensions and configuration of the electrode assembly 504 described herein, and a variety of different embodiments may be envisioned depending on the surgical application.

As shown, probe 500 includes a fluid lumen 520 passing through support member 502 to a distal opening (not shown) at the distal end of support member 502. Fluid lumen 520 is coupled to a supply of electrically conductive fluid, such as isotonic saline, or other suitable conductive fluid for delivery of such fluid to the target site. In the exemplary embodiment, the probe is designed such that lumen 520 will be positioned above electrode assembly 504 during use such that the conductive fluid exiting the distal opening of lumen 520 will naturally pass over return electrode 508 and active electrode 506 thereby creating a current path therebetween. In addition, the conductive fluid will be sufficient to cover the active electrode 506 such that the conditions for plasma formation can be met, as described in detail above.

Figure 24:
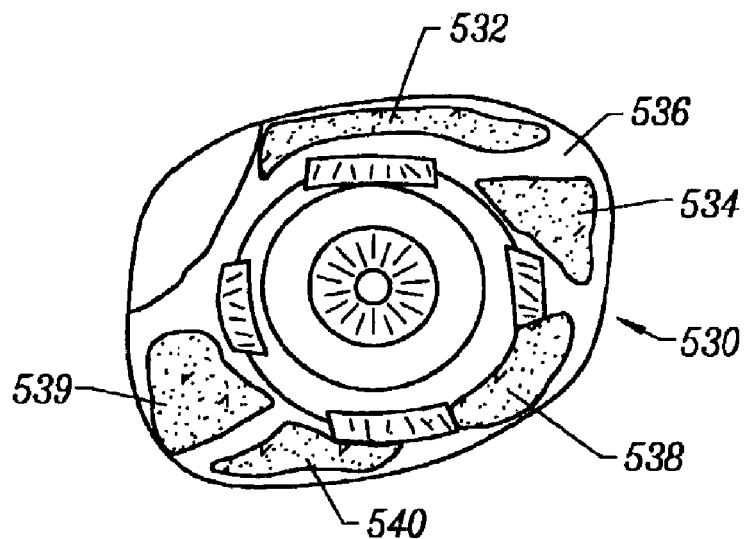
FIGS. 24–26 illustrates a method according to the present invention for removing fatty tissue under the eyelids to treat "baggy eyelids" syndrome.
Figure 25:
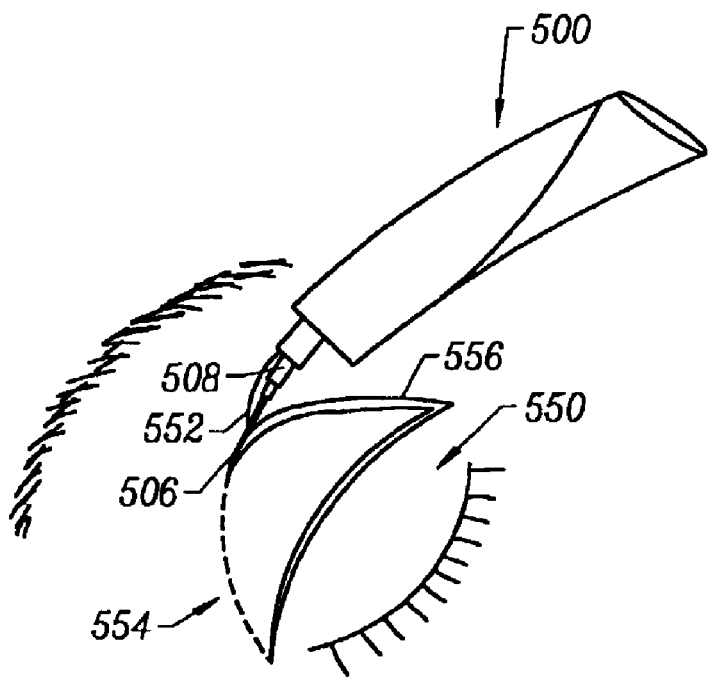
Figure 26:
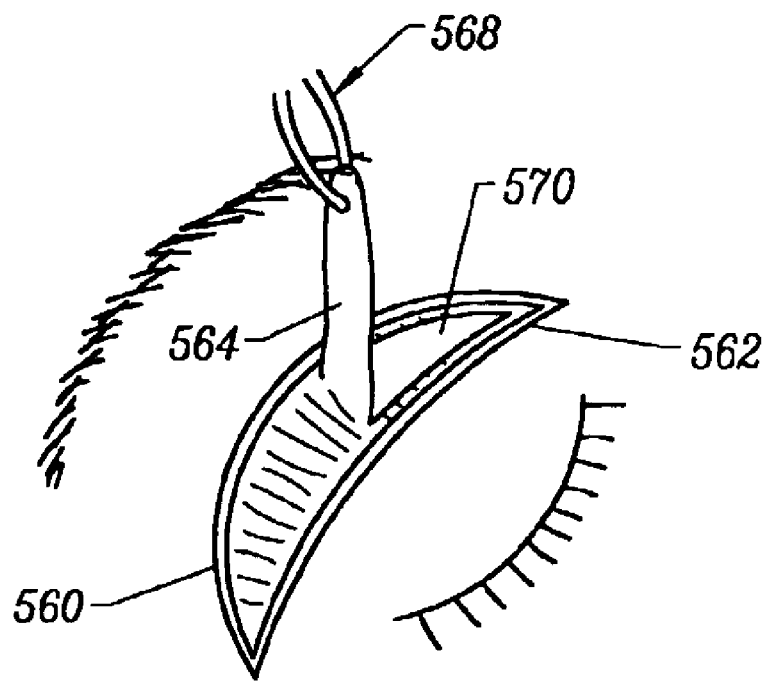

Referring now to FIGS. 24–26, a blepharoplasty procedure for removing fatty tissue underlying a patient's eyelids will now be described according to the present invention. As shown in FIG. 24, a front view of the orbit of the eye 530 reveals the important periocular structures relevant to blepharoplasty surgery. As shown, the two fat compartments of the upper lid, the central and medial compartments 532, 534, are divided by the superior oblique muscle 536. The inferior orbital fat is divided into three compartments, the medial compartment 538, the lateral fat compartment 539 and the central fat compartment 540. Medial fat has more blood vessels and nerves than the other fat compartments in both the upper and lower eyelid. Accordingly, this fat is more sensitive to the application of energy in conventional systems. Depending on the particular procedure, the present invention is designed to facilitate access to these fat compartments of the upper and lower eyelids such that a portion of the fat therein can be removed to treat "baggy eyelids" syndrome.

As shown in FIG. 25, the electrosurgical probe 500 is positioned adjacent the target area, in this case the patient's upper eyelid 550. The power supply is activated such that a high frequency voltage is applied between the active and return electrodes 506, 508 and electrically conductive fluid 552 is delivered to the target area, either by gravity, pump or other means. The surgeon then positions the tip of the active electrode 506 adjacent to or in contact with the external skin 554, and translates the tip across the upper eyelid 550 to form an incision 556 therein. As discussed previously, the high frequency voltage is sufficient to convert the electrically conductive fluid between the target tissue and active electrode 506 into an ionized vapor layer or plasma. As a result of the applied voltage between active electrode 506 and the target tissue (i.e., the voltage gradient across the plasma layer), charged particles in the plasma (viz., electrons) are accelerated towards the tissue. At sufficiently high voltages, these charged particles gain sufficient energy to cause dissociation of the molecular bonds within tissue structures. This molecular dissociation is accompanied by the volumetric removal (i.e., ablative sublimation) of tissue and the production of low molecular weight gases, such as oxygen, nitrogen, carbon dioxide, hydrogen and methane.

As shown in FIG. 26, the surgeon will typically create an upper incision line 560 and a lower incision line 562 to form a crescent shaped flap of skin 564 between the two incision lines 560, 562. The flap of skin 564 is then removed, either completely or by folding it over with a pair of forceps 568, to expose the underlying orbital septum 570. The orbital septum 570 is then pierced with the electrosurgical probe of the present invention or with conventional tools, such as a scalpel, and the underlying fat is excised, e.g., with forceps or other conventional tools. During excision of fat, the probe 500 may be used to effect hemostasis of any severed blood vessels at the surgical site. Once the desired amount of fat tissue has been removed, the surgeon reattaches the flap of skin 564 and cleans up the surgical site.

Other modifications and variations can be made to disclose embodiments without departing from the subject invention as defined in the following claims. For example, FIG. 27 illustrates yet another embodiment designed for cutting of body structures, particularly creating incisions in external skin surfaces. In this embodiment, the electrode terminals 604 are arranged in a linear or columnar array of one of more closely spaced columns so that as the electrodes 604 are moved along the longer axis (denoted by arrow 160 in FIG. 27), the current flux lines are narrowly confined at the tip of the electrode terminals 604 and result in a cutting effect in the body structure being treated. As before, the current flux lines 660 emanating from the electrode terminals 604 pass through the electrically conducting liquid to the return electrode structure 612 located proximal to the probe tip.

Referring now to FIGS. 28 and 29, alternative geometries are shown for the electrode terminals 604. These alternative electrode geometries allow the electrical current densities emanating from the electrode terminals 604 to be concentrated to achieve an increased ablation rate and/or a more concentrated ablation effect due to the fact that sharper edges (i.e., regions of smaller radii of curvature) result in higher current densities. FIG. 28 illustrates a flattened extension of a round wire electrode terminal 604 which results in higher current densities at the edges 680. Another example is shown in FIG. 29 in which the electrode terminal 604 is formed into a cone shaped point 682 resulting in higher current densities at the tip of the cone.

Figure 30:
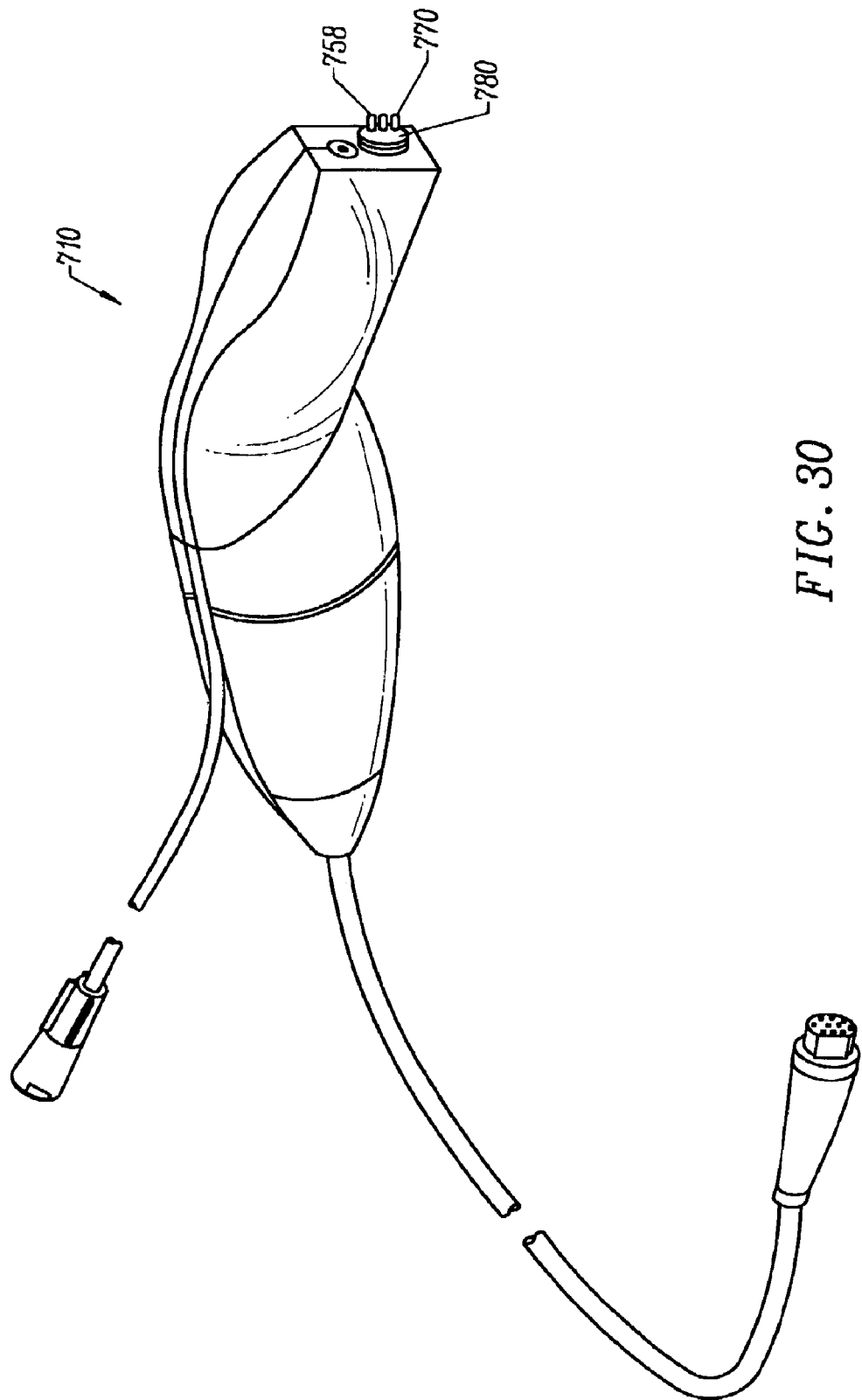
FIG. 30 is a perspective view of another embodiment of an electrosurgical probe for use in dermatology procedures.

FIG. 30 illustrates yet another embodiment of a probe 710 designed for cutting or incising tissue. As shown, in the embodiment, the electrically isolated electrode terminals 758 are spaced apart over a tissue treatment surface 780 of the electrode support member 770, preferably in a linear array. In the representative embodiment, three electrode terminals 758, each having a substantially conical shape, are arranged in a linear array extending distally from surface 780. Electrode terminals 758 will usually extend a distance of about 0.5 to 20 mm from tissue treatment surface 780, preferably about 1 to 5 mm. Applicant has found that this configuration increases the electric field intensities and associated current densities at the distal edges of electrode terminals 758, which increases the rate of tissue cutting. In the representative embodiment, the tissue treatment surface 780 has a circular cross-sectional shape with a diameter in the range of about 0.5 mm to 20 mm (preferably about 2 to 10 mm). The individual electrode terminals 758 preferably taper outward as shown, or they may form a distal edge, such as the electrodes shown in FIG. 28

Figure 31:
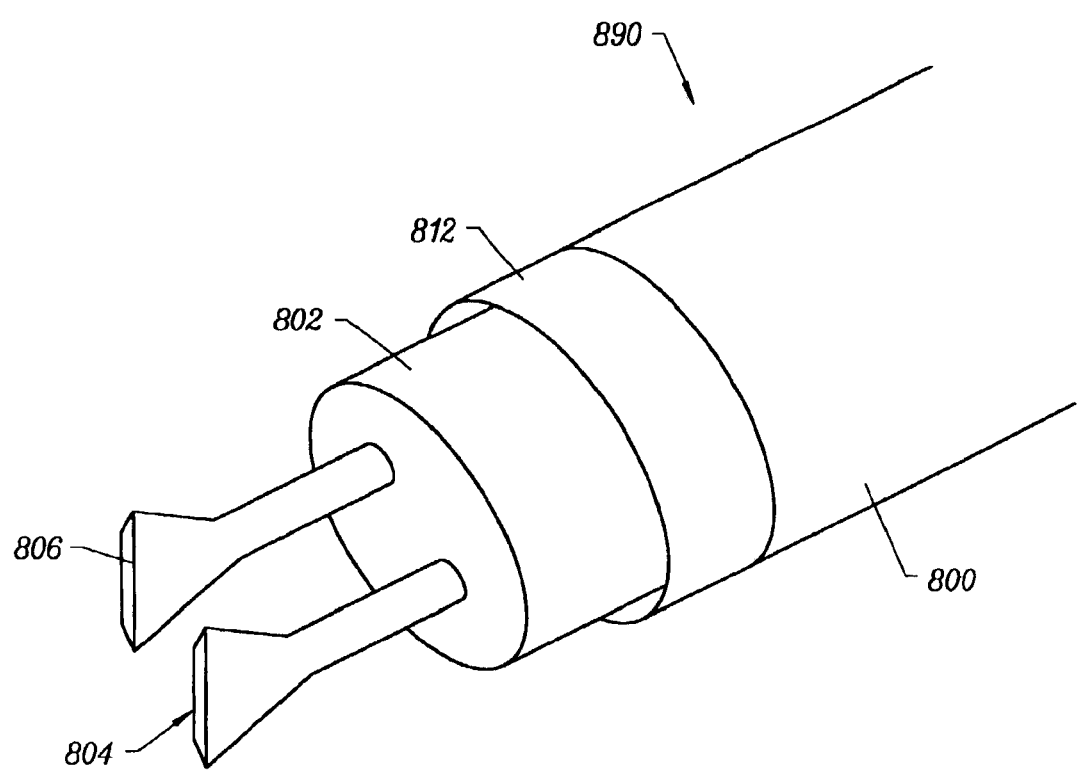
FIG. 31 is a detailed view of the distal portion of yet another electrosurgical probe according to the present invention.

FIG. 31 illustrates an electrosurgical probe 890 comprising a shaft 800 and at least two electrode terminals 804 extending from a support matrix 802 at the distal end of the shaft. The electrode terminals 804 preferably define a distal edge 806 for cutting an incision in tissue. The edges 806 of the electrode terminals 804 are substantially parallel with each other and usually spaced a distance of about 4 to 15 mm, preferably about 8–10 mm. The edges 806 extend from the distal end of support matrix 802 by a distance of about 0.5 to 10 mm, preferably about 2 to 5 mm. In the exemplary embodiment, probe 890 will include a return electrode 812 spaced proximally from the electrode terminals 804. Alternatively, the return electrode 812 may be one of the electrode terminals 804, or it may be a dispersive pad located on an external surface of the patient's body.

Figure 32:
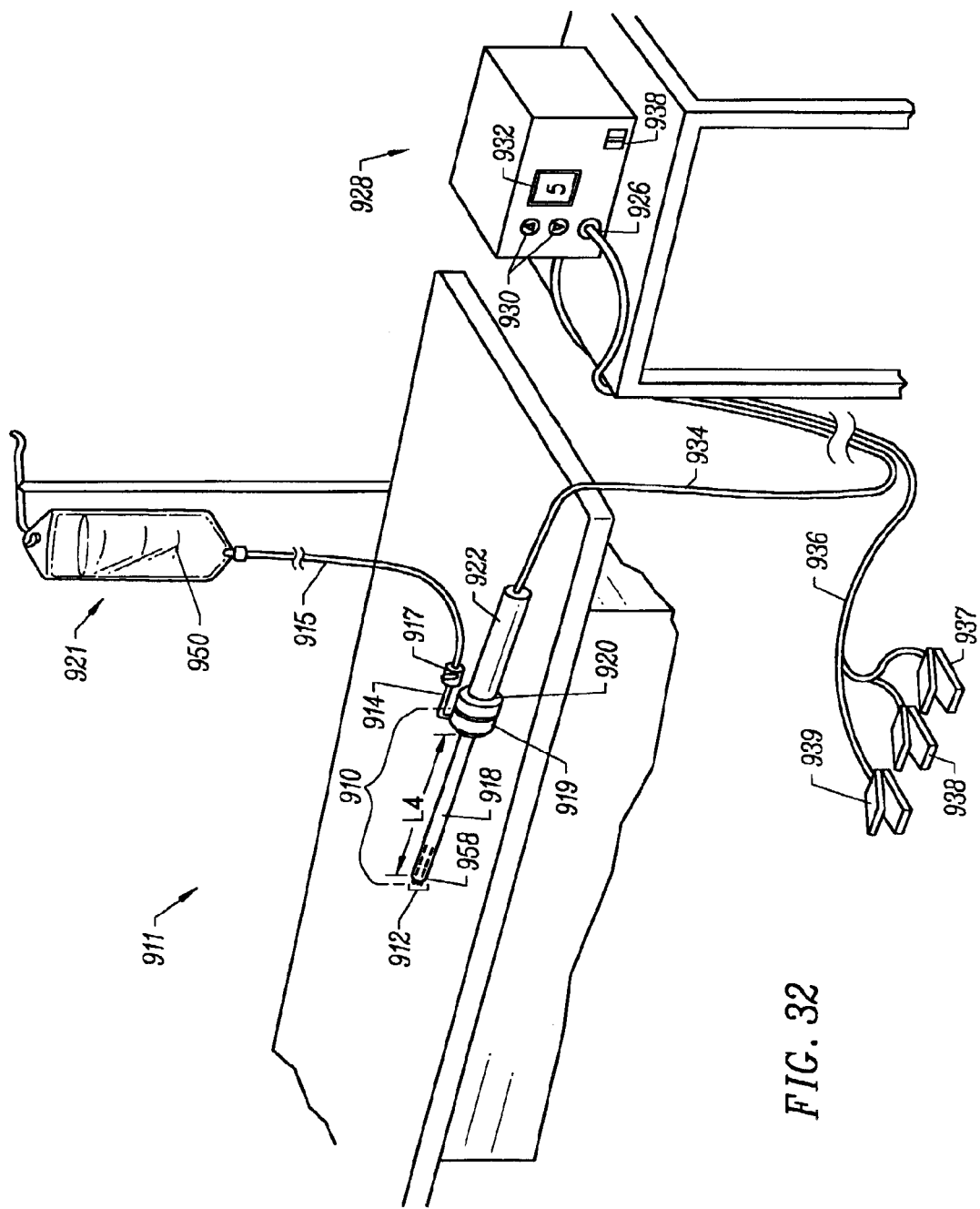
FIG. 32 is a perspective view of another electrosurgical system incorporating a power supply, an electrosurgical probe and a supply of electrically conductive fluid for delivering the fluid to the target site.

Referring now to FIG. 32, an exemplary electrosurgical system 911 for lipectomy procedures will now be described. The system 911 generally applies electrical energy to the fatty tissue to either remove or abate the fatty tissue in situ, soften or separate the fatty tissue from surrounding tissue and then aspirate the fatty tissue fragments from the patient, or a combination thereof. As shown, electrosurgical system 911 generally comprises an electrosurgical handpiece or probe 910 connected to a power supply 928 for providing high frequency voltage to a target site and a fluid source 921 for supplying electrically conductive fluid 950 to probe 910. In addition, electrosurgical system 911 may include an endoscope (not shown) with a fiber optic head light for viewing the surgical site. The endoscope may be integral with probe 910, or it may be part of a separate instrument. The system 911 may also include a vacuum source (not shown) for coupling to a suction lumen or tube 962 (see FIG. 39) in the probe 910 for aspirating excess or unwanted materials from the target site.

As shown, probe 910 generally includes a proximal handle 919 and an elongate shaft 918 having an array 912 of electrode terminals 958 at its distal end. A connecting cable 939 has a connector 926 for electrically coupling the electrode terminals 958 to power supply 928. The electrode terminals 958 are electrically isolated from each other and each of the terminals 958 is connected to an active or passive control network within power supply 928 by means of a plurality of individually insulated conductors (not shown). A fluid supply tube 915 is connected to a fluid tube 914 of probe 910 for supplying electrically conductive fluid 950 to the target site.

Similar to the above embodiment, power supply 928 has an operator controllable voltage level adjustment 930 to change the applied voltage level, which is observable at a voltage level display 932. Power supply 928 also includes first, second and third foot pedals 937, 938, 939 and a cable 936 which is removably coupled to power supply 928. The foot pedals 37, 38, 39 allow the surgeon to remotely adjust the energy level applied to electrode terminals 958.

Figure 33:
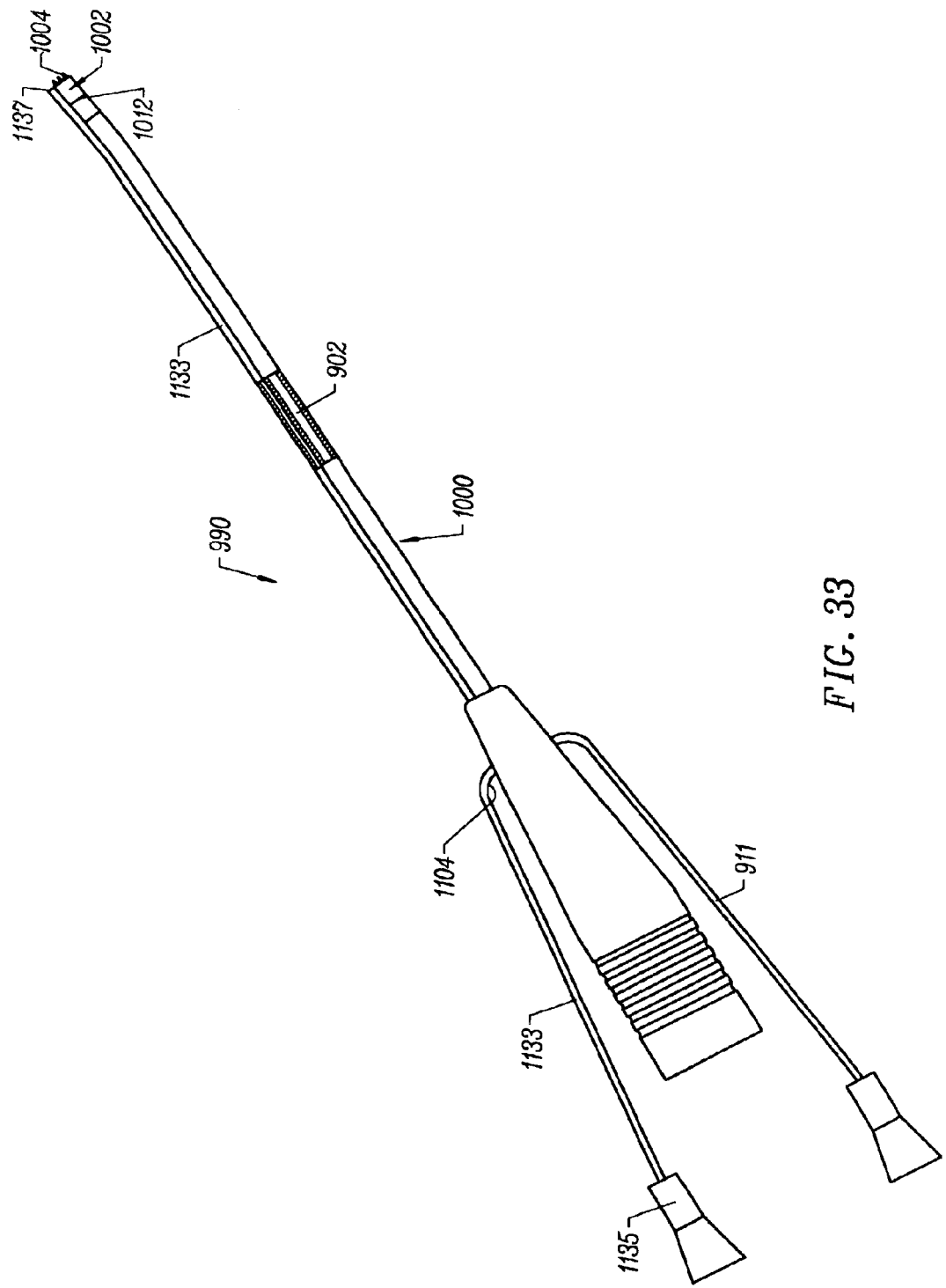
FIG. 33 is a side view of another electrosurgical probe according to the present invention incorporating aspiration electrodes for ablating aspirated tissue fragments and/or tissue strands, such as adipose tissue.
Figure 34:
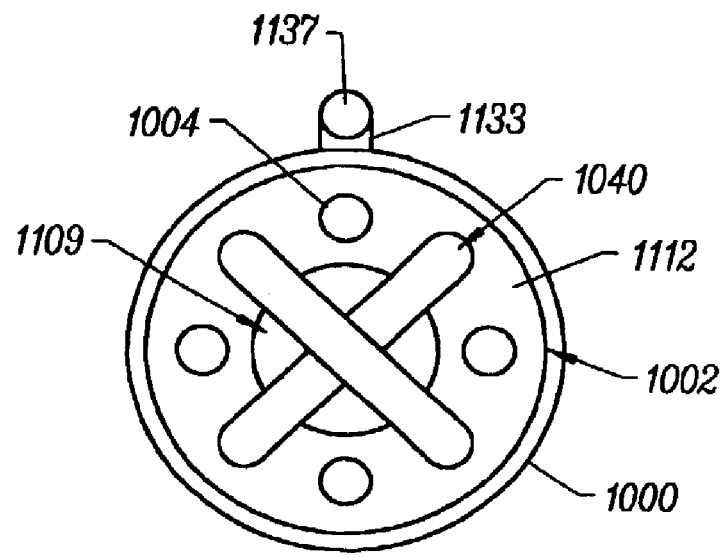
FIG. 34 is an end view of the probe of FIG. 33.
Figure 35:
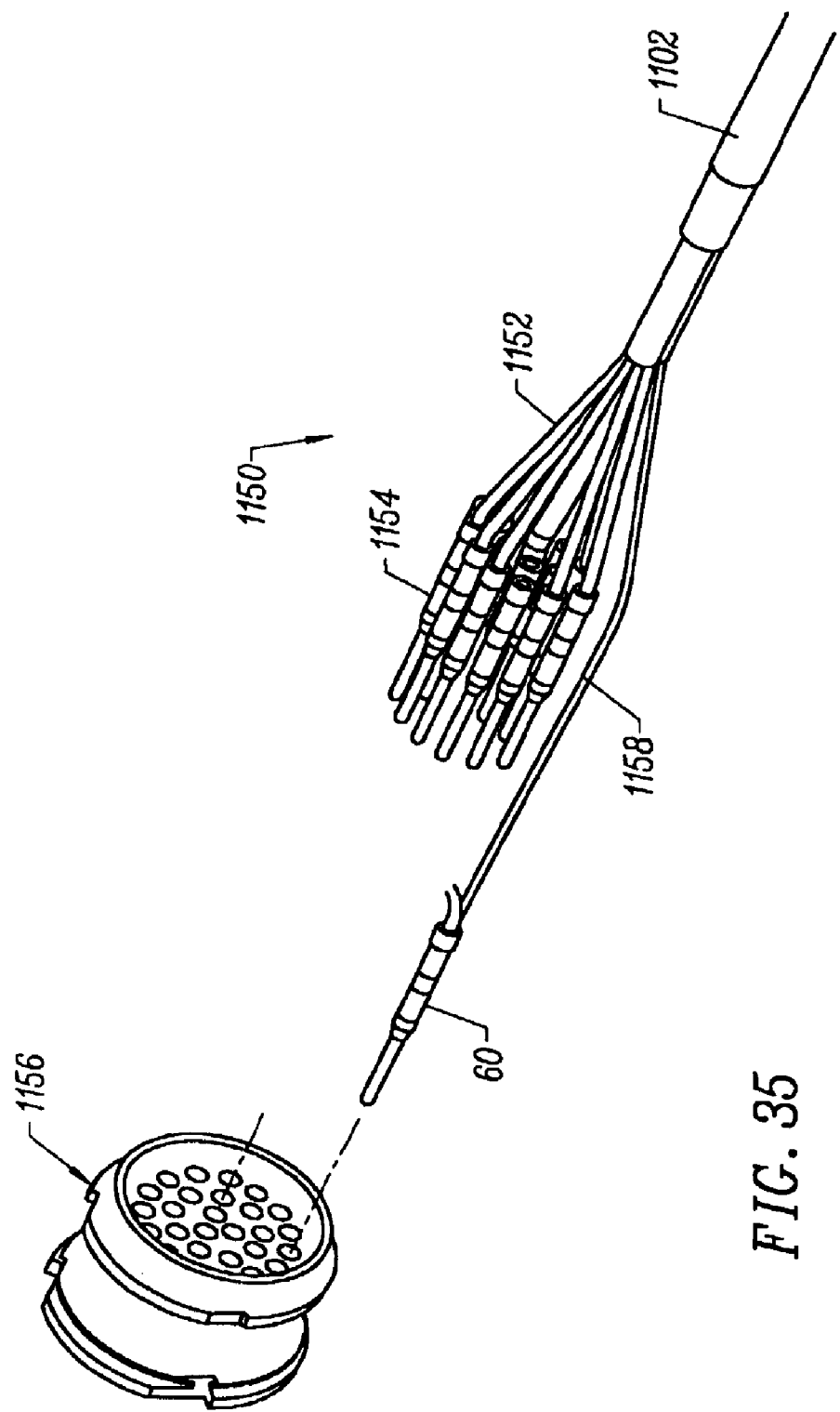
FIG. 35 is an exploded view of a proximal portion of the electrosurgical probe.

FIGS. 33–35 illustrate an exemplary electrosurgical probe 990 constructed according to the principles of the present invention. As shown in FIG. 33, probe 990 generally includes an elongated shaft 1000 which may be flexible or rigid, a handle 1104 coupled to the proximal end of shaft 1000 and an electrode support member 1002 coupled to the distal end of shaft 1000. In an alternative embodiment (not shown), shaft 1000 comprises an electrically conducting material, usually metal, which is selected from the group comprising tungsten, stainless steel alloys, platinum or its alloys, titanium or its alloys, molybdenum or its alloys, and nickel or its alloys. In this embodiment, shaft 1000 includes an electrically insulating jacket 1008, which is typically formed as one or more electrically insulating sheaths or coatings, such as polytetrafluoroethylene, polyimide, and the like. The provision of the electrically insulating jacket over the shaft prevents direct electrical contact between these metal elements and any adjacent body structure or the surgeon. Such direct electrical contact between a body structure (e.g., tendon) and an exposed electrode could result in unwanted heating of the structure at the point of contact causing necrosis.

Handle 1104 typically comprises a plastic material that is easily molded into a suitable shape for handling by the surgeon. Handle 1104 defines an inner cavity (not shown) that houses the electrical connections 1150 (FIG. 35), and provides a suitable interface for connection to an electrical connecting cable 934 (see FIG. 32). Electrode support member 1002 extends from the distal end of shaft 1000 (usually about 1 to 20 mm), and provides support for a plurality of electrically isolated electrode terminals 1004 (see FIG. 34). As shown in FIG. 33, a fluid tube 1133 extends through an opening in handle 1104, and includes a connector 1135 for connection to a fluid supply source, for supplying electrically conductive fluid to the target site. Depending on the configuration of the distal surface of shaft 1000, fluid tube 1133 may extend through a single lumen (not shown) in shaft 1000, or it may be coupled to a plurality of lumens (also not shown) that extend through shaft 1000 to a plurality of openings at its distal end. In the representative embodiment, fluid tube 1133 extends along the exterior of shaft 1000 to a point just proximal of return electrode 1012 (see FIG. 33). In this embodiment, the fluid is directed through an opening 1137 past return electrode 1012 to the electrode terminals 1004. Probe 990 may also include a valve 917 (FIG. 32) or equivalent structure for controlling the flow rate of the electrically conductive fluid to the target site.

As shown in FIG. 33–35, the distal portion of shaft 1000 is preferably bent to improve access to the operative site of the tissue being treated. Electrode support member 1002 has a substantially planar tissue treatment surface 1112 that is usually at an angle of about 10 to 90 degrees relative to the longitudinal axis of shaft 1100, preferably about 30 to 60 degrees and more preferably about 45 degrees. In alternative embodiments, the distal portion of shaft 1000 comprises a flexible material which can be deflected relative to the longitudinal axis of the shaft. Such deflection may be selectively induced by mechanical tension of a pull wire, for example, or by a shape memory wire that expands or contracts by externally applied temperature changes. A more complete description of this embodiment can be found in commonly assigned U.S. Pat. No. 5,697,909, the complete disclosure of which is incorporated herein by reference for all purposes.

In the embodiment shown in FIGS. 33–35, probe 990 includes a return electrode 1012 for completing the current path between electrode terminals 1004 and a high frequency power supply 928 (see FIG. 32). As shown, return electrode 1012 preferably comprises an annular conductive band coupled to the distal end of shaft 1000 slightly proximal to tissue treatment surface 1112 of electrode support member 1002, typically about 0.05 to 10 mm and more preferably about 1 to 10 mm. Return electrode 1012 is coupled to a connector 1158 that extends to the proximal end of probe 910, where it is suitably connected to power supply 928.

As shown in FIG. 33, return electrode 1012 is not directly connected to electrode terminals 1004. To complete this current path so that electrode terminals 1004 are electrically connected to return electrode 1012, electrically conductive fluid (e.g., isotonic saline) is caused to flow therebetween. In the representative embodiment, the electrically conductive fluid is delivered through fluid tube 1133 to opening 1137, as described above. Alternatively, the fluid may be delivered by a fluid delivery element (not shown) that is separate from probe 990. Electrically conductive fluid will be continually resupplied to maintain the conduction path between return electrode 1012 and electrode terminals 1004.

In alternative embodiments, the electrically conductive fluid may be delivered to the working end of probe 990 by, for example, an inner lumen or an annular gap between the return electrode and a tubular support member within shaft 1000. This annular gap may be formed near the perimeter of the shaft 1000 such that the electrically conductive fluid tends to flow radially inward towards the target site, or it may be formed towards the center of shaft 1000 so that the fluid flows radially outward. In both of these embodiments, a fluid source (e.g., a bag of fluid elevated above the surgical site or having a pumping device), is coupled to probe 990 via a fluid supply tube (not shown) that may or may not have a controllable valve. A more complete description of an electrosurgical probe incorporating one or more fluid lumen(s) can be found in U.S. Pat. No. 5,697,281, the complete disclosure of which has previously been incorporated herein by reference.

Referring to FIG. 34, the electrically isolated electrode terminals 1004 are spaced apart over tissue treatment surface 1112 of electrode support member 1002. The tissue treatment surface and individual electrode terminals 1004 will usually have dimensions within the ranges set forth above. As shown, the probe includes a single, larger opening 1109 in the center of tissue treatment surface 1112, and a plurality of electrode terminals (e.g., about 3–15) around the perimeter of surface 1112. Alternatively, the probe may include a single, annular, or partially annular, electrode terminal at the perimeter of the tissue treatment surface. The central opening 1109 is coupled to a suction lumen (not shown) within shaft 1000 and a suction tube 1111 (or lumen) for aspirating tissue, fluids and/or gases from the target site. In this embodiment, the electrically conductive fluid generally flows radially inward past electrode terminals 1004 and then back through the opening 1109. Aspirating the electrically conductive fluid during surgery allows the surgeon to see the target site, and it prevents the fluid from flowing into the patient's body.

As shown in FIG. 34, one or more of the electrode terminals comprise loop electrodes 1040 that extend across distal opening 1109 of the suction lumen within shaft 1000.

In the representative embodiment, two of the electrode terminals comprise loop electrodes 1040 that cross over the distal opening 1109. Of course, it will be recognized that a variety of different configurations are possible, such as a single loop electrode, or multiple loop electrodes having different configurations than shown. In addition, the electrodes may have shapes other than loops, such as the coiled configurations shown in FIGS. 36 and 37. Alternatively, the electrodes may be formed within the suction lumen proximal to the distal opening 1109, as shown in FIG. 38. The main function of loop electrodes 1040 is to ablate portions of tissue that are drawn towards or into the suction lumen to prevent clogging of the lumen.

Loop electrodes 1040 are electrically isolated from the other electrode terminals 1004, which can be referred to hereinafter as the ablation electrodes 1004. Loop electrodes 1040 may or may not be electrically isolated from each other. Loop electrodes 1040 will usually extend only about 0.05 to 4 mm, preferably about 0.1 to 1 mm from the tissue treatment surface of electrode support member 1004.

Of course, it will be recognized that the distal tip of probe may have a variety of different configurations. For example, the probe may include a plurality of openings 1109 around the outer perimeter of tissue treatment surface 1112. In this embodiment, the electrode terminals 1004 extend from the center of tissue treatment surface 1112 radially inward from openings 1109. The openings are suitably coupled to fluid tube 1133 for delivering electrically conductive fluid to the target site, and a suction tube 1111 for aspirating the fluid after it has completed the conductive path between the return electrode 1012 and the electrode terminals 1004. In this embodiment, the ablation electrode terminals 1004 are close enough to openings 1109 to ablate most of the large tissue fragments that are drawn into these openings.

FIG. 35 illustrates the electrical connections 1150 within handle 1104 for coupling electrode terminals 1004 and return electrode 1012 to the power supply 928. As shown, a plurality of wires 1152 extend through shaft 1000 to couple terminals 1004 to a plurality of pins 1154, which are plugged into a connector block 1156 for coupling to a connecting cable 922 (FIG. 32). Similarly, return electrode 1012 is coupled to connector block 1156 via a wire 1158 and a plug 1160.

Figure 36:
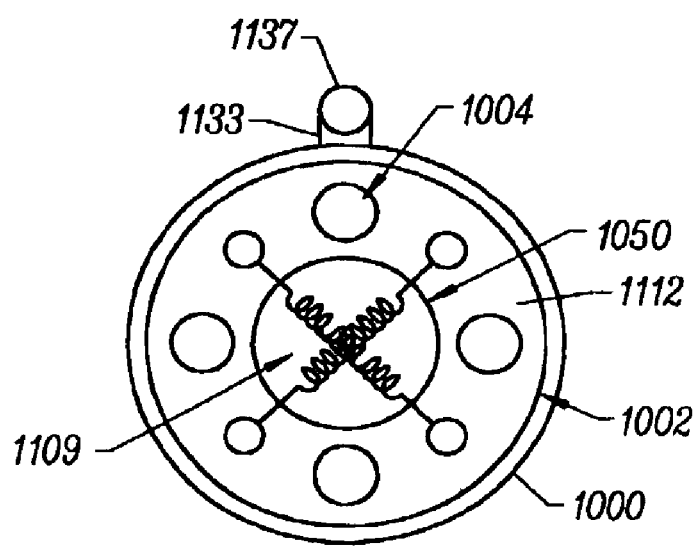
FIGS. 36–38 illustrate alternative probes according to the present invention, incorporating aspiration electrodes.
Figure 37:
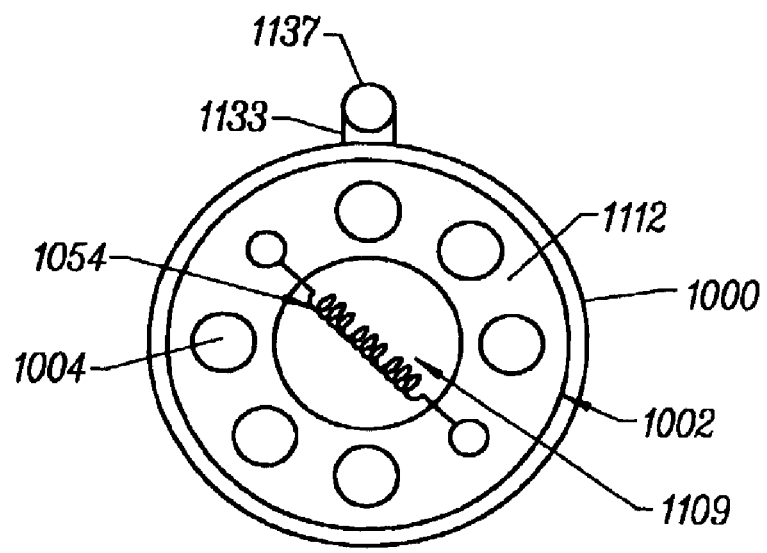
Figure 38:
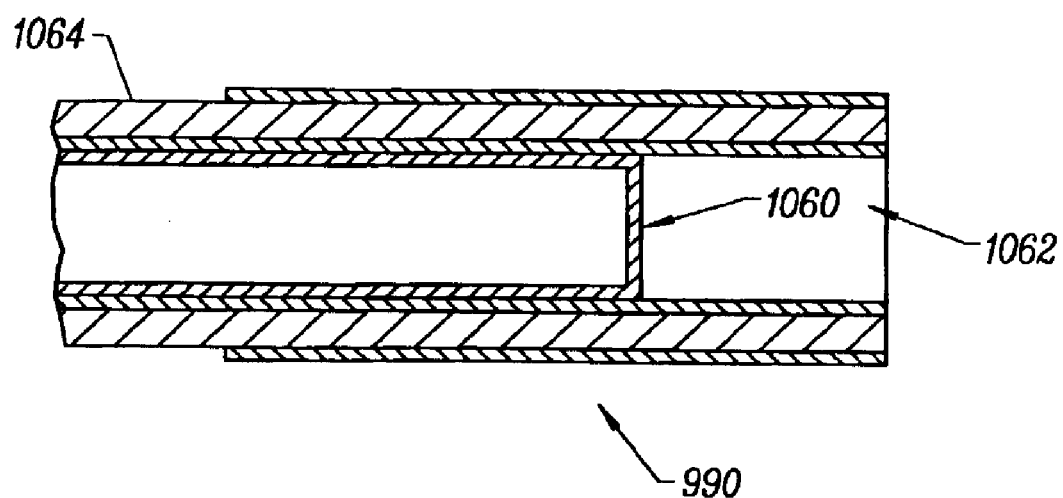

Referring now to FIGS. 36 and 37, alternative embodiments for aspiration electrodes will now be described. As shown in FIG. 36, the aspiration electrodes may comprise a pair of coiled electrodes 1050 that extend across distal opening 1109 of the suction lumen. The larger surface area of the coiled electrodes 1050 usually increases the effectiveness of the electrodes 1050 on tissue fragments passing through opening 1109. In FIG. 37, the aspiration electrode comprises a single coiled electrode 1052 passing across the distal opening 1109 of suction lumen. This single electrode 1052 may be sufficient to inhibit clogging of the suction lumen. Alternatively, the aspiration electrodes may be positioned within the suction lumen proximal to the distal opening 1109. Preferably, these electrodes are close to opening 1109 so that tissue does not clog the opening 1109 before it reaches electrodes 1054. In this embodiment, a separate return electrode 1056 may be provided within the suction lumen to confine the electric currents therein.

Referring to FIG. 38, another embodiment of the present invention incorporates an aspiration electrode 1060 within the aspiration lumen 1062 of the probe. As shown, the electrode 1060 is positioned just proximal of distal opening 1109 so that the tissue fragments are ablated as they enter lumen 1062. In the representation embodiment, the aspiration electrode 1060 comprises a loop electrode that stretches across the aspiration lumen 1062. However, it will be recognized that many other configurations are possible. In this embodiment, the return electrode 1064 is located outside of the probe as in the previously embodiments. Alternatively, the return electrode(s) may be located within the aspiration lumen 1062 with the aspiration electrode 1060. For example, an inner insulating coating may be exposed at portions within the lumen 1062 to provide a conductive path between this exposed portion of return electrode 1064 and the aspiration electrode 1060. The latter embodiment has the advantage of confining the electric currents to within the aspiration lumen. In addition, in dry fields in which the conductive fluid is delivered to the target site, it is usually easier to maintain a conductive fluid path between the active and return electrodes in the latter embodiment because the conductive fluid is aspirated through the aspiration lumen 1062 along with the tissue fragments.

Figure 39:
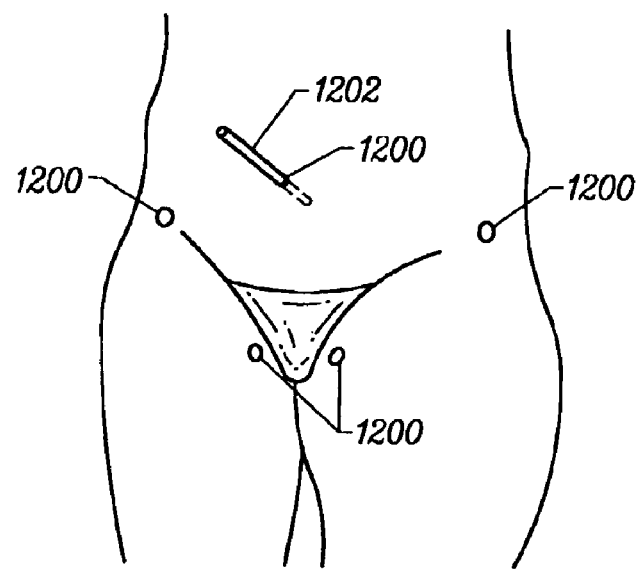
FIG. 39 illustrates a method for removing fatty tissue in the abdomen, groin or thighs region of a patient according to the present invention.

FIG. 39 schematically illustrates a lipectomy procedure in the abdomen according to the present invention. Liposuction in the abdomen, lower torso and thighs according to the present invention removes excess adipose tissue from these regions while leaving the fascial, neurovascular, and lymphatic network intact or only mildly compromised. As shown, access incisions 1200 are typically positioned in natural skin creases remote from the areas to be liposuctioned.

In a conventional liosuction procedure of the prior art, multiple incisions may be made to allow cross-tunneling, and the surgeon manipulates the suction cannula in a linear piston-like motion during suction to remove the adipose tissue to avoid clogging of the cannula, and to facilitate separation of the fatty tissue from the remaining tissue. The present invention largely solves these two problems and, therefore, minimizes the need for the surgeon to manipulate the probe in such a fashion.

As shown in FIG. 39, the distal portion (not shown) of an electrosurgical instrument 1202 is introduced through one or more of the incisions 1200 and one or more electrode terminal(s) 1004 (FIG. 33) are positioned adjacent to the adipose tissue to be removed. Electrically conductive fluid, e.g., isotonic saline, is delivered through tube 1133 and opening 1137 (e.g., FIG. 33) to the tissue. The fluid flows past the return electrode 1012 to the electrode terminals 1004 at the distal end of the shaft. The rate of fluid flow is controlled with valve 917 (FIG. 32) such that the zone between the tissue and electrode support 1002 is constantly immersed in the fluid. The power supply 928 is then turned on and adjusted such that a high frequency voltage is applied between electrode terminals 1004 and return electrode 1012. The electrically conductive fluid provides a current flow path between electrode terminals 1004 and the return electrode 1012.

In one embodiment, the high frequency voltage is sufficient to convert the electrically conductive fluid (not shown) between the target tissue and electrode terminals 1004 into an ionized vapor layer or plasma (not shown). As a result of the applied voltage between electrode terminal(s) 1004 and the target tissue (i.e., the voltage gradient across the plasma layer), charged particles in the plasma (e.g., electrons) are accelerated towards the fatty tissue. At sufficiently high voltages, these charged particles gain sufficient energy to cause dissociation of the molecular bonds within tissue structures. This molecular dissociation is accompanied by the volumetric removal (i.e., ablative sublimation) of tissue and the production of low molecular weight gases, such as oxygen, nitrogen, carbon dioxide, hydrogen and methane.

In alternative embodiments of the invention, the high frequency voltage is sufficient to heat and soften or separate portions of the fatty tissue from the surrounding tissue. Suction is then applied from a vacuum source (not shown) through lumen 962 to aspirate or draw away the heated fatty tissue. A temperature of about 45° C. softens fatty tissue, and a temperature of about 50° C. tends to liquefy ordinary fat in adipose tissue. This heating and softening of the fatty tissue reduces the collateral damage created when the heated tissue is then removed by aspiration. Alternatively, the present invention may employ a combination of ablation through molecular dissociation, as described above, and heating or softening of the fatty tissue. In this embodiment, some of the fatty tissue is ablated in situ, while other portions are softened to facilitate removal by suction.

During the procedure, gases may be aspirated through opening 1109 and suction tube 1111 to a vacuum source. In addition, excess electrically conductive fluid, and other fluids (e.g., blood) are also aspirated from the target site to facilitate the surgeon's view. Applicant has also found that tissue fragments are also aspirated through opening 1109 into suction lumen and tube 1111 during the procedure. These tissue fragments may be ablated or dissociated with loop electrodes 1040 via a mechanism similar to that described above. Namely, as electrically conductive fluid and tissue fragments are aspirated into loop electrodes 1040, these electrodes are activated so that high frequency voltage is applied to loop electrodes 1040 and return electrode 1012 (of course, the probe may include a different, separate return electrode for this purpose). The voltage is sufficient to vaporize electrically conductive fluid, and to create a plasma layer between loop electrodes 1040 and the tissue fragments so that portions of the tissue fragments are ablated or removed. This reduces the volume of the tissue fragments as they pass through suction lumen to minimize clogging of the lumen.

In one embodiment, loop electrodes 1040 are electrically isolated from the other electrode terminals 1004, and they must be separately activated at the power supply 928. In other embodiments, loop electrodes 1040 will be activated at the same time that electrode terminals 1004 are activated. In this case, applicant has found that the plasma layer typically forms when tissue is drawn adjacent to loop electrodes 1040.

Figure 40:
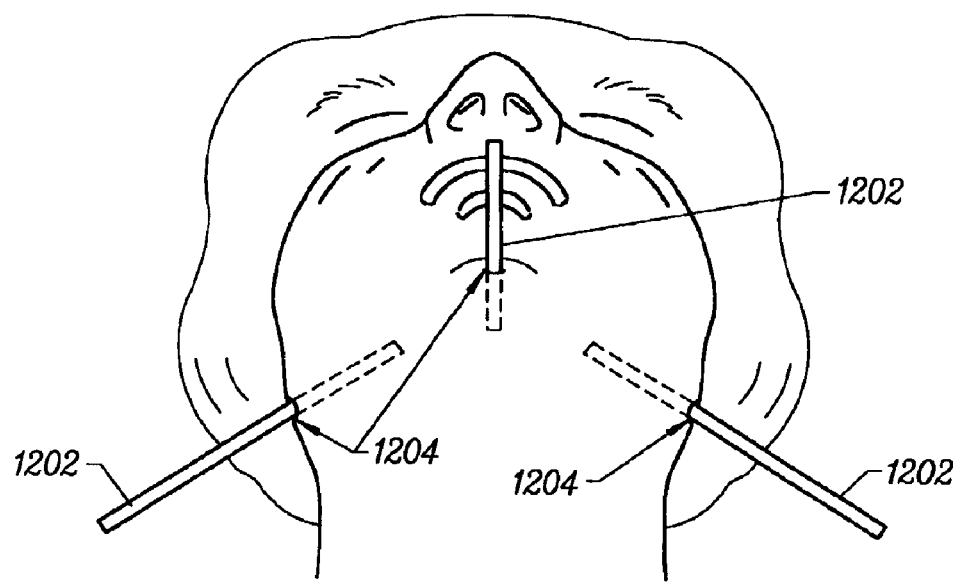
FIG. 40 illustrates a method for removing fatty tissue in the head and neck region of a patient according to the present invention.

FIG. 40 illustrates a cervical liposuction procedure in the face and neck according to the present invention. As shown, the distal portion of the electrosurgical probe 1202 may be inserted in either submental or retroauricular incisions 1204 in the face and neck. In this procedure, the probe 1202 is preferably passed through a portion of the fatty tissue with the power supply 928 activated, but without suction, to establish a plane of dissection at the most superficial level of desired fat removal. This plane of dissection allows a smooth, supple, redraping of the region after liposuction has been completed. If this "pretunneling" is not performed in this region, the cannula has a tendency to pull the skin inward, creating small pockets and indentations in the skin, which becomes evident as superficial irregularities after healing. Pretunneling also enables accurate, safe and proper removal of fat deposits, while preserving a fine cushion of subdermal fat.

The present invention may also be used to perform lipectomies in combination with face and neck lifts to facilitate the latter procedures. After the cervical liposuction is complete, the skin flaps are elevated in the temporal, cheek and lateral regions. The lateral neck skin flap dissection is greatly facilitated by the previous suction lipectomy in that region, and the medial and central skin flap elevation may be virtually eliminated.

Figure 41:
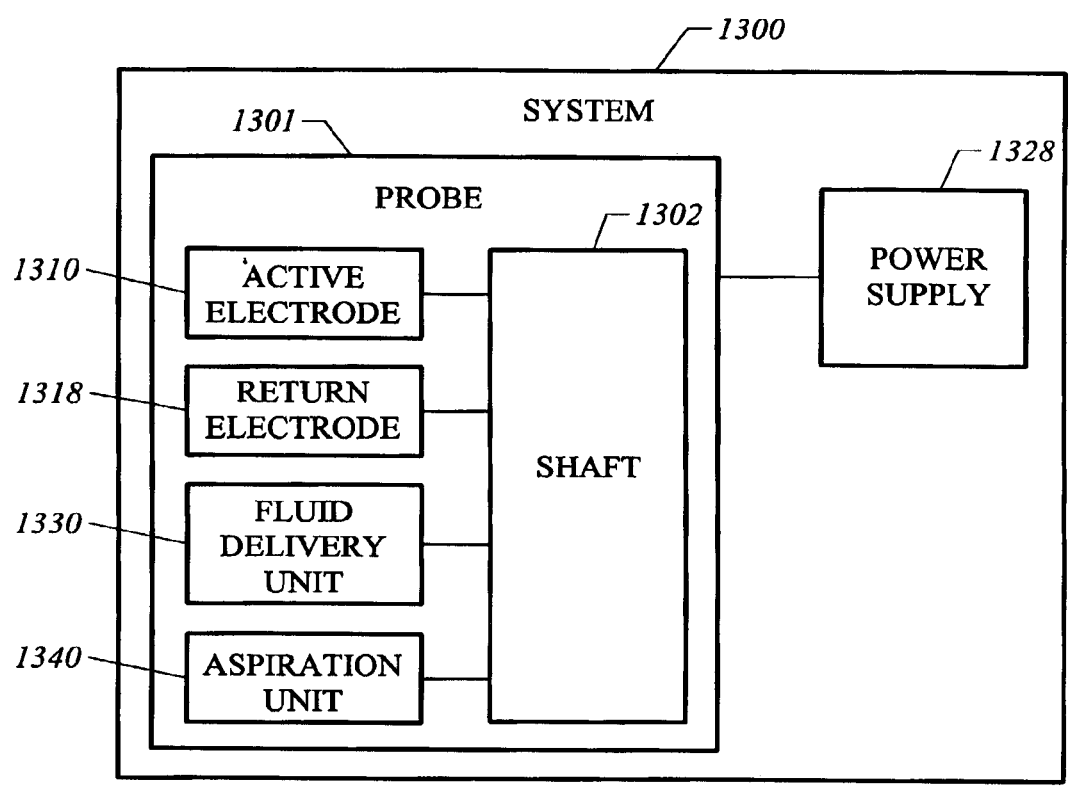
FIG. 41 is a block diagram representing an electrosurgical system, according to one aspect of the invention.

FIG. 41 is a block diagram representing an electrosurgical system 1300, according to one aspect of the instant invention. System 1300 includes an electrosurgical probe 1301 coupled to a high frequency power supply 1328. Probe 1301 includes a shaft 1302, an active electrode 1310, and a return electrode 1318. Typically, active electrode 1310 and return electrode 1318 are disposed at the distal or working end of shaft 1302 (e.g., FIGS. 43, 44A–C). Shaft 1302 may be straight (linear), rigid, curved, flexible, or steerable (e.g., FIGS. 45A–B). In use, power supply 1328 may be used to apply a high frequency voltage between active electrode 1310 and return electrode 1318 at a pre-selected voltage level and frequency. System 1300 is adapted for operation in the sub-ablation mode (e.g., for the contraction, shrinkage, or other modification of tissue in the absence, or substantial absence, of ablation). Typically, system 1300 is further adapted for operation in the ablation mode (e.g., for the ablation, volumetric removal, or vaporization of tissue). System 1300 may be switched or toggled between the sub-ablation mode and the ablation mode, e.g., via foot pedals (FIG. 1). Probe 1301 further includes a fluid delivery unit 1330 for delivering an electrically conductive fluid to the working or distal end of probe 1301, and an aspiration unit 1340 for removing unwanted or excess materials from the surgical site during a procedure.

Figure 42:
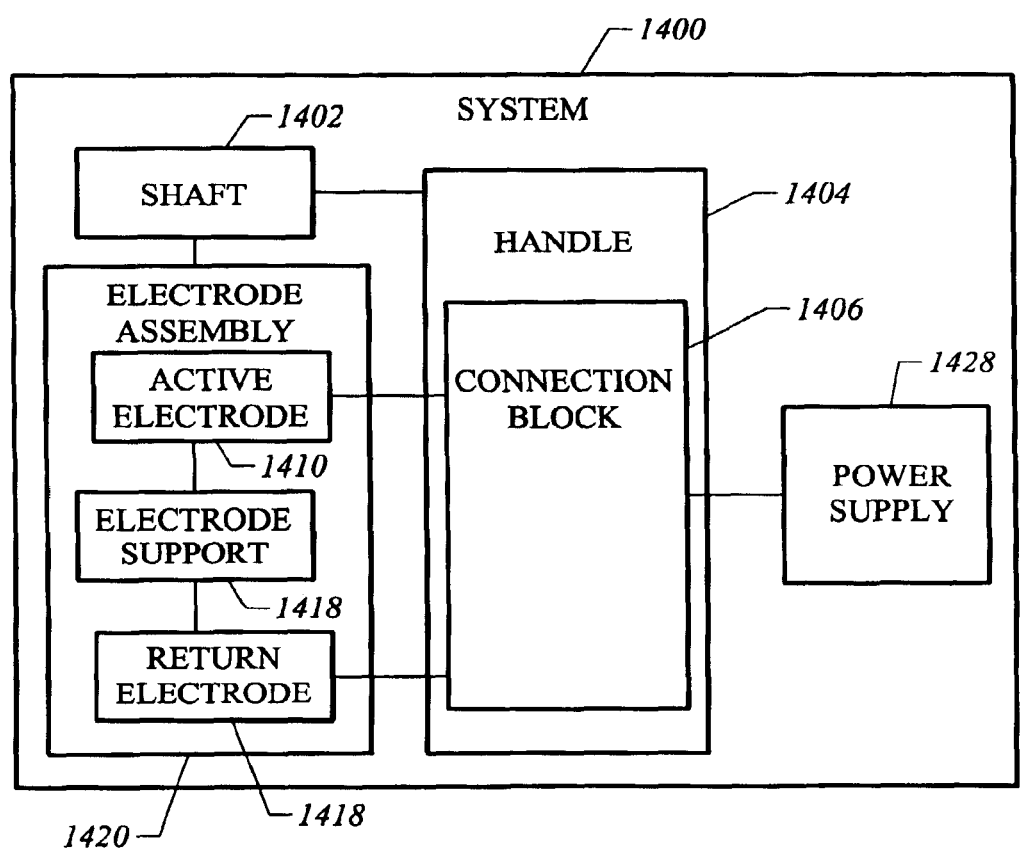
FIG. 42 is a block diagram representing an electrosurgical system, according to the instant invention.

FIG. 42 is a block diagram representing an electrosurgical system 1400, according to the instant invention. System 1400 includes a shaft 1402, and an electrode assembly 1420 disposed on shaft 1402. Electrode assembly 1420 includes an electrode support 1414, an active electrode 1410 disposed on electrode support 1414, and a return electrode 1418 spaced from active electrode 1410 by electrode support 1414. System 1400 further includes a handle 1404 housing a connection block 1406, and a high frequency power supply 1428. Active electrode 1410 and return electrode 1418 are coupled to power supply 1428 via connection block 1406. Power supply 1428 is adapted for applying a high frequency voltage between active electrode 1410 and return electrode 1418 in, at least, the sub-ablation mode (essentially as described hereinabove for power supply 1328, FIG. 41). System 1400 may be used in conjunction with a fluid delivery unit and an aspiration unit (essentially as described hereinabove with reference to system 1300, FIG. 41).

Figure 43:
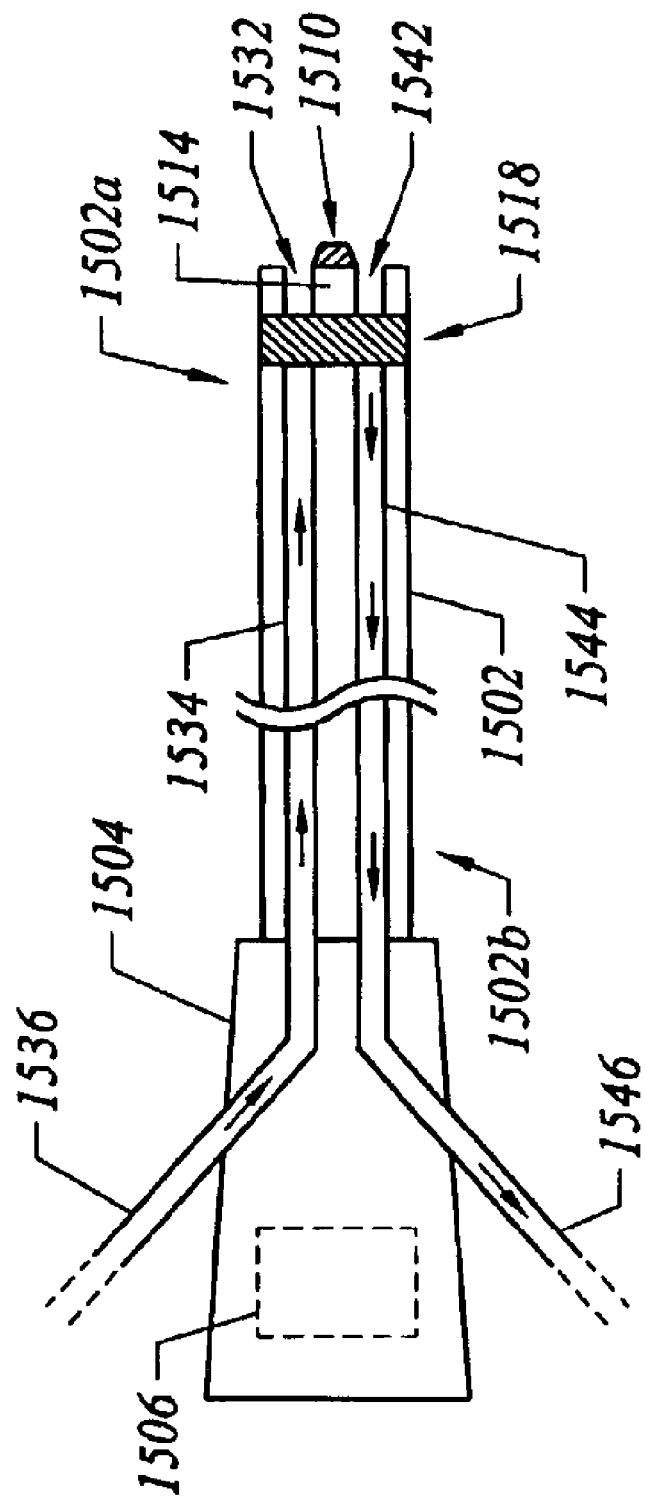
FIG. 43 is a partial sectional view of an electrosurgical probe, according to one embodiment of the invention.

FIG. 43 is a partial sectional view of an electrosurgical probe 1500, according to one embodiment of the instant invention. Probe 1500 includes a shaft 1502, having a shaft distal end 1502a and a shaft proximal end 1502b, and a handle 1504 affixed to proximal end 1502b. Handle 1504 houses a connection block 1506. Probe 1500 further includes an active electrode 1510 and a return electrode 1518. Active electrode 1510 and return electrode 1518 are typically coupled to connection block 1506 via leads, wires, or filaments (not shown in FIG. 43). Connection block 1506 provides a convenient mechanism for the facile and reliable coupling of active electrode 1510 and return electrode 1518 to a high frequency power supply (e.g., FIG. 42). As shown, active electrode 1510 is disposed at the distal terminus of probe 1500 on an electrically insulating electrode support 1514. Return electrode 1518 is spaced proximally from active electrode 1510 by electrode support 1514. In one embodiment, shaft 1502 comprises a metal tube partially ensheathed within an electrically insulating sleeve, and return electrode 1518 comprises an exposed (non-insulated) portion of shaft 1502.

Again with reference to FIG. 43, probe 1500 further includes an integral fluid delivery unit and an integral aspiration unit. The fluid delivery unit includes a distal fluid delivery port 1532, a fluid delivery lumen 1534, and a proximal fluid delivery tube 1536. Fluid delivery tube 1536 may be coupled to a suitable source of an electrically conductive fluid (e.g., FIG. 1). The electrically conductive fluid delivered to the working end of the probe provides a current flow path between active electrode 1510 and return electrode 1518. The flow rate of electrically conductive fluid (represented in FIG. 43 by solid arrows) may be controlled by one or more pumps, valves, or other functionally analogous devices.

The aspiration unit of probe 1500 includes a distal aspiration port 1542, an aspiration lumen 1544, and a proximal aspiration tube 1546. Aspiration tube 1546 may be coupled to a suitable vacuum source (not shown) in order to draw an aspiration stream from port 1542 through lumen 1544. Excess or unwanted materials (e.g., ablation by-products, tissue fragments, etc.) may be removed from the surgical site via the aspiration stream. The flow rate of the aspiration stream (represented in FIG. 43 by open arrows) may be controlled by a valve or similar element.

Figure 44A:
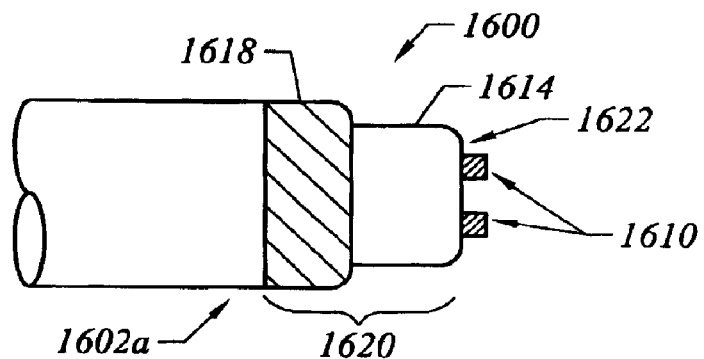
FIGS. 44A–C each show a side view of the working end of an electrosurgical probe having a distal electrode assembly, according to three different embodiments of the invention.
Figure 44B:
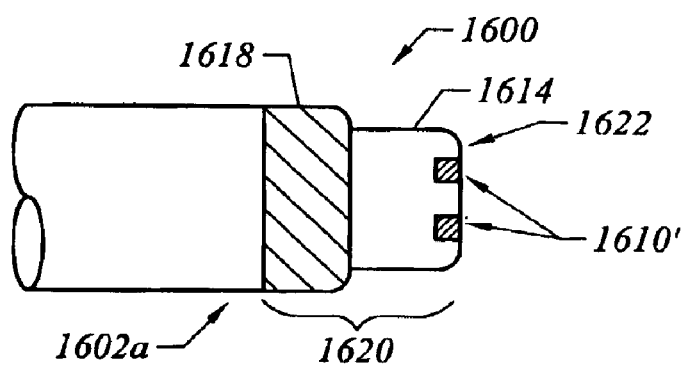
Figure 44C:
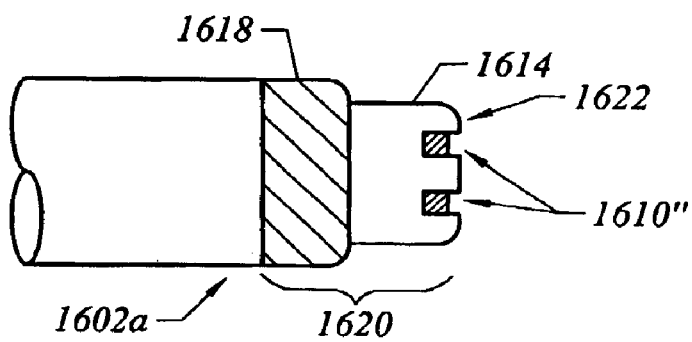

FIGS. 44A–C each show a side view of the distal or working end of an electrosurgical probe 1600, according to three different embodiments of the invention. Probe 1600 includes an electrode assembly 1620 at shaft distal end 1602a. Electrode assembly 1620 includes an electrically insulating electrode support 1614 having a treatment surface 1622, and a return electrode 1618 proximal to electrode support 1614. Electrode support 1614 may comprise a metal such as a ceramic, a glass, or a silicone rubber. Return electrode 1618 may comprise an exposed (non-insulated) portion of shaft distal end 1602a. As shown in FIG. 44A, a pair of electrode terminals 1610 extend distally from treatment surface 1622. In FIG. 44B, electrode terminals 1610' are substantially flush with treatment surface 1622. The configuration of FIG. 44B eliminates sharp edges or corners of electrode terminals 1610', thereby decreasing the risk of damage (e.g., physical trauma) to the patient's tissues. In the embodiment of FIG. 44C, electrode terminals 1610'' are recessed from treatment surface 1622 within electrode support 1614.

The invention is not limited to electrode assemblies having the configurations depicted in FIGS. 44A–C. Thus, other numbers, shapes, configurations, and arrangements of active electrode terminals, electrode supports, and return electrodes are also contemplated under the invention. Similarly, although electrode assembly 1620 is depicted in FIGS. 44A–C as being mounted terminally on shaft distal end 1602a, in alternative embodiments the electrode assembly may be mounted laterally on the shaft (e.g., FIG. 47B). Furthermore, although shaft distal end 1602a is shown as being essentially linear, in some embodiments distal end 1602a may be curved, bent, or bendable (e.g., FIG. 45B). For example, in one embodiment, shaft distal end 1602a may be curved such that treatment surface 1622 is at an angle in the range of from about 10° to 90° with respect to the longitudinal axis of the probe.

Figure 45A:
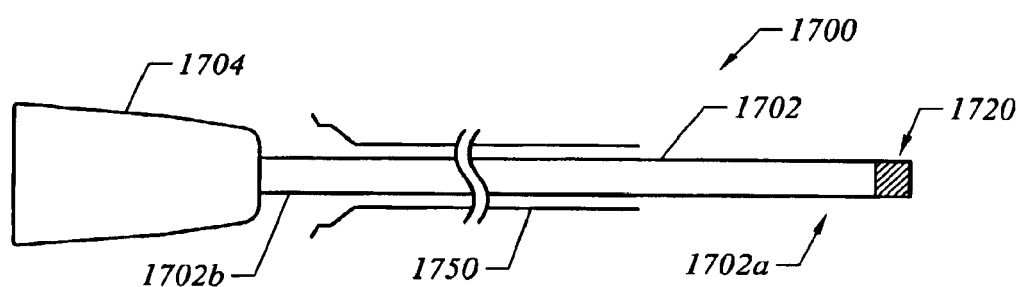
FIGS. 45A and 45B show an electrosurgical probe in a linear configuration and a curved configuration, respectively, according to the invention.
Figure 45B:
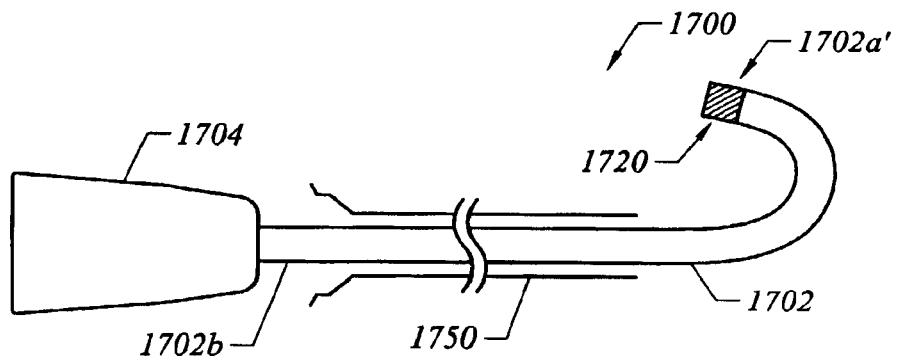

FIGS. 45A and 45B show an electrosurgical probe 1700 in a linear configuration and a curved configuration, respectively. Probe 1700 includes a shaft 1702, having a shaft distal end 1702a and a shaft proximal end 1702b, and a handle 1704 affixed to shaft proximal end 1702b. An electrode assembly 1720 is disposed at shaft distal end 1702a. Electrode assembly 1720 includes at least one active electrode terminal, e.g., a single electrode terminal or an electrode array comprising a plurality of active electrode terminals (e.g., FIGS. 17, 20, 23, 34, 43). Electrode assembly 1720 further includes at least one return electrode spaced from the active electrode(s) by an electrically insulating spacer or electrode support (e.g., FIGS. 44A–C). In one embodiment, electrode assembly 1720 may further include at least one aspiration electrode (e.g., FIGS. 36, 38) for digesting or vaporizing fragments of tissue removed from the surgical site during certain procedures.

Again with reference to FIGS. 45A–B, shaft distal end 1702a may adopt a linear configuration (FIG. 45A) or a curved configuration represented as 1702a' (FIG. 45B). Shaft distal end 1702a/1702a' may be transformed between the linear configuration and the curved configuration by pull wires, shape memory actuators, or other known mechanisms, for effecting selective deflection of shaft distal end 1702a. In an alternative embodiment, shaft distal end 1702a may be bent by the surgeon to the appropriate degree, e.g., using a conventional bending tool. A curved configuration, or selective deflection of shaft distal end 1702a, permits or facilitates guiding or steering the active electrode(s) to a target site during certain procedures. For example, shaft distal end 1702a' may be guided from a subcutaneous location to access the dermis for treatment of the "underside" of the skin (e.g., FIGS. 49A–B). (A more complete description of apparatus having a deflectable working end is provided in commonly assigned U.S. Pat. No. 5,697,909, the disclosure of which is incorporated by reference herein in its entirety.) Optionally, probe 1700 may be used in conjunction with a suitable introducer device 1750 or a hypodermic needle, e.g., for advancing shaft distal end 1702a percutaneously toward a target site (e.g., FIG. 46).

Figure 46:
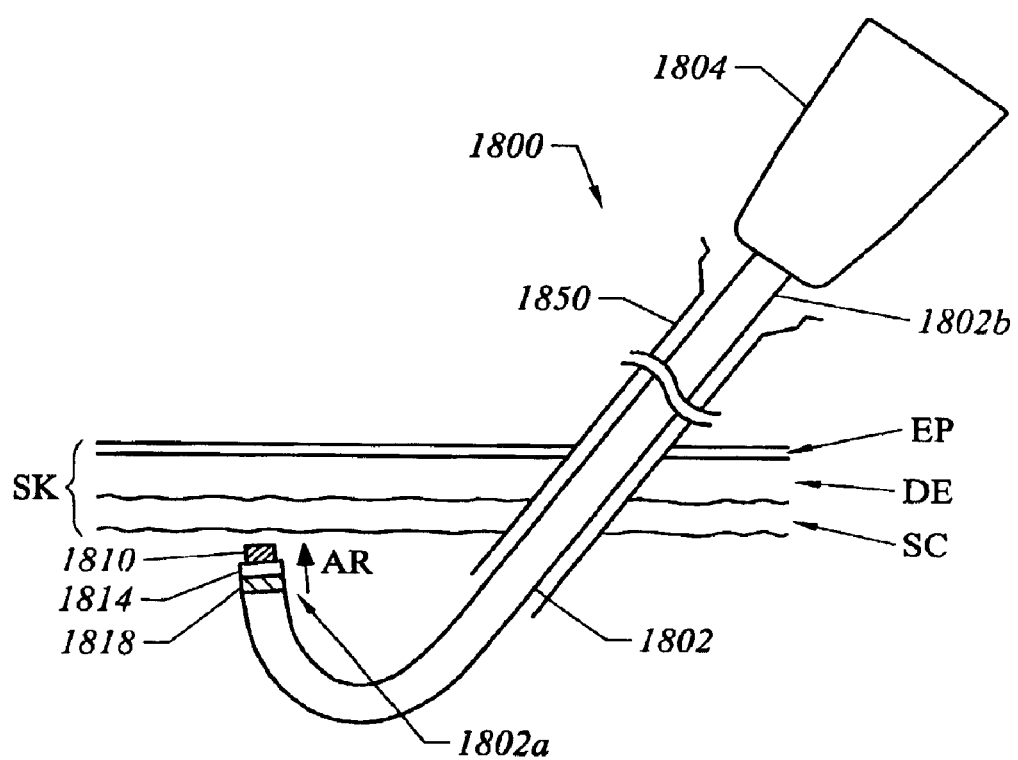
FIG. 46 illustrates subcutaneous access of the underside of the skin by a probe working end introduced via an introducer device, according to one embodiment of the invention.

FIG. 46 illustrates subcutaneous access of the underside of the skin, SK of a patient by the working end of an electrosurgical probe 1800, according to one embodiment of the invention. The skin, SK, includes the outer epidermis, EP, the dermis, DE, and the inner subcutis, SC. Probe 1800 includes an elongate shaft 1802 having a shaft distal end 1802a and a shaft proximal end 1802b. A handle 1804 is affixed to shaft proximal end 1802b. Shaft distal end 1802a is adapted for passage within an introducer device 1850. As shown, shaft distal end 1802a is capable of adopting a curved configuration. As an example, deflection of shaft distal end 1802a may be selectively induced by mechanical tension of a pull wire, or by a shape memory wire that expands or contracts by externally applied temperature changes. Such steering mechanisms are well known in the art.

After introducer device 1850 has penetrated the skin, SK, shaft distal end 1802a may be advanced beyond the distal end of introducer 1850 to a location beneath skin, SK (i.e., to a subcutaneous location). An electrode assembly is disposed at shaft distal end 1802a. As shown, the electrode assembly includes an active electrode 1810 disposed on an electrode support or spacer 1814, and a return electrode 1818 spaced proximally from active electrode 1810. However, other arrangements, numbers, and configurations for an electrode assembly of the probe are also within the scope of the invention. From the subcutaneous location of shaft distal end 1802a, active electrode 1810 may be guided, e.g., in the direction indicated by arrow, AR, toward the epidermis, EP to a target site within the dermis, DE or subcutis, SC.

In one embodiment, active electrode 1810 is positioned in the dermis, DE for contraction of collagen fibers within the dermis. Alternatively, or in addition, active electrode 1810 may be positioned in the subcutis, SC, which consists of a network of collagen and fat cells. Collagen fibers in the dermis and/or subcutis may be contracted by the controlled heating of tissue at a target site by application of a high frequency voltage between active electrode 1810 and return electrode 1818, with the power supply operating in the sub-ablation mode. Generally, the voltage parameters are within the ranges cited hereinabove for the sub-ablation mode, and the applied voltage heats the target tissue in a controlled manner to a temperature in the range of from about 60° C. to 70° C. Probe 1800 may be used for contracting the skin in the face or neck (e.g., in the submental or retroauricular locations) following, or as part of, a face-lift or neck-lift procedure. For example, prior to contracting the skin in the manner depicted in FIG. 46, excess skin or excess adipose tissue may be removed from a patient having a double chin or excessively large jowls. As an example, excess skin or adipose tissue may be removed electrosurgically (e.g., vaporized) using an electrosurgical apparatus of the invention operating in the ablation mode. Alternatively, the skin of a patient may be shrunk in the manner depicted in FIG. 46 following a conventional liposuction procedure. An example of a conventional liposuction procedure is the Klein method, which involves the use of a tumescent solution (Klein solution), as is well known in the art.

Figure 47A:
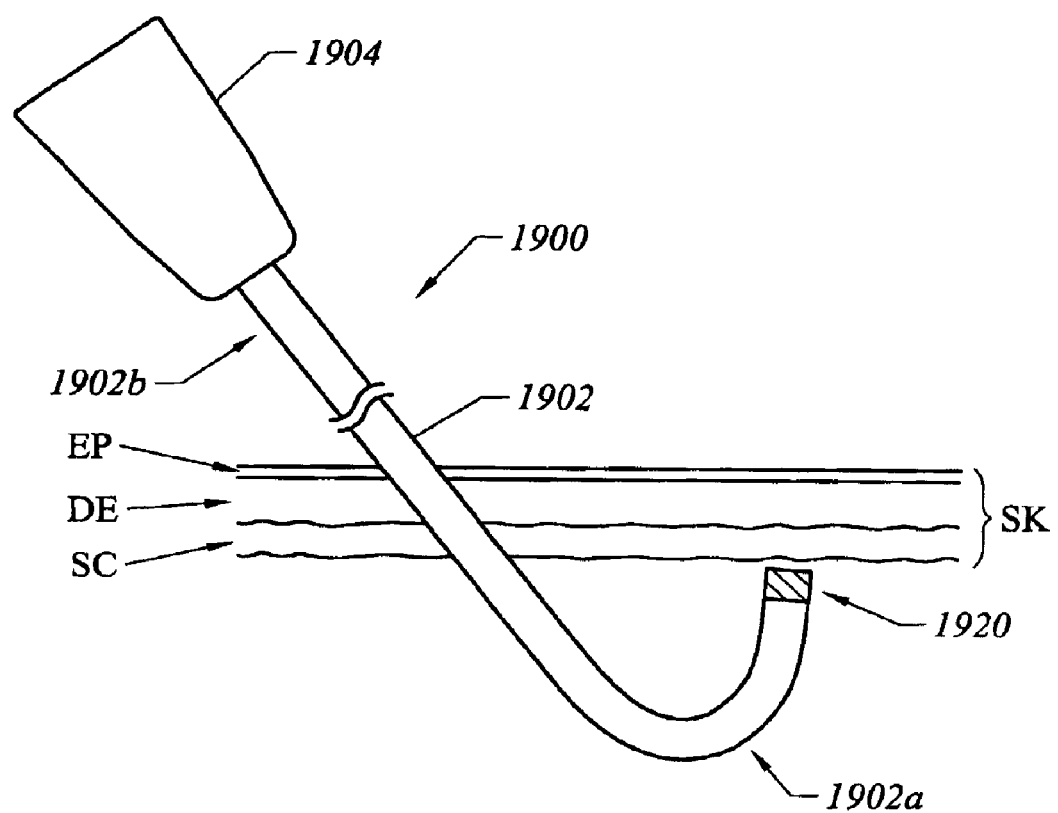
FIGS. 47A and 47B each illustrate subcutaneous access of the underside of the skin by a probe working end, according to two different embodiments of the invention.

FIG. 47A illustrates subcutaneous access of the underside of the skin, SK by the working end of an electrosurgical probe 1900, according to another embodiment of the invention. Probe 1900 includes a shaft 1902 having a shaft distal end 1902a and a shaft proximal end 1902b. A handle 1904 is affixed to shaft proximal end 1902b. Shaft 1902 is adapted for transformation between a linear configuration and a curved configuration. As an example, shaft 1902 may comprise a flexible material which can be deflected relative to the longitudinal axis of probe 1900, e.g., by mechanical tension of a pull wire, etc. In one embodiment, shaft distal end 1902a is selectively deflected during the course of a procedure, e.g., after distal end 1902a has reached a subcutaneous location. Alternatively, shaft distal end 1902a may be pre-bent to a suitable degree by the surgeon prior to beginning a procedure. In one embodiment, shaft 1902 is in the form of a slender rod having a diameter in the range of from about 0.2 mm to 3.0 mm, and often in the range of from about 0.25 mm to 1.5 mm. In one embodiment, shaft 1902 has dimensions similar to those of a 20–30 gauge hypodermic needle. Shaft distal end 1902a may be advanced percutaneously (in either the linear or curved configuration) by exertion of a mechanical force thereon, by electrosurgical channeling through the skin (via localized ablation of tissue), or by a combination of electrosurgical channeling and mechanical force. Alternatively, shaft distal end 1902a may be introduced through a small incision in skin, SK.

From the subcutaneous location depicted in FIG. 47A, electrode assembly 1920 may be guided to a target location within dermis, DE, or subcutis, SC, by manipulating probe 1900 via handle 1904. After, electrode assembly 1920 has been positioned at a target location within dermis, DE or subcutis, SC, a sub-ablation voltage is applied between the active electrode and the return electrode, wherein the voltage effects the controlled heating of the tissue in the vicinity of electrode assembly 1920. For the contraction of collagen fibers, the tissue is typically heated to a temperature in the range of from about 60° C. to 70° C. In an alternative form of treatment, the dermis may be heated by the application of a sub-ablation voltage in order to induce localized collagen deposition. In this manner, the skin may be treated from the underside to modify the skin in a range of cosmetic procedures, for example, by contracting collagen fibers in the dermis, and/or by stimulating deposition of new collagen.

Figure 47B:
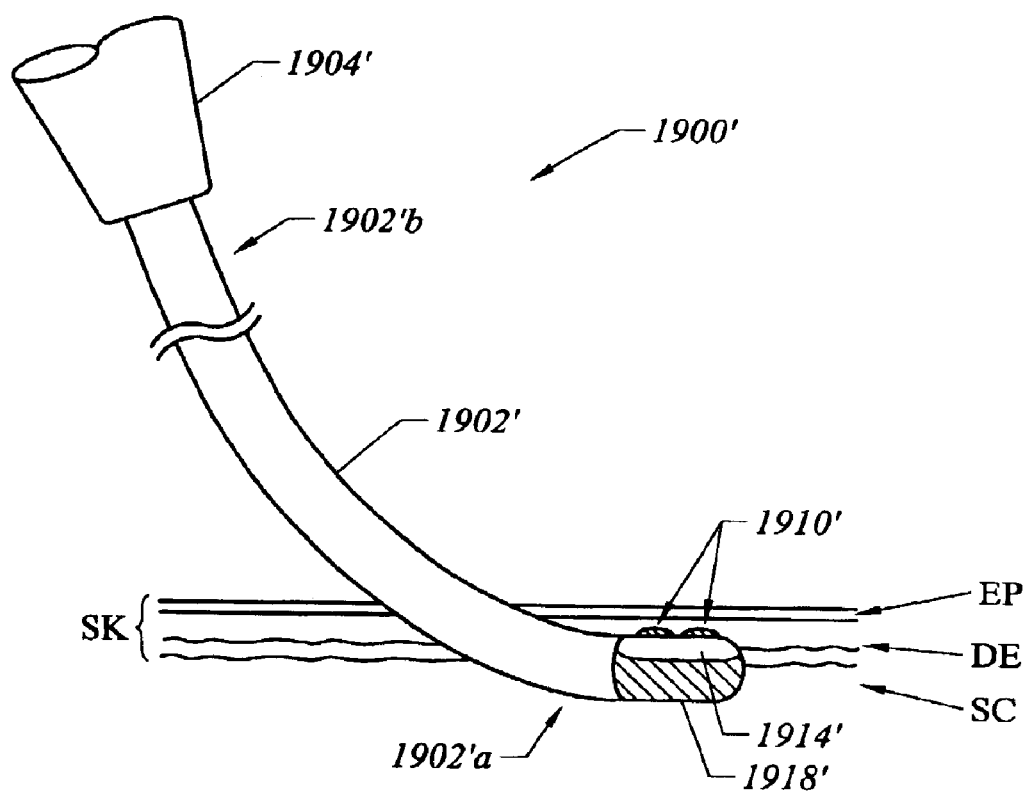

FIG. 47B shows subcutaneous access of the dermis, DE of the skin, SK by the working end of an electrosurgical probe 1900', according to another embodiment of the invention. Probe 1900' includes a shaft 1902' having a shaft distal end 1902'a and a shaft proximal end 1902'b. A handle 1904' is affixed to shaft proximal end 1902'b. Shaft distal end 1902'a has a curved configuration. Probe 1900' may be provided (i.e., manufactured) with the shaft having a range of different lengths, diameters, and curvatures, for use in a range of different target sites and dermatological procedures. In one embodiment, shaft distal end 1902'a may be bent to a suitable degree by the surgeon prior to a procedure in order to "customize" the probe for the particular procedure/target site. In one embodiment, shaft 1902' is in the form of a slender rod having a diameter in the range of from about 0.2 mm to 3.0 mm. In the embodiment of FIG. 47B, active electrode terminals 1910' are arranged laterally on shaft distal end 1902'a. Active electrode terminals 1910' are spaced from a return electrode 1918' by an electrically insulating electrode support 1914'. The lateral arrangement of active electrode terminals 1910' and electrode support 1914' facilitates access to the dermis, DE from the underside of the skin during certain procedures. Shaft distal end 1902'a may be advanced to a subcutaneous location, for example, through a small incision in skin, SK. In use, probe 1900' is coupled to a high frequency power supply capable of operating in at least the sub-ablation mode. In some embodiments, probe 1900' is coupled to a high frequency power supply capable of operating in both the sub-ablation mode and the ablation mode. For treating the skin, SK (e.g. for contraction of collagen fibers in the dermis, DE, or subeutis, SC) probe 1900' is typically operated in the sub-ablation mode.

Figure 48A:
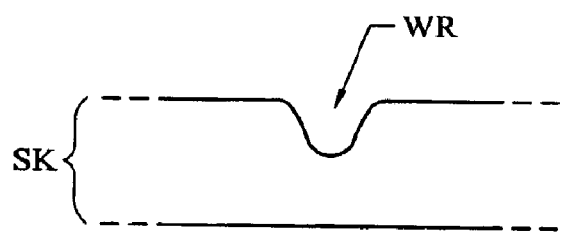
FIGS. 48A–C represent treatment of a wrinkle in the skin via direct insertion of an electrosurgical instrument into a sub-epidermal layer, according to one embodiment of the invention.
Figure 48B:
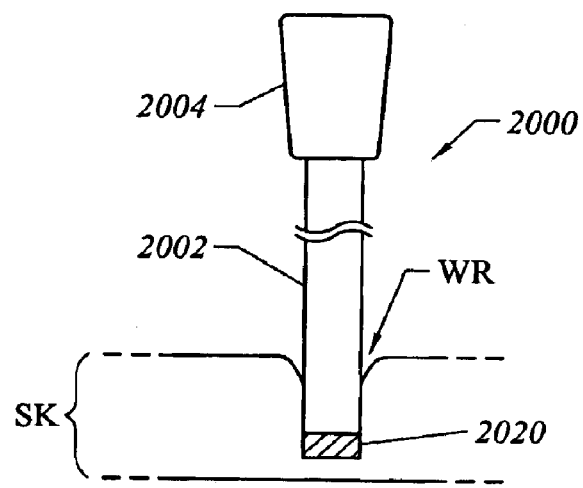
Figure 48C:
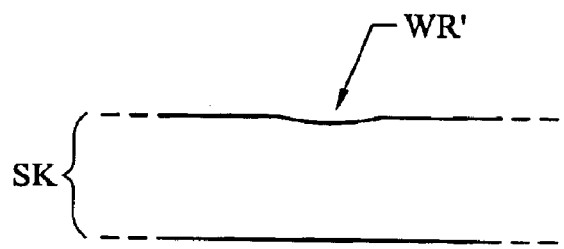

FIGS. 48A–C schematically represents an apparatus and procedure for treatment of a wrinkle in the skin of a patient. FIG. 48A shows a wrinkle, WR targeted for treatment in the skin, SK. FIG. 48B shows an electrosurgical probe 2000 including a shaft 2002, a handle 2004 at the proximal end of shaft 2002, and an electrode assembly 2020 at the distal end of shaft 2002. Electrode assembly 2020 includes at least one active electrode terminal and a return electrode spaced from the active electrode terminal(s). As an example, electrode assembly 2020 may have a configuration as described hereinabove for electrosurgical instruments according to the various embodiments of the invention. Shaft 2002 is directly inserted in skin, SK at the location of wrinkle, WR such that electrode assembly 2020 is positioned in the dermis beneath wrinkle, WR. Thereafter, a high frequency voltage is applied between the active electrode terminal(s) and the return electrode in the sub-ablation mode, in order to effect the controlled heating of the dermis at the location beneath the wrinkle, WR. The voltage parameters may be pre-selected or adjusted to provide sufficient heat to the dermis, whereby the dermis is induced to deposit new collagen directly beneath the wrinkle, WR. As a result of such localized collagen deposition, the targeted wrinkle is reduced or removed, as indicated at the location labeled WR' in FIG. 48C.

Figure 49A:
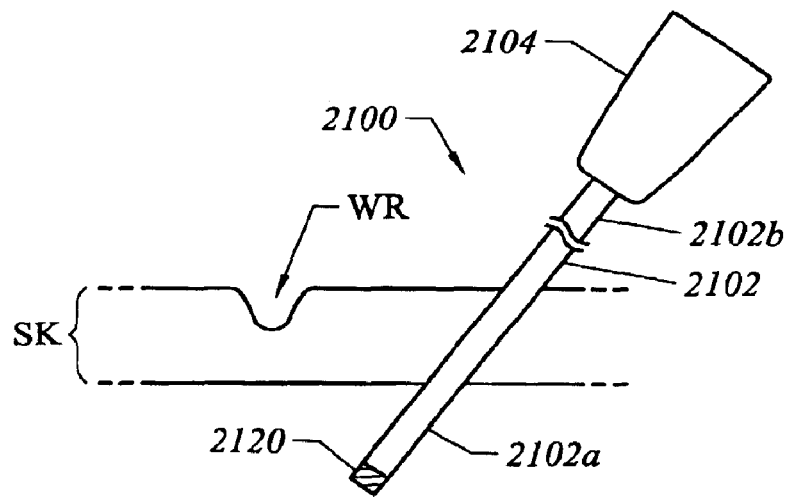
FIGS. 49A–C represent treatment of a wrinkle in the skin via subcutaneous access of the underside of the skin by an electrosurgical instrument, according to another embodiment of the invention.
Figure 49B:
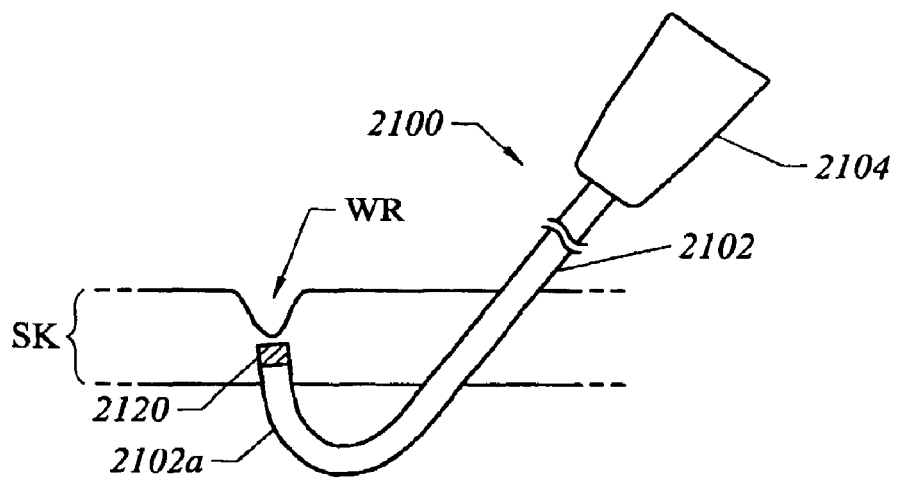
Figure 49C:

FIGS. 49A–C represent treatment of a wrinkle, WR in the skin via subcutaneous access of the underside of the skin, SK by an electrosurgical probe 2100. Probe 2100 includes a shaft 2102, having a shaft distal end 2102a and a shaft proximal end 2102b; a handle 2104 at shaft proximal end 2102b; and an electrode assembly 2120 at shaft distal end 2102a. Shaft distal end 2102a is adapted for being deflected to a curved or bent configuration (FIG. 49B). FIG. 49A shows shaft 2102 advanced through skin, SK such that electrode assembly 2120 is in a subcutaneous location, with shaft distal end 2102a in a linear configuration. Shaft distal end 2102a is deflected as appropriate in order to guide electrode assembly 2120 to a location in the dermis beneath a wrinkle, WR targeted for treatment, as shown in FIG. 49B. After electrode assembly 2120 has been suitably positioned in relation to wrinkle, WR, a high frequency voltage is applied between the active electrode terminal(s) and the return electrode, in the sub-ablation mode, wherein the applied voltage is selected to effect the controlled heating of the dermis such that collagen deposition is induced at a location directly beneath the wrinkle, WR. As a result of such localized collagen deposition, the targeted wrinkle is removed or reduced, as indicated at the location labeled WR' in FIG. 49C.

Figure 50:
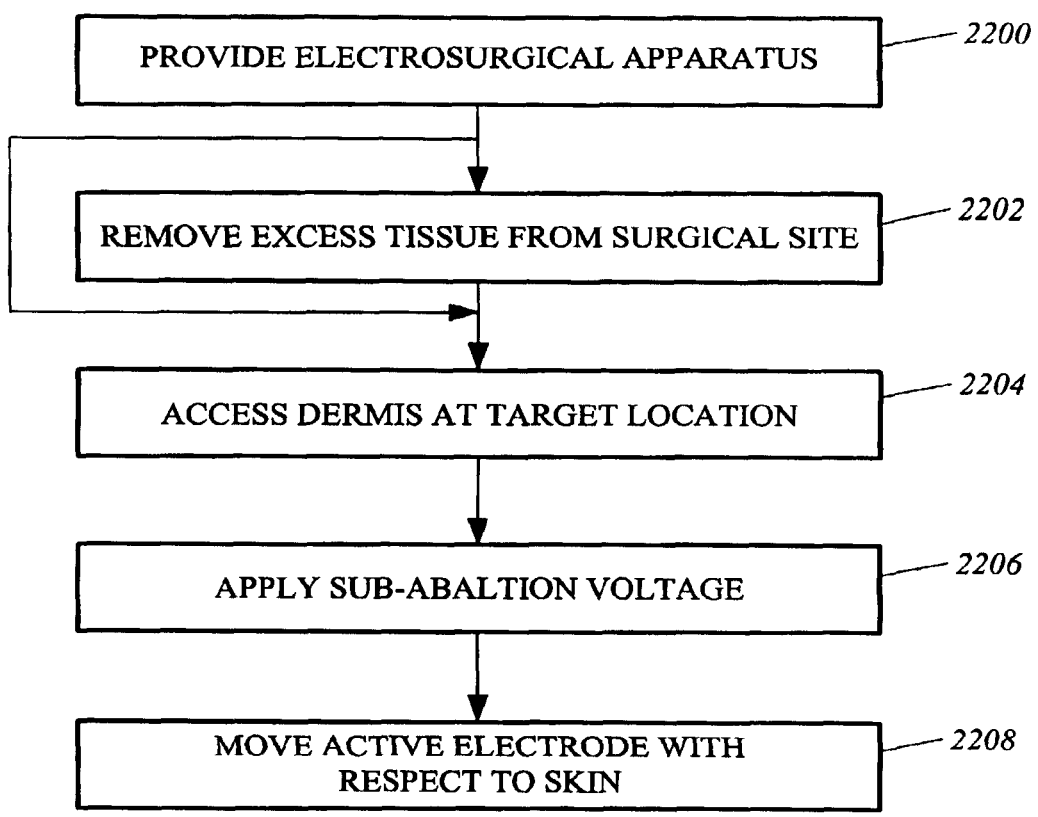
FIG. 50 schematically represents a series of steps involved in a method for electrosurgically treating the skin of a patient, according to one embodiment of the invention.

FIG. 50 schematically represents a series of steps involved in a method for electrosurgically treating the skin of a patient, according to one embodiment of the invention. As an example, the method of FIG. 50 may be used after, or as part of, an electrosurgical or conventional liposuction procedure. The method of FIG. 50 may also be used after, or as part of, an electrosurgical or conventional face-lift or neck-lift procedure. Step 2200 involves providing an electrosurgical apparatus or system. The apparatus or system may have the characteristics, features, and elements described hereinabove for various embodiments of the invention. Typically, the apparatus comprises an electrosurgical probe including a shaft, and an electrode assembly at the distal or working end of the shaft. The electrode assembly includes at least one active electrode and a return electrode. The active electrode and the return electrode are coupled to opposite poles of a high frequency power supply, wherein the power supply can be operated in the ablation mode or the sub-ablation mode. In one embodiment, the shaft distal end is bent or deflectable, whereby the electrode assembly can be steered or guided to a particular target location.

Optional step 2202 involves removing excess tissue in a region of the skin to be treated. Such excess tissue may be adipose tissue, or skin tissue in an area from which adipose tissue has been removed during a liposuction procedure. Step 2202 may be performed electrosurgically, for example, using various instruments and methods described herein, or by conventional mechanical instruments. In one embodiment, electrosurgical removal of excess tissue in step 2202 involves positioning the active electrode in at least close proximity to the tissue to be removed, and thereafter applying a high frequency voltage between the active electrode and the return electrode in the ablation mode. Typically, the voltage applied in the ablation mode is within the ranges cited hereinabove, for example, from about 200 volts RMS to 1000 volts RMS. Electrosurgical instruments and methods of the invention offer a number of advantages, as compared with conventional procedures, including minimal scaring, electrosurgical coagulation of severed blood vessels resulting in improved visibility at the surgical site and less bleeding, and more rapid recovery from the procedure. In one embodiment, the method described with reference to FIG. 50 may be used to shrink the skin in an area where a liposuction procedure has been performed, prior to closing the surgical site.

Step 2204 involves accessing the dermis at the location targeted for treatment. In one embodiment, an incision is formed in the skin, e.g., at a submental location, to provide a flap of skin; and the flap of skin may be elevated away from the neck and face to allow positioning of the shaft distal end beneath the flap of skin. In another embodiment, step 2204 involves advancing the shaft distal end through the skin until the electrode assembly is positioned at a subcutaneous location, and thereafter guiding the shaft distal end through the subcutis layer toward the epidermis until the electrode assembly is positioned within the dermis. In an alternative embodiment, step 2204 involves advancing the shaft distal end through the epidermis toward the dermis, such that the electrode assembly/active electrode is positioned within the dermis. In another embodiment, the shaft distal end may be introduced via an incision in the skin, wherein the incision was made for the purpose of removing excess tissue during step 2202.

Step 2206 involves applying a high frequency voltage between the active electrode and the return electrode, in the sub-ablation mode, such that the dermis undergoes localized heating in a controlled manner. For shrinkage of the skin via contraction of collagen fibers in the dermis, the dermal tissue is typically heated to a temperature in the range of from about 60° C. to 70° C. In one embodiment, the dermal tissue at the target location is heated via resistive heating as a result of current flow through the tissue in the vicinity of the active electrode.

Step 2208 involves moving the active electrode with respect to the skin. In one embodiment, the active electrode is moved during step 2206. Alternatively, after treating the skin at a first location as a result of step 2206, the power can be turned off, and the active electrode may be moved to a new location of the skin prior to turning the power back on. By moving the active electrode according to step 2208, a relatively large area of tissue can be treated. Typically, the active electrode is moved by manipulating the probe via the handle.

Figure 51A:
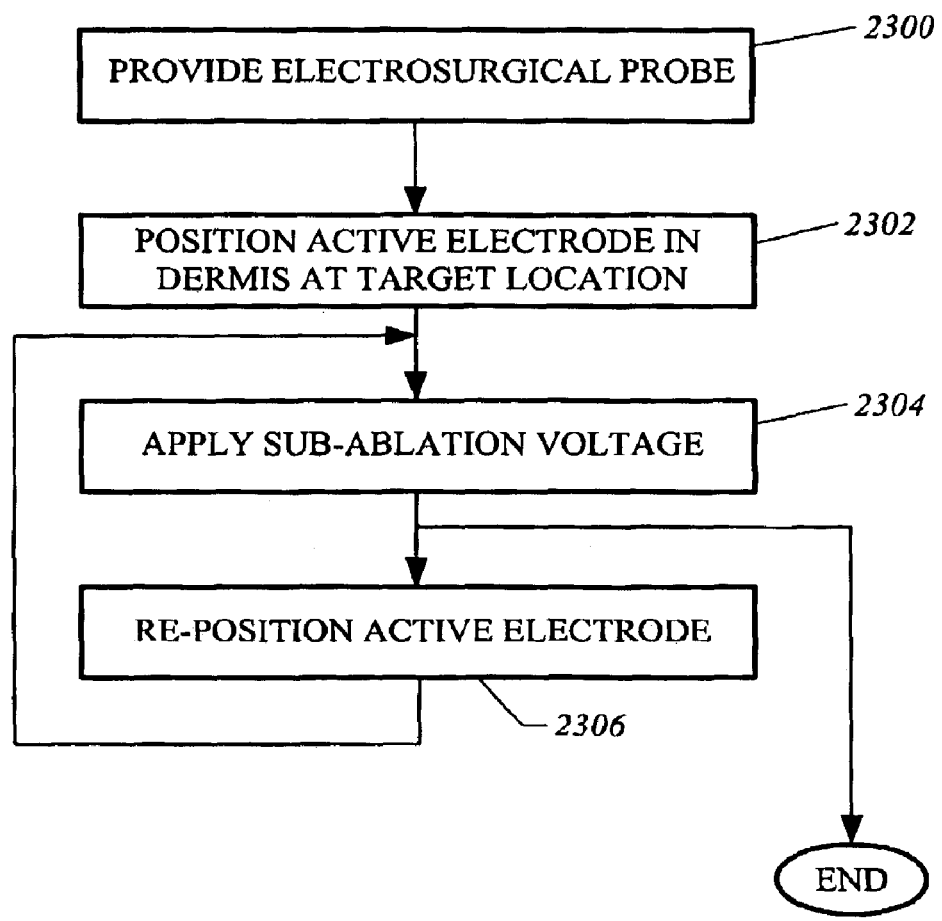
FIGS. 51A and 51B each schematically represent a series of steps involved in a method for electrosurgically removing wrinkles in the skin of a patient, according to two different embodiments of the invention.

FIG. 51A schematically represents a series of steps involved in a method for electrosurgically reducing or removing wrinkles in the skin of a patient, according to another embodiment of the invention. Step 2300 involves providing an electrosurgical probe. Typically, the probe includes a shaft having a narrow diameter, e.g., having a diameter in the range of from about 0.25 mm to 2.5 mm, and an electrode assembly disposed at the shaft distal end. The electrode assembly typically includes an active electrode and a return electrode spaced from the active electrode by an electrically insulating electrode support or spacer. In one embodiment, the electrode assembly and the shaft distal end are adapted for direct penetration into the skin through the epidermis, and advancement of the electrode assembly into the dermis. The probe may also have other features, characteristics, or elements, as described hereinabove for the various embodiments of the invention. Step 2302 involves positioning the active electrode in the dermis at a target location. Typically, the target location is directly beneath a wrinkle targeted for treatment. Most commonly, wrinkles targeted for treatment are on the face or neck, and often such wrinkles are located around the eyes or around the mouth.

While the probe is positioned according to step 2302, step 2304 involves applying a sub-ablation voltage between the active electrode and the return electrode, wherein the sub-ablation voltage is selected to induce collagen deposition in the dermis at the location of the target wrinkle. Such collagen deposition removes or reduces the wrinkle targeted for treatment. Typically, the sub-ablation voltage is within the ranges cited hereinabove for the sub-ablation mode, for example, in the range of from about 20 volts RMS to 90 volts RMS, at a frequency in the range of from about 50 kHz to 500 kHz. In the case of relatively long wrinkles, treatment may necessitate repositioning of the active electrode within the dermis in order to treat an additional region of the wrinkle. Accordingly, step 2306 involves repositioning the active electrode with respect to the wrinkle targeted for treatment. Thereafter, step 2304 may be repeated to induce collagen deposition at the additional region. Steps 2304 and 2306 may be sequentially repeated until the wrinkle targeted for treatment has been treated over an appropriate length. Often, the entire length of the wrinkle is treated according to the method of FIG. 51A.

Figure 51B:
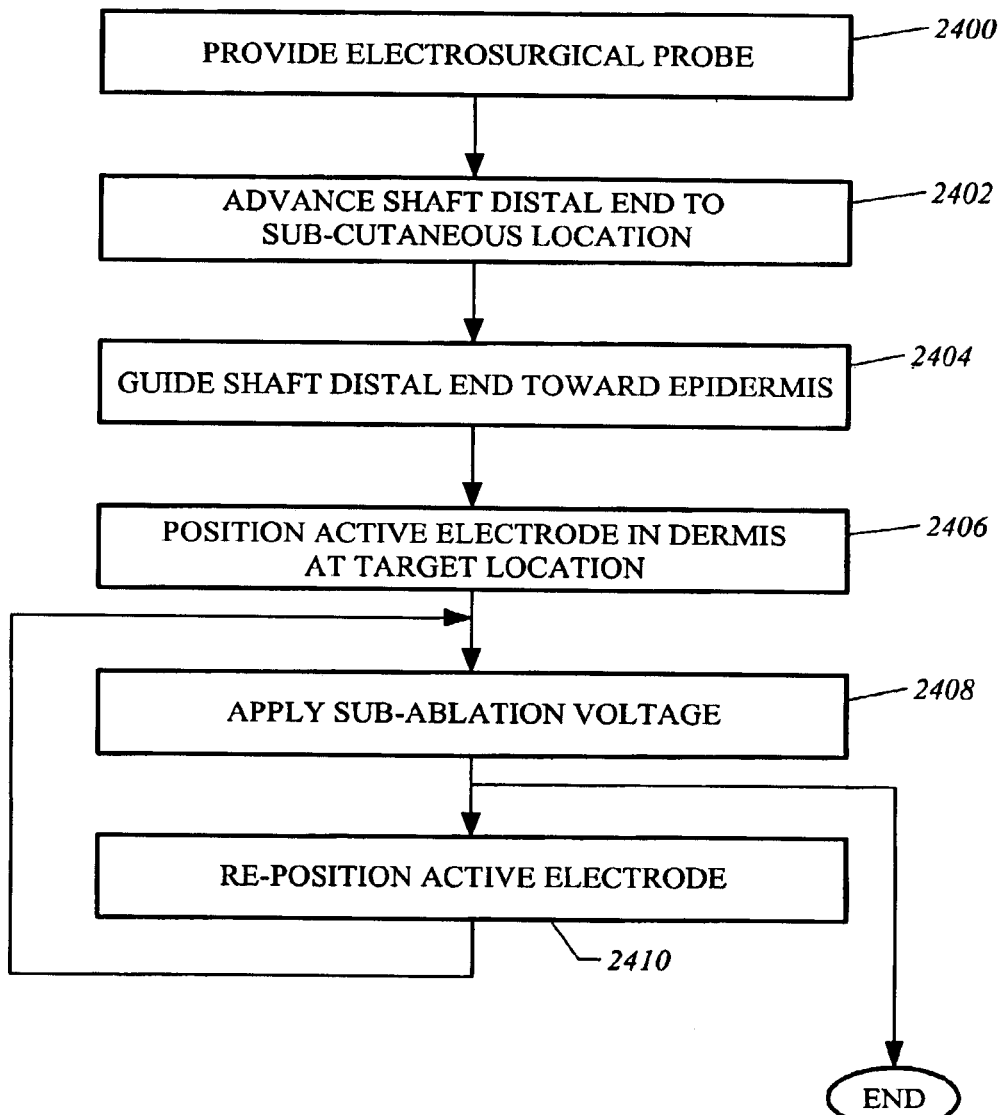

FIG. 51B schematically represents a series of steps involved in a method for electrosurgically removing wrinkles in the skin of a patient, according to another embodiment of the invention, wherein step 2400 involves providing an electrosurgical probe. Typically, the probe provided in step 2400 includes a narrow diameter shaft, e.g., having a diameter in the range of from about 0.25 mm to 2.5 mm, and an electrode assembly disposed at the shaft distal end. In one embodiment, the shaft is adapted for passage within an introducer needle for percutaneous advancement to a location beneath the skin of the patient. In another embodiment, the shaft is adapted for channeling directly through the skin of the patient, without the use of an introducer needle, until the shaft distal end is positioned at a subcutaneous location (i.e., beneath the skin). The probe may also have certain additional elements, features, or characteristics as described hereinabove for the various embodiments of the invention. In one embodiment, the shaft distal end is curved or deflectable, whereby the electrode assembly can be guided to a particular target location.

Step 2402 involves advancing the shaft in a first direction, from the epidermis toward the subcutis, until the shaft distal end is at a subcutaneous location adjacent to the wrinkle targeted for treatment. Thereafter, step 2404 involves guiding the shaft distal end in a second direction, toward the epidermis, such that the active electrode is positioned within the dermis at a target location (step 2406). Typically, the target location is directly beneath the wrinkle targeted for treatment. Step 2408 involves applying a sub-ablation voltage between the active electrode and the return electrode, wherein the sub-ablation voltage is selected to be effective in inducing collagen deposition in the dermis at the target location, essentially as described hereinabove with reference to FIG. 51A. Typically, the applied voltage has parameters within the ranges cited hereinabove for the sub-ablation mode. Prior to or during step 2408, an electrically conductive fluid may be delivered to the electrode assembly or to the target location, to provide a current flow path between the active electrode and the return electrode. Optional step 2410 involves repositioning the active electrode beneath an additional region of the wrinkle targeted for treatment. Thereafter, step 2408 may be repeated to induce collagen deposition at the additional region, essentially as described hereinabove for steps 2304 and 2306 according to the method of FIG. 51A.

While the exemplary embodiments of the present invention have been described in detail, by way of example and for clarity of understanding, a variety of changes, adaptations, and modifications will be obvious to those of skill in the art. Therefore, the scope of the present invention is limited solely by the appended claims.

What is claimed is:

1. A method for shrinking the skin at a target site of a patient's face or neck, comprising:

a) providing a probe, the probe including a shaft having a shaft distal end, an active electrode at the shaft distal end, and a return electrode spaced from the active electrode;

b) advancing the shaft distal end through the skin from the epidermis toward the subcutis until the shaft distal end is at a subcutaneous location;

c) passing the shaft distal end through the subcutis toward the dermis; and d) applying a sub-ablation voltage between the active electrode and the return electrode, wherein the sub-ablation voltage effects contraction of the skin in the vicinity of the target site.

2. The method of claim 1, wherein the sub-ablation voltage is a high frequency voltage in the range of from about 20 volts RMS to 90 volts RMS.

3. The method of claim 1, further comprising:

prior to said step b), removing excess tissue from the patient's face or neck.

4. The method of claim 3, wherein said removing step comprises excising a quantity of excess skin from the patient's face or neck.

5. The method of claim 4, wherein at least a portion of the excess skin is excised electrosurgically.

6. The method of claim 3, wherein said removing step comprises removing a quantity of adipose tissue from the vicinity of the target site.

7. The method of claim 6, wherein said removing step comprises performing liposuction in the vicinity of the target site.

8. The method of claim 6, wherein said removing step comprises:

e) positioning the active electrode in at least close proximity to the adipose tissue; and f) applying a second voltage between the active electrode and the return electrode, wherein the second voltage is sufficient to ablate or modify the adipose tissue.

9. The method of claim 8, wherein the second voltage is in the range of from about 200 volts RMS to 1000 volts RMS.

10. The method of claim 8, wherein the second voltage is sufficient to liquefy the adipose tissue.

11. The method of claim 1, wherein the voltage of said step d) is applied from a high frequency power supply adapted for operation in the sub-ablation mode and the ablation mode.

12. The method of claim 1, wherein said step b) comprises electrosurgically channeling through the epidermis of the patient's skin.

13. The method of claim 12, wherein said electrosurgical channeling comprises:

g) positioning the active electrode in at least close proximity to the epidermis; and h) applying a high frequency voltage between the active electrode and the return electrode.

14. The method of claim 1, further comprising:

k) moving the active electrode with respect to the skin.

15. The method of claim 14, wherein said step k) comprises moving the active electrode during said step c).

16. A method for removing or reducing wrinkles on the skin of a patient, comprising:

a) providing a probe, the probe including a shalt having a shaft distal end, an active electrode at the shalt distal end, and a return electrode spaced from the active electrode;

b) subcutaneously accessing the patient's dermis with the shaft distal end, wherein the active electrode is positioned in at least close proximity to a wrinkle targeted for treatment wherein said step b) comprises advancing the shaft distal end in a first direction through the epidermis toward the subcutis until the shaft distal end is positioned subcutaneously; and advancing the shaft distal end in a second direction from the subcutaneous position toward the epidermis; and c) applying a sub-ablation voltage between the active electrode and the return electrode, the sub-ablation voltage effective in removing or reducing the wrinkle targeted for treatment.

17. The method of claim 16, wherein said step b) comprises:

f) positioning the active electrode within the dermis.

18. The method of claim 17, wherein the shaft distal end is transformable between a linear configuration and a curved configuration, and wherein said step d) is performed with the shaft distal end in the linear configuration.

19. The method of claim 18, further comprising:

g) prior to said step e), transforming the shaft distal end to the curved configuration.

20. The method of claim 17, wherein the shaft distal end is steerable, and said step b) comprises steering the shaft distal end toward the dermis.

21. The method of claim 17, wherein said step f) comprises positioning the active electrode within the dermis at the location of the wrinkle targeted for treatment.

22. The method of claim 17, wherein said step d) comprises:

h) introducing an introducer needle into the skin; and i) passing the shaft distal end through the introducer needle.

23. The method of claim 16, wherein said step b) comprises: positioning the active electrode in the dermis beneath a first region of the wrinkle targeted for treatment.

24. The method of claim 23, further comprising:

j) after said step c), repositioning the active electrode in the dermis beneath an additional region of the wrinkle targeted for treatment and thereafter repeating said step c).

25. The method of claim 16, wherein said step c) induces collagen deposition in the dermis at a location beneath the wrinkle targeted for treatment.

26. The method of claim 16, wherein the sub-ablation voltage has a frequency in the range of from about 50kHz to 500 kHz.

27. The method of claim 26, wherein the sub-ablation voltage is at a level in the range of from about 20 volts RMS to 90 volts RMS.

28. The method of claim 26, wherein the wrinkle is on the face or neck.

29. The method of claim 16, wherein the wrinkle is around the eye or around the mouth.

* * * * *